US011919971B2

(12) United States Patent
Leslie et al.

(10) Patent No.: US 11,919,971 B2
(45) Date of Patent: Mar. 5, 2024

(54) AQUEOUS BIOMOLECULE COUPLING ON CO2-PLASMA-ACTIVATED SURFACES

(71) Applicant: PRESIDENT AND FELLOWS OF HARVARD COLLEGE, Cambridge, MA (US)

(72) Inventors: Daniel Christopher Leslie, Brookline, MA (US); Thomas Doyle, Boston, MA (US); Anna Waterhouse, Brookline, MA (US); Melissa Rodas, Boston, MA (US); Alexander L. Watters, North Andover, MA (US); Michael Super, Lexington, MA (US); Donald E. Ingber, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 144 days.

(21) Appl. No.: 16/302,023

(22) PCT Filed: May 16, 2017

(86) PCT No.: PCT/US2017/032928
§ 371 (c)(1),
(2) Date: Nov. 15, 2018

(87) PCT Pub. No.: WO2017/201064
PCT Pub. Date: Nov. 23, 2017

(65) Prior Publication Data
US 2019/0144567 A1 May 16, 2019

Related U.S. Application Data
(60) Provisional application No. 62/336,940, filed on May 16, 2016.

(51) Int. Cl.
C07K 17/08 (2006.01)
C08L 25/06 (2006.01)
(Continued)

(52) U.S. Cl.
CPC .............. *C07K 17/08* (2013.01); *C08L 25/06* (2013.01); *C08L 83/04* (2013.01);
(Continued)

(58) Field of Classification Search
CPC .... C07K 17/08; C07K 14/4726; C07K 16/00; C08L 25/06; C08L 83/04; C08L 2203/02;
(Continued)

(56) References Cited

U.S. PATENT DOCUMENTS 5,132,108 A 7/1992 Narayanan et al.
5,270,199 A 12/1993 Ezekowitz
(Continued)

FOREIGN PATENT DOCUMENTS

WO WO2008135008 * 11/2008 ............. H01J 37/32
WO 2011090954 A2 7/2011
(Continued)

OTHER PUBLICATIONS

Exalpha; Buffer Formulations, 2017, p. 1-10.*
(Continued)

Primary Examiner — Robert S Jones, Jr.
Assistant Examiner — Jiangtian Xu
(74) Attorney, Agent, or Firm — Nixon Peabody LLP; David S. Resnick; Nicole D. Kling

(57) ABSTRACT

This disclosure provides, e.g., methods for coupling Formation of Surface Carboxylates on PES an entity to a solid substrate. The method can comprise treating the with Exposure Time substrate with a plasma, e.g., a $CO_2$ plasma, to increase its reactivity. The entity can be, e.g., a biological polymer that binds a microbe. Substrates produced by these
(Continued)

methods can be used in a variety of applications, including hemodialysis and diagnostic assays.

22 Claims, 7 Drawing Sheets

Specification includes a Sequence Listing.

(51) Int. Cl.
    *C08L 83/04*     (2006.01)
    *G01N 33/543*     (2006.01)
    *G01N 33/545*     (2006.01)
    *C08K 5/05*     (2006.01)

(52) U.S. Cl.
    CPC ..... *G01N 33/54393* (2013.01); *G01N 33/545* (2013.01); *C08K 5/05* (2013.01); *C08L 2203/02* (2013.01)

(58) Field of Classification Search
    CPC ... G01N 33/54393; G01N 33/545; C08K 5/05
    See application file for complete search history.

(56) References Cited

U.S. PATENT DOCUMENTS

| | | | |
|---|---|---|---|
| 6,846,649 | B1 | 1/2005 | Thiel et al. |
| 2004/0229212 | A1 | 11/2004 | Thiel et al. |
| 2014/0100131 | A1* | 4/2014 | Gao ................. G01N 33/54353 435/5 |
| 2014/0114267 | A1* | 4/2014 | Hodgkinson ........... A61L 15/26 604/365 |
| 2015/0377881 | A1* | 12/2015 | Super ................... G01N 33/569 435/7.92 |
| 2016/0319092 | A1* | 11/2016 | Paulussen .............. B01D 65/08 |

FOREIGN PATENT DOCUMENTS

| | | |
|---|---|---|
| WO | 2012100099 A2 | 7/2012 |
| WO | 2013012924 A3 | 4/2013 |
| WO | 2013106588 A1 | 7/2013 |
| WO | 2014014788 A2 | 1/2014 |
| WO | 2014144325 A1 | 9/2014 |
| WO | 2014190040 A1 | 11/2014 |
| WO | 2015095604 A3 | 11/2015 |

OTHER PUBLICATIONS

Hermanson, G.T.; Bioconjugate Techniques, 2008, p. 216-219.*
Siow et al.; Plasma Processes and Polymers, 2006, vol. 3, p. 392-418.*
Bryjak et al.; Langmuir, 1999, vol. 15, p. 6400-6404.*
Wolf, R.A.; Plastic Surface Modification: Surface Treatment, Decoration, and Adhesion, 2010, p. 53.*
Wavhal et al., Desalination, 2005, vol. 172, p. 189-205.*
Pal et al., Journal of Membrane Science, 2008, vol. 323, p. 1-10.*
Arrayit Corporation "Products—Microarray Substrates & Slides" (2015).
Bos, Gerrit Willem "Albumin-Heparin matrices loaded with growth factor as substrates for endothelial cell seeding," Thesis defended Aug. 21, 1998 at Universiteit Twente.
Cras et al., "Comparison of chemical cleaning methods of glass in preparation for silanization," Biosensors & Bioelectronics. 14:683-8 (1999).
Didar et al., "Improved treatment of systemic blood infections using antibiotics with extracorporeal opsonin hemoadsorption," Biomaterials. 67:382-92 (2015).
Kang et al.,"An extracorporeal blood-cleansing device for sepsis therapy," Nat. Med. 20(10):1211-6 (2014).
"Lifetechnologies "Carbodiimide Crosslinker Chemistry" retrieved Jul. 13, 2015, from the world wide web, accessible at lifetechnologies. com/us/en/home/life-science/protein-biology/protein-biology-learning-center/protein-biology-resource-library/pierce-protein-methods/carbodiimide-crosslinker-chemistry.html".
Lopez et al., "Biofunctionalization of silicone polymers using poly(amidoamine) dendrimers and a mannose derivative for prolonged interference against pathogen colonization," Biomaterials. 32(19):4336-46 (2011).
Ma et al., "Surface modification of polypropylene and compatibilization of interfaces in incompatible blends of polypropylene with polystyrene by plasma of CO2," Applied Surface Science. 255:7483-94 (2009).
Poncin-Epaillard et al., "An easy route to synthesize a polyolefine surface bearing carboxylic groups," 5th European Adhesion Conference: Sep. 18-21, 2000.
Poncin-Epaillard et al., "Characterization of CO2 plasma and interactions with polypropylene film," Plasmas and Polymers. 7(1) (2002).
Shen et al., "The bioactivity of rhBMP-2 immobilized poly(lactide-co-glycolide) scaffolds," Biomaterials. 30(18):3150-7 (2009).
Terlingen et al., "Introduction of functional groups on polyethylene surfaces by a carbon dioxide plasma treatment," J. Applied Polymer Science. 57:969-82 (1995).
Blackman et al., "Growth of Listeria monocytogenes as a Biofilm on Various Food-Processing Surfaces", J Food Prot 59:827-31 (1996).
Chang et al., "Crystallization and Preliminary X-ray Analysis of a Trimeric Form of Human Mannose Binding Protein" J Mol Biol. 241:125-127 (1994).
Costerton et al., "Microbial Biofilms" Annu Rev Microbiol, 49:711-45 (1995).
Frank et al., "Surface-adherent Growth of Listeria monocytogenes is Associated with Increased Resistance to Surfactant Sanitizers and Heat" Food Prot, 53:550-554 (1990).
Gebauer et al., "Engineered protein scaffolds as next-generation antibody therapeutics", Current opinion in chemical biology, 13(3), 245-255 (2009).
Hudson "Recombinant antibody fragments", Curr. Opin. Biotechnol. 9:395-402 (1998).
Krysinski et al., "Effect of Cleaners and Sanitizers on Listeria monocytogenes Attached to Product Contact Surfaces" Food Prot, 55:246-51 (1992).
Lofblom et al., "Non-immunoglobulin based protein scaffolds.", Current Opinion in Biotechnology, 22(6), 843-848 (2011).
Maynard et al., "Antibody Engineering", Rev. Biomed. Eng. 2:339-76 (2000).
Ronner et al., "Biofilm Development and Sanitizer Inactivation of Listeria monocytogenes and *Salmonella typhimurium* on Stainless Steel and Buna-n Rubber", Food Prot 56:750-8 (1993).
North et al., "Plasma-Based Surface Modification of Polystyrene Microtiter Plates for Covalent Immobilization of Biomolecules" ACS Applied materials & interfaces 2(10) 2884-2891 (2010).
Tsougeni et al., "Direct Covalent Biomolecule Immobilization on Plasma-Nanotextured Chemically Stable Substrates" ACS Appl Mater Interfaces 7(27) 14670-14681 (2015).
Xiaoshuai et al., "Immobilized heparin and its anti-coagulation effect on polysulfone membrane surface" Journal of Biomaterials Science, Polymer Edition 24(15) 1707-1720 (2013).
Paslaru et al., "Immunoglobulin G immobilization on PVDF surface" Colloids Surf B Biointerfaces, 1(115) 139-149 (2014).
Zhao et al., "Modification of polyethersulfone membranes—A review of methods." Progress in Materials Science 58(1) 76-150 (2013).
International Search Report cited in PCT/US2017/032928 dated Nov. 23, 2017.
Shen et al., "The immobilization of basic fibroblast growth factor on plasma-treated poly (lactide-co-glycolide)." Biomaterials 29.15 (2008): 2388-2399.
Stoleru et al., "Plasma-activated fibrinogen coatings onto poly (vinylidene fluoride) surface for improving biocompatibility with tissues." Journal of Bioactive and Compatible Polymers (2015) pp. 1-18.

(56) References Cited

OTHER PUBLICATIONS

Didar et al., "Opsonin-coated hollow fibers for pathogen removal from flowing blood," 18th International Conference On Miniaturized Systems for Chemistry and Life Sciences: 1509-1511 (Oct. 26-30, 2014).

Gancarz et al., "Modification of polysulfone membranes 1. CO2 plasma treatment." Eur Polymer Journal 35(8): 1419-1428 (Aug. 1999).

Wavhal et al., "Modification of porous poly(ether sulfone) membranes by low-temperature CO2-plasma treatment." Journal of Polymer Science Part B: Polymer Physics 40: 2473-2488 (2002).

Pal et al., "Evaluation of surface roughness of a plasma treated polymeric membrane by wavelet analysis and quantification of its enhanced performance," Applied Surface Science 255: 2504-2511 (2008).

Wavhal et al., "Hydrophilic Surface Modification of Microporous Polymer Membranes Using A Variety of Low-Temperature Plasma Treatments," Materials Research Society (MRS) Proceedings 752: AA3.1; available on the world wide web at dx.doi.org/10.1557/PROC-752-AA3.1 (2002).

\* cited by examiner

Spectrum Filter Sample

United States Patent US 11,919,971 B2

SEQUENCE LISTING

```
<160> NUMBER OF SEQ ID NOS: 56

<210> SEQ ID NO 1
<211> LENGTH: 248
<212> TYPE: PRT
<213> ORGANISM: Homo sapiens

<400> SEQUENCE: 1

Met Ser Leu Phe Pro Ser Leu Pro Leu Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
        35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205
```

Asn Glu Gly Glu Pro Asn Asn Ala Gly Ser Asp Glu Asp Cys Val Leu
        210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245

<210> SEQ ID NO 2
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Thr Val Thr Cys Glu Asp Ala Gln Lys Thr Cys Pro Ala Val Ile
1               5                   10                  15

Ala Cys Ser Ser Pro Gly Ile Asn Gly Phe Pro Gly Lys Asp Gly Arg
            20                  25                  30

Asp Gly Thr Lys Gly Glu Lys Gly Glu Pro Gly Gln Gly Leu Arg Gly
        35                  40                  45

Leu Gln Gly Pro Pro Gly Lys Leu Gly Pro Pro Gly Asn Pro Gly Pro
    50                  55                  60

Ser Gly Ser Pro Gly Pro Lys Gly Gln Lys Gly Asp Pro Gly Lys Ser
65                  70                  75                  80

Pro Asp Gly Asp Ser Ser Leu Ala Ala Ser Glu Arg Lys Ala Leu Gln
                85                  90                  95

Thr Glu Met Ala Arg Ile Lys Lys Trp Leu Thr Phe Ser Leu Gly Lys
            100                 105                 110

Gln Val Gly Asn Lys Phe Phe Leu Thr Asn Gly Glu Ile Met Thr Phe
        115                 120                 125

Glu Lys Val Lys Ala Leu Cys Val Lys Phe Gln Ala Ser Val Ala Thr
    130                 135                 140

Pro Arg Asn Ala Ala Glu Asn Gly Ala Ile Gln Asn Leu Ile Lys Glu
145                 150                 155                 160

Glu Ala Phe Leu Gly Ile Thr Asp Glu Lys Thr Glu Gly Gln Phe Val
                165                 170                 175

Asp Leu Thr Gly Asn Arg Leu Thr Tyr Thr Asn Trp Asn Glu Gly Glu
            180                 185                 190

Pro Asn Asn Ala Gly Ser Asp Glu Asp Cys Val Leu Leu Leu Lys Asn
        195                 200                 205

Gly Gln Trp Asn Asp Val Pro Cys Ser Thr Ser His Leu Ala Val Cys
    210                 215                 220

Glu Phe Pro Ile
225

<210> SEQ ID NO 3
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Ala Ser Glu Arg Lys Ala Leu Gln Thr Glu Met Ala Arg Ile Lys
1               5                   10                  15

```
Lys Trp Leu Thr Phe Ser Leu Gly Lys Gln Val Gly Asn Lys Phe Phe
            20                  25                  30

Leu Thr Asn Gly Glu Ile Met Thr Phe Glu Lys Val Lys Ala Leu Cys
            35                  40                  45

Val Lys Phe Gln Ala Ser Val Ala Thr Pro Arg Asn Ala Ala Glu Asn
 50                  55                  60

Gly Ala Ile Gln Asn Leu Ile Lys Glu Glu Ala Phe Leu Gly Ile Thr
 65                  70                  75                  80

Asp Glu Lys Thr Glu Gly Gln Phe Val Asp Leu Thr Gly Asn Arg Leu
                85                  90                  95

Thr Tyr Thr Asn Trp Asn Glu Gly Glu Pro Asn Asn Ala Gly Ser Asp
            100                 105                 110

Glu Asp Cys Val Leu Leu Lys Asn Gly Gln Trp Asn Asp Val Pro
            115                 120                 125

Cys Ser Thr Ser His Leu Ala Val Cys Glu Phe Pro Ile
            130                 135                 140
```

<210> SEQ ID NO 4
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Val Gly Asn Lys Phe Phe Leu Thr Asn Gly Glu Ile Met Thr Phe Glu
 1               5                  10                  15

Lys Val Lys Ala Leu Cys Val Lys Phe Gln Ala Ser Val Ala Thr Pro
            20                  25                  30

Arg Asn Ala Ala Glu Asn Gly Ala Ile Gln Asn Leu Ile Lys Glu Glu
            35                  40                  45

Ala Phe Leu Gly Ile Thr Asp Glu Lys Thr Glu Gly Gln Phe Val Asp
 50                  55                  60

Leu Thr Gly Asn Arg Leu Thr Tyr Thr Asn Trp Asn Glu Gly Glu Pro
 65                  70                  75                  80

Asn Asn Ala Gly Ser Asp Glu Asp Cys Val Leu Leu Lys Asn Gly
                85                  90                  95

Gln Trp Asn Asp Val Pro Cys Ser Thr Ser His Leu Ala Val Cys Glu
            100                 105                 110

Phe Pro Ile
            115
```

<210> SEQ ID NO 5
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Pro Asp Gly Asp Ser Ser Leu Ala Ala Ser Glu Arg Lys Ala Leu Gln
 1               5                  10                  15

Thr Glu Met Ala Arg Ile Lys Lys Trp Leu Thr Phe Ser Leu Gly Lys
            20                  25                  30

Gln Val Gly Asn Lys Phe Phe Leu Thr Asn Gly Glu Ile Met Thr Phe
            35                  40                  45
```

```
Glu Lys Val Lys Ala Leu Cys Val Lys Phe Gln Ala Ser Val Ala Thr
            50                  55                  60
Pro Arg Asn Ala Ala Glu Asn Gly Ala Ile Gln Asn Leu Ile Lys Glu
65                  70                  75                  80
Glu Ala Phe Leu Gly Ile Thr Asp Glu Lys Thr Glu Gly Gln Phe Val
                85                  90                  95
Asp Leu Thr Gly Asn Arg Leu Thr Tyr Thr Asn Trp Asn Glu Gly Glu
                100                 105                 110
Pro Asn Asn Ala Gly Ser Asp Glu Asp Cys Val Leu Leu Leu Lys Asn
            115                 120                 125
Gly Gln Trp Asn Asp Val Pro Cys Ser Thr Ser His Leu Ala Val Cys
            130                 135                 140
Glu Phe Pro Ile
145

<210> SEQ ID NO 6
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Pro Lys Ser Ser Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
                20                  25                  30
Lys Asp Thr Leu Met Ile Ser Arg Thr Pro Glu Val Thr Cys Val Val
            35                  40                  45
Val Asp Val Ser His Glu Asp Pro Glu Val Lys Phe Asn Trp Tyr Val
        50                  55                  60
Asp Gly Val Glu Val His Asn Ala Lys Thr Lys Pro Arg Glu Glu Gln
65                  70                  75                  80
Tyr Asp Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
                100                 105                 110
Leu Pro Ala Pro Ile Glu Lys Thr Ile Ser Lys Ala Lys Gly Gln Pro
            115                 120                 125
Arg Glu Pro Gln Val Tyr Thr Leu Pro Pro Ser Arg Asp Glu Leu Thr
            130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
                180                 185                 190
Ser Lys Leu Thr Val Asp Lys Ser Arg Trp Gln Gln Gly Asn Val Phe
            195                 200                 205
Ser Cys Ser Val Met His Glu Ala Leu His Asn His Tyr Thr Gln Lys
            210                 215                 220
Ser Leu Ser Leu Ser Pro Gly Ala Pro Asp Gly Asp Ser Ser Leu Ala
225                 230                 235                 240
Ala Ser Glu Arg Lys Ala Leu Gln Thr Glu Met Ala Arg Ile Lys Lys
```

```
                  245                 250                 255
Trp Leu Thr Phe Ser Leu Gly Lys Gln Val Gly Asn Lys Phe Phe Leu
            260                 265                 270
Thr Asn Gly Glu Ile Met Thr Phe Glu Lys Val Lys Ala Leu Cys Val
        275                 280                 285
Lys Phe Gln Ala Ser Val Ala Thr Pro Arg Asn Ala Ala Glu Asn Gly
    290                 295                 300
Ala Ile Gln Asn Leu Ile Lys Glu Ala Phe Leu Gly Ile Thr Asp
305                 310                 315                 320
Glu Lys Thr Glu Gly Gln Phe Val Asp Leu Thr Gly Asn Arg Leu Thr
                325                 330                 335
Tyr Thr Asn Trp Asn Glu Gly Glu Pro Asn Asn Ala Gly Ser Asp Glu
            340                 345                 350
Asp Cys Val Leu Leu Leu Lys Asn Gly Gln Trp Asn Asp Val Pro Cys
        355                 360                 365
Ser Thr Ser His Leu Ala Val Cys Glu Phe Pro Ile
    370                 375                 380

<210> SEQ ID NO 7
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Lys Thr Glu Pro Lys Ser Ser Asp Lys Thr His Thr Cys Pro Pro
1               5                   10                  15
Cys Pro Ala Pro Glu Leu Leu Gly Gly Pro Ser Val Phe Leu Phe Pro
            20                  25                  30
Pro Lys Pro Lys Asp Thr Leu Met Ile Ser Arg Thr Pro Glu Val Thr
        35                  40                  45
Cys Val Val Val Asp Val Ser His Glu Asp Pro Glu Val Lys Phe Asn
    50                  55                  60
Trp Tyr Val Asp Gly Val Glu Val His Asn Ala Lys Thr Lys Pro Arg
65                  70                  75                  80
Glu Glu Gln Tyr Asp Ser Thr Tyr Arg Val Val Ser Val Leu Thr Val
                85                  90                  95
Leu His Gln Asp Trp Leu Asn Gly Lys Glu Tyr Lys Cys Lys Val Ser
            100                 105                 110
Asn Lys Ala Leu Pro Ala Pro Ile Glu Lys Thr Ile Ser Lys Ala Lys
        115                 120                 125
Gly Gln Pro Arg Glu Pro Gln Val Tyr Thr Leu Pro Pro Ser Arg Asp
    130                 135                 140
Glu Leu Thr Lys Asn Gln Val Ser Leu Thr Cys Leu Val Lys Gly Phe
145                 150                 155                 160
Tyr Pro Ser Asp Ile Ala Val Glu Trp Glu Ser Asn Gly Gln Pro Glu
                165                 170                 175
Asn Asn Tyr Lys Thr Thr Pro Pro Val Leu Asp Ser Asp Gly Ser Phe
            180                 185                 190
Phe Leu Tyr Ser Lys Leu Thr Val Asp Lys Ser Arg Trp Gln Gln Gly
        195                 200                 205
Asn Val Phe Ser Cys Ser Val Met His Glu Ala Leu His Asn His Tyr
    210                 215                 220
```

-continued

```
Thr Gln Lys Ser Leu Ser Leu Ser Pro Gly Ala Pro Asp Gly Asp Ser
225                 230                 235                 240

Ser Leu Ala Ala Ser Glu Arg Lys Ala Leu Gln Thr Glu Met Ala Arg
            245                 250                 255

Ile Lys Lys Trp Leu Thr Phe Ser Leu Gly Lys Gln Val Gly Asn Lys
            260                 265                 270

Phe Phe Leu Thr Asn Gly Glu Ile Met Thr Phe Glu Lys Val Lys Ala
        275                 280                 285

Leu Cys Val Lys Phe Gln Ala Ser Val Ala Thr Pro Arg Asn Ala Ala
    290                 295                 300

Glu Asn Gly Ala Ile Gln Asn Leu Ile Lys Glu Ala Phe Leu Gly
305                 310                 315                 320

Ile Thr Asp Glu Lys Thr Glu Gly Gln Phe Val Asp Leu Thr Gly Asn
                325                 330                 335

Arg Leu Thr Tyr Thr Asn Trp Asn Glu Gly Glu Pro Asn Asn Ala Gly
            340                 345                 350

Ser Asp Glu Asp Cys Val Leu Leu Leu Lys Asn Gly Gln Trp Asn Asp
        355                 360                 365

Val Pro Cys Ser Thr Ser His Leu Ala Val Cys Glu Phe Pro Ile
    370                 375                 380
```

<210> SEQ ID NO 8
<211> LENGTH: 351
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210                 215                 220
Ser Leu Ser Leu Ser Pro Gly Ala Thr Ser Lys Gln Val Gly Asn Lys
225                 230                 235                 240
Phe Phe Leu Thr Asn Gly Glu Ile Met Thr Phe Glu Lys Val Lys Ala
                245                 250                 255
Leu Cys Val Lys Phe Gln Ala Ser Val Ala Thr Pro Arg Asn Ala Ala
            260                 265                 270
Glu Asn Gly Ala Ile Gln Asn Leu Ile Lys Glu Ala Phe Leu Gly
        275                 280                 285
Ile Thr Asp Glu Lys Thr Glu Gly Gln Phe Val Asp Leu Thr Gly Asn
    290                 295                 300
Arg Leu Thr Tyr Thr Asn Trp Asn Gly Glu Pro Asn Asn Ala Gly
305                 310                 315                 320
Ser Asp Glu Asp Cys Val Leu Leu Leu Lys Asn Gly Gln Trp Asn Asp
            325                 330                 335
Val Pro Cys Ser Thr Ser His Leu Ala Val Cys Glu Phe Pro Ile
            340                 345                 350
```

<210> SEQ ID NO 9

<400> SEQUENCE: 9

000

<210> SEQ ID NO 10
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Asp
1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 11

Glu Xaa Asn
1

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Glu Gly Glu Pro Asn Asn Ala Gly Ser

```
<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ser Asp Glu Asp Cys Val Leu Leu
1               5

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Leu Leu Lys Asn Gly Gln Trp Asn Asp Val Pro Cys Ser Thr
1               5                   10                  15

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
            20                  25                  30

Gln

<210> SEQ ID NO 16
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Pro Gly Gln Gly Leu Arg Gly Leu Gln Gly Pro Pro Gly Lys Leu
1               5                   10                  15

Gly Pro Pro Gly Asn Pro Gly Pro Ser Gly Ser
            20                  25

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Lys Leu Gly
1
```

```
<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Pro Pro Gly Lys Leu Gly Pro Pro Gly Asn
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Gly Leu Gln Gly Pro Pro Gly Lys Leu
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Lys Leu Gly Pro Pro Gly Asn Pro Gly Pro Ser Gly Ser
1               5                   10

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Leu Arg Gly Leu Gln Gly Pro Pro Gly Lys Leu Gly Pro Pro Gly
1               5                   10                  15

Asn Pro Gly Pro
            20

<210> SEQ ID NO 22
<211> LENGTH: 170
<212> TYPE: PRT
<213> ORGANISM: Homo sapiens

<400> SEQUENCE: 22

Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
                20                  25                  30

Gln Val Gly Asn Lys Phe Phe Leu Thr Asn Gly Glu Ile Met Thr Phe
            35                  40                  45

Glu Lys Val Lys Ala Leu Cys Val Lys Phe Gln Ala Ser Val Ala Thr
        50                  55                  60
```

```
Pro Arg Asn Ala Ala Glu Asn Gly Ala Ile Gln Asn Leu Ile Lys Glu
 65                  70                  75                  80

Glu Ala Phe Leu Gly Ile Thr Asp Glu Lys Thr Glu Gly Gln Phe Val
                 85                  90                  95

Asp Leu Thr Gly Asn Arg Leu Tyr Thr Asn Trp Asn Glu Gly Glu
            100                 105                 110

Pro Asn Asn Ala Gly Ser Asp Glu Asp Cys Val Leu Leu Lys Asn
            115                 120                 125

Gly Gln Trp Asn Asp Val Pro Cys Ser Thr Ser His Leu Ala Val Cys
        130                 135                 140

Glu Phe Pro Ile Gly Ser Ala Trp Trp Ser Tyr Trp Trp Thr Gln Trp
145                 150                 155                 160

Ala Ser Glu Leu Gly Ser Pro Gly Ser Pro
                165                 170

<210> SEQ ID NO 23
<211> LENGTH: 149
<212> TYPE: PRT
<213> ORGANISM: Marsupenaeus japonicus

<400> SEQUENCE: 23

Ala Thr Cys Ala Thr Phe Cys Thr Ala Gln Val Asn Pro Cys Pro Asn
1               5                   10                  15

Gly Tyr Ile Val Phe Trp Met Asp Ser Val Thr Pro Val Cys Leu Lys
            20                  25                  30

Phe Ala Met Tyr Gly Lys Gly Thr Trp Thr Asn Leu Arg Met Met Cys
        35                  40                  45

Gln Ala Glu Gly Ala Asp Leu Ala Lys Leu Asp Gly Asn Leu His Tyr
    50                  55                  60

Gln Val Ile Gln Tyr Ile Asn Asn Gln Arg Pro Asp Leu Gln Asp Glu
65                  70                  75                  80

Ala Phe Trp Ile Gly Gly Thr Asp Ala Ala Ser Glu Gly Tyr Trp Val
                85                  90                  95

Trp Ala Met Asp Gly Thr Gln Met Asp Met Ser Asn Pro Pro Trp Tyr
            100                 105                 110

Pro Gly Gln Pro Asn Arg Gly Thr Ile Ala Asn Tyr Ala Cys Leu Tyr
        115                 120                 125

Thr Pro Asp Phe Met Phe His Ser Cys Asp Asn Asp Arg Lys Ile Tyr
    130                 135                 140

Ala Ile Cys Gln Ile
145

<210> SEQ ID NO 24
<211> LENGTH: 139
<212> TYPE: PRT
<213> ORGANISM: Homo sapiens

<400> SEQUENCE: 24

Glu Arg Leu Cys His Pro Cys Pro Trp Glu Trp Thr Phe Phe Gln Gly
1               5                   10                  15

Asn Cys Tyr Phe Met Ser Asn Ser Gln Arg Asn Trp His Asp Ser Ile
            20                  25                  30

Thr Ala Cys Lys Glu Val Gly Ala Gln Leu Val Val Ile Lys Ser Ala
        35                  40                  45

Glu Glu Gln Asn Phe Leu Gln Leu Gln Ser Ser Arg Ser Asn Arg Phe
    50                  55                  60
```

Thr Trp Met Gly Leu Ser Asp Leu Asn Gln Glu Gly Thr Trp Gln Trp
65                  70                  75                  80

Val Asp Gly Ser Pro Leu Leu Pro Ser Phe Lys Gln Tyr Trp Asn Arg
                85                  90                  95

Gly Glu Pro Asn Asn Val Gly Glu Asp Cys Ala Glu Phe Ser Gly
            100                 105                 110

Asn Gly Trp Asn Asp Asp Lys Cys Asn Leu Ala Lys Phe Trp Ile Cys
            115                 120                 125

Lys Lys Ser Ala Ala Ser Cys Ser Arg Asp Glu
        130                 135

<210> SEQ ID NO 25
<211> LENGTH: 138
<212> TYPE: PRT
<213> ORGANISM: Homo sapiens

<400> SEQUENCE: 25

Glu Arg Leu Cys Arg His Cys Pro Lys Asp Trp Thr Phe Phe Gln Gly
1               5                   10                  15

Asn Cys Tyr Phe Met Ser Asn Ser Gln Arg Asn Trp His Asp Ser Val
            20                  25                  30

Thr Ala Cys Gln Glu Val Arg Ala Gln Leu Val Val Ile Lys Thr Ala
        35                  40                  45

Glu Glu Gln Asn Phe Leu Gln Leu Gln Thr Ser Arg Ser Asn Arg Phe
    50                  55                  60

Ser Trp Met Gly Leu Ser Asp Leu Asn Gln Glu Gly Thr Trp Gln Trp
65                  70                  75                  80

Val Asp Gly Ser Pro Leu Ser Pro Ser Phe Gln Arg Tyr Trp Asn Ser
                85                  90                  95

Gly Glu Pro Asn Asn Ser Gly Asn Glu Asp Cys Ala Glu Phe Ser Gly
            100                 105                 110

Ser Gly Trp Asn Asp Asn Arg Cys Asp Val Asp Asn Tyr Trp Ile Cys
            115                 120                 125

Lys Lys Pro Ala Ala Cys Phe Arg Asp Glu
        130                 135

<210> SEQ ID NO 26
<211> LENGTH: 356
<212> TYPE: PRT
<213> ORGANISM: Homo sapiens

<400> SEQUENCE: 26

Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
            20                  25                  30

Val Ser Ala Val Glu Val Glu Ile His Ala Gly Gly Leu Asn Leu Glu
        35                  40                  45

Pro Phe Leu Lys Arg Val Asp Ala Asp Ala Asp Pro Arg Gln Tyr Ala
    50                  55                  60

Asp Thr Val Lys Ala Leu Arg Val Arg Arg Leu Thr Val Gly Ala Ala
65                  70                  75                  80

Gln Val Pro Ala Gln Leu Leu Val Gly Ala Leu Arg Val Leu Ala Tyr
                85                  90                  95

Ser Arg Leu Lys Glu Leu Thr Leu Glu Asp Leu Lys Ile Thr Gly Thr
            100                 105                 110

Met Pro Pro Leu Pro Leu Glu Ala Thr Gly Leu Ala Leu Ser Ser Leu
                115                 120                 125

Arg Leu Arg Asn Val Ser Trp Ala Thr Gly Arg Ser Trp Leu Ala Glu
130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
                180                 185                 190

Leu Met Ala Ala Leu Cys Pro His Lys Phe Pro Ala Ile Gln Asn Leu
                195                 200                 205

Ala Leu Arg Asn Thr Gly Met Glu Thr Pro Thr Gly Val Cys Ala Ala
210                 215                 220

Leu Ala Ala Ala Gly Val Gln Pro His Ser Leu Asp Leu Ser His Asn
225                 230                 235                 240

Ser Leu Arg Ala Thr Val Asn Pro Ser Ala Pro Arg Cys Met Trp Ser
                245                 250                 255

Ser Ala Leu Asn Ser Leu Asn Leu Ser Phe Ala Gly Leu Glu Gln Val
                260                 265                 270

Pro Lys Gly Leu Pro Ala Lys Leu Arg Val Leu Asp Leu Ser Cys Asn
                275                 280                 285

Arg Leu Asn Arg Ala Pro Gln Pro Asp Glu Leu Pro Glu Val Asp Asn
290                 295                 300

Leu Thr Leu Asp Gly Asn Pro Phe Leu Val Pro Gly Thr Ala Leu Pro
305                 310                 315                 320

His Glu Gly Ser Met Asn Ser Gly Val Val Pro Ala Cys Ala Arg Ser
                325                 330                 335

Thr Leu Ser Val Gly Val Ser Gly Thr Leu Val Leu Leu Gln Gly Ala
                340                 345                 350

Arg Gly Phe Ala
        355

<210> SEQ ID NO 27
<211> LENGTH: 166
<212> TYPE: PRT
<213> ORGANISM: Mus musculus

<400> SEQUENCE: 27

Cys Ser Phe Ile Val Pro Arg Ser Glu Trp Arg Ala Leu Pro Ser Glu
1               5                   10                  15

Cys Ser Ser Arg Leu Gly His Pro Val Arg Tyr Val Val Ile Ser His
                20                  25                  30

Thr Ala Gly Ser Phe Cys Asn Ser Pro Asp Ser Cys Glu Gln Gln Ala
            35                  40                  45

Arg Asn Val Gln His Tyr His Lys Asn Glu Leu Gly Trp Cys Asp Val
        50                  55                  60

Ala Tyr Asn Phe Leu Ile Gly Glu Asp Gly His Val Tyr Glu Gly Arg
65                  70                  75                  80

Gly Trp Asn Ile Lys Gly Asp His Thr Gly Pro Ile Trp Asn Pro Met
                85                  90                  95

Ser Ile Gly Ile Thr Phe Met Gly Asn Phe Met Asp Arg Val Pro Ala
                100                 105                 110

Lys Arg Ala Leu Arg Ala Ala Leu Asn Leu Leu Glu Cys Gly Val Ser

```
            115                 120                 125

Arg Gly Phe Leu Arg Ser Asn Tyr Glu Val Lys Gly His Arg Asp Val
            130                 135                 140

Gln Ser Thr Leu Ser Pro Gly Asp Gln Leu Tyr Gln Val Ile Gln Ser
145                 150                 155                 160

Trp Glu His Tyr Arg Glu
                165

<210> SEQ ID NO 28
<211> LENGTH: 171
<212> TYPE: PRT
<213> ORGANISM: Holotrichia diomphalia

<400> SEQUENCE: 28

Pro Ser Pro Gly Cys Pro Thr Ile Val Ser Lys Asn Arg Trp Gly Gly
1               5                   10                  15

Gln Gln Ala Ser Gln Val Gln Tyr Thr Val Lys Pro Leu Lys Tyr Val
            20                  25                  30

Ile Ile His His Thr Ser Thr Pro Thr Cys Thr Asn Glu Asp Asp Cys
            35                  40                  45

Ser Arg Arg Leu Val Asn Ile Gln Asp Tyr His Met Asn Arg Leu Asp
        50                  55                  60

Phe Asp Asp Ile Gly Tyr Asn Phe Met Ile Gly Gly Asp Gly Gln Ile
65                  70                  75                  80

Tyr Glu Gly Ala Gly Trp His Lys Glu Gly Ala His Ala Arg Gly Trp
                85                  90                  95

Asn Ser Lys Ser Leu Gly Ile Gly Phe Ile Gly Asp Phe Gln Thr Asn
            100                 105                 110

Leu Pro Ser Ser Lys Gln Leu Asp Ala Gly Lys Lys Phe Leu Glu Cys
            115                 120                 125

Ala Val Glu Lys Gly Glu Ile Glu Asp Thr Tyr Lys Leu Ile Gly Ala
            130                 135                 140

Arg Thr Val Arg Pro Thr Asp Ser Pro Gly Thr Leu Leu Phe Arg Glu
145                 150                 155                 160

Ile Gln Thr Trp Arg Gly Phe Thr Arg Asn Pro
                165                 170

<210> SEQ ID NO 29
<211> LENGTH: 356
<212> TYPE: PRT
<213> ORGANISM: Homo sapiens

<400> SEQUENCE: 29

Asp Ser Ser Trp Asn Lys Thr Gln Ala Lys Gln Val Ser Glu Gly Leu
1               5                   10                  15

Gln Tyr Leu Phe Glu Asn Ile Ser Gln Leu Thr Glu Lys Gly Leu Pro
            20                  25                  30

Thr Asp Val Ser Thr Thr Val Ser Arg Lys Ala Trp Gly Ala Glu Ala
            35                  40                  45

Val Gly Cys Ser Ile Gln Leu Thr Thr Pro Val Asn Val Leu Val Ile
        50                  55                  60

His His Val Pro Gly Leu Glu Cys His Asp Thr Val Cys Ser Gln
65                  70                  75                  80

Arg Leu Arg Glu Leu Gln Ala His His Val His Asn Asn Ser Gly Cys
                85                  90                  95

Asp Val Ala Tyr Asn Phe Leu Val Gly Asp Asp Gly Arg Val Tyr Glu
```

```
            100                 105                 110
Gly Val Gly Trp Asn Ile Gln Gly Val His Thr Gln Gly Tyr Asn Asn
        115                 120                 125

Ile Ser Leu Gly Phe Ala Phe Phe Gly Thr Lys Lys Gly His Ser Pro
130                 135                 140

Ser Pro Ala Ala Leu Ser Ala Met Glu Asn Leu Ile Thr Tyr Ala Val
145                 150                 155                 160

Gln Lys Gly His Leu Ser Ser Ser Tyr Val Gln Pro Leu Leu Gly Lys
                165                 170                 175

Gly Glu Asn Cys Leu Ala Pro Arg Gln Lys Thr Ser Leu Lys Lys Ala
            180                 185                 190

Cys Pro Gly Val Val Pro Arg Ser Val Trp Gly Ala Arg Glu Thr His
        195                 200                 205

Cys Pro Arg Met Thr Leu Pro Ala Lys Tyr Gly Ile Ile Ile His Thr
    210                 215                 220

Ala Gly Arg Thr Cys Asn Ile Ser Asp Glu Cys Arg Leu Leu Val Arg
225                 230                 235                 240

Asp Ile Gln Ser Phe Tyr Ile Asp Arg Leu Lys Ser Cys Asp Ile Gly
                245                 250                 255

Tyr Asn Phe Leu Val Gly Gln Asp Gly Ala Ile Tyr Glu Gly Val Gly
            260                 265                 270

Trp Asn Val Gln Gly Ser Ser Thr Pro Gly Tyr Asp Asp Ile Ala Leu
        275                 280                 285

Gly Ile Thr Phe Met Gly Thr Phe Thr Gly Ile Pro Pro Asn Ala Ala
    290                 295                 300

Ala Leu Glu Ala Ala Gln Asp Leu Ile Gln Cys Ala Met Val Lys Gly
305                 310                 315                 320

Tyr Leu Thr Pro Asn Tyr Leu Leu Val Gly His Ser Asp Val Ala Arg
                325                 330                 335

Thr Leu Ser Pro Gly Gln Ala Leu Tyr Asn Ile Ile Ser Thr Trp Pro
            340                 345                 350

His Phe Lys His
        355

<210> SEQ ID NO 30
<211> LENGTH: 472
<212> TYPE: PRT
<213> ORGANISM: Manduca sexta

<400> SEQUENCE: 30

Pro Ser Pro Cys Leu Glu Val Pro Asp Ala Lys Leu Glu Ala Ile Tyr
1               5                   10                  15

Pro Lys Gly Leu Arg Val Ser Ile Pro Asp Asp Gly Tyr Thr Leu Phe
            20                  25                  30

Ala Phe His Gly Lys Leu Asn Glu Glu Met Glu Gly Leu Glu Ala Gly
        35                  40                  45

His Trp Ser Arg Asp Ile Thr Lys Ala Lys Asn Gly Arg Trp Ile Phe
    50                  55                  60

Arg Asp Arg Asn Ala Lys Leu Lys Ile Gly Asp Lys Ile Tyr Phe Trp
65                  70                  75                  80

Thr Tyr Ile Leu Lys Asp Gly Leu Gly Tyr Arg Gln Asp Asn Gly Glu
                85                  90                  95

Trp Thr Val Thr Gly Tyr Val Asn Glu Asp Gly Glu Pro Leu Asp Ala
            100                 105                 110
```

```
Asn Phe Glu Pro Arg Ser Thr Ala Ser Thr Ala Ala Pro Pro Gln Ala
            115                 120                 125

Gly Ala Gly Gln Ala Pro Gly Pro Ser Tyr Pro Cys Glu Leu Ser Val
        130                 135                 140

Ser Glu Val Ser Val Pro Gly Phe Val Cys Lys Gly Gln Met Leu Phe
145                 150                 155                 160

Glu Asp Asn Phe Asn Lys Pro Leu Ala Asp Gly Arg Ile Trp Thr Pro
                165                 170                 175

Glu Ile Met Phe Pro Gly Glu Pro Asp Tyr Pro Phe Asn Val Tyr Met
            180                 185                 190

Lys Glu Thr Asp Asn Leu His Val Gly Asn Gly Asn Leu Val Ile Lys
        195                 200                 205

Pro Met Pro Leu Val Thr Ala Phe Gly Glu Asp Ala Ile Trp Lys Thr
    210                 215                 220

Leu Asp Leu Ser Asp Arg Cys Thr Gly Leu Leu Gly Thr Ala Gln Cys
225                 230                 235                 240

Lys Arg Asp Pro Ser Asp Ala Ile Ile Val Pro Pro Ile Val Thr Ala
                245                 250                 255

Lys Ile Asn Thr Lys Lys Thr Phe Ala Phe Lys Tyr Gly Arg Val Glu
            260                 265                 270

Ile Ser Ala Lys Met Pro Arg Gly Asp Trp Leu Val Pro Leu Ile Gln
        275                 280                 285

Leu Glu Pro Val Asn Lys Asn Tyr Gly Ile Arg Asn Tyr Val Ser Gly
    290                 295                 300

Leu Leu Arg Val Ala Cys Val Lys Gly Asn Thr Glu Tyr Ile Lys Thr
305                 310                 315                 320

Leu Val Gly Gly Pro Ile Met Ser Glu Ala Glu Pro Tyr Arg Thr Ala
                325                 330                 335

Asn Leu Lys Glu Phe Ile Ser Asn Glu Pro Trp Thr Asn Glu Phe His
            340                 345                 350

Asn Tyr Thr Leu Glu Trp Ser Pro Asp Ala Ile Thr Met Ala Val Asp
        355                 360                 365

Gly Ile Val Tyr Gly Arg Val Thr Ala Pro Ala Gly Gly Phe Tyr Lys
    370                 375                 380

Glu Ala Asn Glu Gln Asn Val Glu Ala Ala Arg Trp Ile Gln Gly
385                 390                 395                 400

Ser Asn Ile Ala Pro Phe Asp Met Phe Tyr Ile Ser Leu Gly Met
                405                 410                 415

Asp Val Gly Gly Val His Glu Phe Pro Asp Glu Ala Ile Asn Lys Pro
            420                 425                 430

Trp Lys Asn Thr Ala Thr Lys Ala Met Val Asn Phe Trp Asn Ala Arg
        435                 440                 445

Ser Gln Trp Asn Pro Thr Trp Leu Glu Ser Glu Lys Ala Leu Leu Val
    450                 455                 460

Asp Tyr Val Arg Val Tyr Ala Leu
465                 470

<210> SEQ ID NO 31
<211> LENGTH: 175
<212> TYPE: PRT
<213> ORGANISM: Homo sapiens

<400> SEQUENCE: 31

Gln Glu Thr Glu Asp Pro Ala Cys Cys Ser Pro Ile Val Pro Arg Asn
1               5                   10                  15
```

```
Glu Trp Lys Ala Leu Ala Ser Glu Cys Ala Gln His Leu Ser Leu Pro
            20                  25                  30

Leu Arg Tyr Val Val Ser His Thr Ala Gly Ser Ser Cys Asn Thr
        35                  40                  45

Pro Ala Ser Cys Gln Gln Ala Arg Asn Val Gln His Tyr His Met
 50                  55                  60

Lys Thr Leu Gly Trp Cys Asp Val Gly Tyr Asn Phe Leu Ile Gly Glu
 65                  70                  75                  80

Asp Gly Leu Val Tyr Glu Gly Arg Gly Trp Asn Phe Thr Gly Ala His
                 85                  90                  95

Ser Gly His Leu Trp Asn Pro Met Ser Ile Gly Ile Ser Phe Met Gly
            100                 105                 110

Asn Tyr Met Asp Arg Val Pro Thr Pro Gln Ala Ile Arg Ala Ala Gln
            115                 120                 125

Gly Leu Leu Ala Cys Gly Val Ala Gln Gly Ala Leu Arg Ser Asn Tyr
130                 135                 140

Val Leu Lys Gly His Arg Asp Val Gln Arg Thr Leu Ser Pro Gly Asn
145                 150                 155                 160

Gln Leu Tyr His Leu Ile Gln Asn Trp Pro His Tyr Arg Ser Pro
                165                 170                 175

<210> SEQ ID NO 32
<211> LENGTH: 164
<212> TYPE: PRT
<213> ORGANISM: Homo sapiens

<400> SEQUENCE: 32

Cys Pro Asn Ile Ile Lys Arg Ser Ala Trp Glu Ala Arg Glu Thr His
1               5                  10                  15

Cys Pro Lys Met Asn Leu Pro Ala Lys Tyr Val Ile Ile His Thr
            20                  25                  30

Ala Gly Thr Ser Cys Thr Val Ser Thr Asp Cys Gln Thr Val Val Arg
        35                  40                  45

Asn Ile Gln Ser Phe His Met Asp Thr Arg Asn Phe Cys Asp Ile Gly
 50                  55                  60

Tyr His Phe Leu Val Gly Gln Asp Gly Gly Val Tyr Glu Gly Val Gly
 65                  70                  75                  80

Trp His Ile Gln Gly Ser His Thr Tyr Gly Phe Asn Asp Ile Ala Leu
                 85                  90                  95

Gly Ile Ala Phe Ile Gly Tyr Phe Val Glu Lys Pro Pro Asn Ala Ala
            100                 105                 110

Ala Leu Glu Ala Ala Gln Asp Leu Ile Gln Cys Ala Val Val Glu Gly
            115                 120                 125

Tyr Leu Thr Pro Asn Tyr Leu Leu Met Gly His Ser Asp Val Val Asn
130                 135                 140

Ile Leu Ser Pro Gly Gln Ala Leu Tyr Asn Ile Ile Ser Thr Trp Pro
145                 150                 155                 160

His Phe Lys His

<210> SEQ ID NO 33
<211> LENGTH: 169
<212> TYPE: PRT
<213> ORGANISM: Bos taurus

<400> SEQUENCE: 33
```

-continued

```
Gln Asp Cys Gly Ser Ile Val Ser Arg Gly Lys Trp Gly Ala Leu Ala
1               5                   10                  15

Ser Lys Cys Ser Gln Arg Leu Arg Gln Pro Val Arg Tyr Val Val
            20                  25                  30

Ser His Thr Ala Gly Ser Val Cys Asn Thr Pro Ala Ser Cys Gln Arg
            35                  40                  45

Gln Ala Gln Asn Val Gln Tyr Tyr His Val Arg Glu Arg Gly Trp Cys
        50                  55                  60

Asp Val Gly Tyr Asn Phe Leu Ile Gly Glu Asp Gly Leu Val Tyr Glu
65                  70                  75                  80

Gly Arg Gly Trp Asn Thr Leu Gly Ala His Ser Gly Pro Thr Trp Asn
            85                  90                  95

Pro Ile Ala Ile Gly Ile Ser Phe Met Gly Asn Tyr Met His Arg Val
            100                 105                 110

Pro Pro Ala Ser Ala Leu Arg Ala Ala Gln Ser Leu Leu Ala Cys Gly
            115                 120                 125

Ala Ala Arg Gly Tyr Leu Thr Pro Asn Tyr Glu Val Lys Gly His Arg
        130                 135                 140

Asp Val Gln Gln Thr Leu Ser Pro Gly Asp Glu Leu Tyr Lys Ile Ile
145                 150                 155                 160

Gln Gln Trp Pro His Tyr Arg Arg Val
                165

<210> SEQ ID NO 34
<211> LENGTH: 167
<212> TYPE: PRT
<213> ORGANISM: Homo sapiens

<400> SEQUENCE: 34

Cys Pro Ala Ile His Pro Arg Cys Arg Trp Gly Ala Ala Pro Tyr Arg
1               5                   10                  15

Gly Arg Pro Lys Leu Leu Gln Leu Pro Leu Gly Phe Leu Tyr Val His
            20                  25                  30

His Thr Tyr Val Pro Ala Pro Pro Cys Thr Asp Phe Thr Arg Cys Ala
            35                  40                  45

Ala Asn Met Arg Ser Met Gln Arg Tyr His Gln Asp Thr Gln Gly Trp
        50                  55                  60

Gly Asp Ile Gly Tyr Ser Phe Val Val Gly Ser Asp Gly Tyr Val Tyr
65                  70                  75                  80

Glu Gly Arg Gly Trp His Trp Val Gly Ala His Thr Leu Gly His Asn
            85                  90                  95

Ser Arg Gly Phe Gly Val Ala Ile Val Gly Asn Tyr Thr Ala Ala Leu
            100                 105                 110

Pro Thr Glu Ala Ala Leu Arg Thr Val Arg Asp Thr Leu Pro Ser Cys
            115                 120                 125

Ala Val Arg Ala Gly Leu Leu Arg Pro Asp Tyr Ala Leu Leu Gly His
        130                 135                 140

Arg Gln Leu Val Arg Thr Asp Cys Pro Gly Asp Ala Leu Phe Asp Leu
145                 150                 155                 160

Leu Arg Thr Trp Pro His Phe
                165

<210> SEQ ID NO 35
<211> LENGTH: 321
<212> TYPE: PRT
<213> ORGANISM: Homo sapiens
```

<400> SEQUENCE: 35

```
Pro Thr Ile Val Ser Arg Lys Glu Trp Gly Ala Arg Pro Leu Ala Cys
1               5                   10                  15
Arg Ala Leu Leu Thr Leu Pro Val Ala Tyr Ile Ile Thr Asp Gln Leu
                20                  25                  30
Pro Gly Met Gln Cys Gln Gln Ser Val Cys Ser Gln Met Leu Arg
            35                  40                  45
Gly Leu Gln Ser His Ser Val Tyr Thr Ile Gly Trp Cys Asp Val Ala
        50                  55                  60
Tyr Asn Phe Leu Val Gly Asp Asp Gly Arg Val Tyr Glu Gly Val Gly
65                  70                  75                  80
Trp Asn Ile Gln Gly Leu His Thr Gln Gly Tyr Asn Asn Ile Ser Leu
                85                  90                  95
Gly Ile Ala Phe Phe Gly Asn Lys Ile Gly Ser Ser Pro Ser Pro Ala
            100                 105                 110
Ala Leu Ser Ala Ala Glu Gly Leu Ile Ser Tyr Ala Ile Gln Lys Gly
        115                 120                 125
His Leu Ser Pro Arg Tyr Ile Gln Pro Leu Leu Leu Lys Glu Glu Thr
130                 135                 140
Cys Leu Asp Pro Gln His Pro Val Met Pro Arg Lys Val Cys Pro Asn
145                 150                 155                 160
Ile Ile Lys Arg Ser Ala Trp Glu Ala Arg Glu Thr His Cys Pro Lys
                165                 170                 175
Met Asn Leu Pro Ala Lys Tyr Val Ile Ile His Thr Ala Gly Thr
            180                 185                 190
Ser Cys Thr Val Ser Thr Asp Cys Gln Thr Val Val Arg Asn Ile Gln
        195                 200                 205
Ser Phe His Met Asp Thr Arg Asn Phe Cys Asp Ile Gly Tyr His Phe
210                 215                 220
Leu Val Gly Gln Asp Gly Gly Val Tyr Glu Gly Val Gly Trp His Ile
225                 230                 235                 240
Gln Gly Ser His Thr Tyr Gly Phe Asn Asp Ile Ala Leu Gly Ile Ala
                245                 250                 255
Phe Ile Gly Tyr Phe Val Glu Lys Pro Pro Asn Ala Ala Leu Glu
            260                 265                 270
Ala Ala Gln Asp Leu Ile Gln Cys Ala Val Val Glu Gly Tyr Leu Thr
        275                 280                 285
Pro Asn Tyr Leu Leu Met Gly His Ser Asp Val Asn Ile Leu Ser
290                 295                 300
Pro Gly Gln Ala Leu Tyr Asn Ile Ile Ser Thr Trp Pro His Phe Lys
305                 310                 315                 320
His
```

<210> SEQ ID NO 36
<211> LENGTH: 158
<212> TYPE: PRT
<213> ORGANISM: Marsupenaeus japonicus

<400> SEQUENCE: 36

```
Ala Trp Gly Gly Ala Thr Ala Thr Gly Pro Arg Lys Glu Ala Gly Asp
1               5                   10                  15
His Val Arg Asn Asp Val Cys Pro His Pro Phe Val Asp Ile Asn Gly
                20                  25                  30
```

```
Arg Cys Leu Phe Val Asp Asn Phe Ala His Leu Asn Trp Asp Ala Ala
             35                  40                  45

Arg Thr Phe Cys Gln Gly Phe Gln Gly Asp Leu Val Thr Leu Asp Glu
 50                  55                  60

Ala Asn Leu Leu Gly Tyr Ile Val Asp Phe Ile His Gln Glu Gly Leu
 65                  70                  75                  80

Thr Glu Arg Ser Tyr Trp Ile Gly Ser Asp Arg Thr Ser Glu Gly
                 85                  90                  95

Thr Trp Val Trp Thr Asp Gly Ser Ser Val Arg Met Gly Thr Pro Thr
                100                 105                 110

Trp Gly Val Asp Gly Glu Thr Gln Gln Pro Thr Gly Gly Thr Ser Glu
                115                 120                 125

Asn Cys Ile Gly Leu His Lys Asp Asn Phe Phe Phe Asn Asp Phe
                130                 135                 140

Ser Cys Asn Asn Glu Met Ser Leu Ile Cys Glu Phe Asn Met
145                 150                 155

<210> SEQ ID NO 37
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Arg Cys Gly Glu Gln Gly Ser Asn Met Glu Cys Pro Asn Asn Leu Cys
 1               5                  10                  15

Cys Ser Gln Tyr Gly Tyr Cys Gly Met Gly Gly Asp Tyr Cys Gly Lys
                 20                  25                  30

Gly Cys Gln Asn Gly Ala Cys Trp Thr Ser Lys Arg Cys Gly Ser Gln
                 35                  40                  45

Ala Gly Gly Ala Thr Cys Pro Asn Asn His Cys Cys Ser Gln Tyr Gly
 50                  55                  60

His Cys Gly Phe Gly Ala Glu Tyr Cys Gly Ala Gly Cys Gln Gly Gly
 65                  70                  75                  80

Pro Cys Arg Ala Asp Ile Lys Cys Gly Ser Gln Ser Gly Gly Lys Leu
                 85                  90                  95

Cys Pro Asn Asn Leu Cys Cys Ser Gln Trp Gly Phe Cys Gly Leu Gly
                100                 105                 110

Ser Glu Phe Cys Gly Gly Gly Cys Gln Ser Gly Ala Cys Ser Thr Asp
                115                 120                 125

Lys Pro Cys Gly Lys Asp Ala Gly Gly Arg Val Cys Thr Asn Asn Tyr
130                 135                 140

Cys Cys Ser Lys Trp Gly Ser Cys Gly Ile Gly Pro Gly Tyr Cys Gly
145                 150                 155                 160

Ala Gly Cys Gln Ser Gly Gly Cys Asp Ala Val Phe Ala Gly Ala Ile
                165                 170                 175

Thr Ala Asn Ser Thr Leu Leu Ala Glu
                180                 185

<210> SEQ ID NO 38
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 38

```
Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
210                 215                 220

Thr Gln Lys Ser Leu Ser Leu Ser Pro Gly Ala Pro Asp Gly Asp Ser
225                 230                 235                 240

Ser Leu Ala Ala Ser Glu Arg Lys Ala Leu Gln Thr Glu Met Ala Arg
                245                 250                 255

Ile Lys Lys Trp Leu Thr Phe Ser Leu Gly Lys Gln Val Gly Asn Lys
            260                 265                 270

Phe Phe Leu Thr Asn Gly Glu Ile Met Thr Phe Glu Lys Val Lys Ala
        275                 280                 285

Leu Cys Val Lys Phe Gln Ala Ser Val Ala Thr Pro Arg Asn Ala Ala
        290                 295                 300

Glu Asn Gly Ala Ile Gln Asn Leu Ile Lys Glu Glu Ala Phe Leu Gly
305                 310                 315                 320

Ile Thr Asp Glu Lys Thr Glu Gly Gln Phe Val Asp Leu Thr Gly Asn
                325                 330                 335

Arg Leu Thr Tyr Thr Asn Trp Asn Glu Gly Pro Asn Asn Ala Gly
            340                 345                 350

Ser Asp Glu Asp Cys Val Leu Leu Lys Asn Gly Gln Trp Asn Asp
        355                 360                 365

Val Pro Cys Ser Thr Ser His Leu Ala Val Cys Glu Phe Pro Ile Gly
        370                 375                 380

Ser Ala Trp Trp Ser Tyr Trp Trp Thr Gln Trp Ala Ser Glu Leu Gly
385                 390                 395                 400

Ser Pro Gly Ser Pro
```

<210> SEQ ID NO 39
<211> LENGTH: 384
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 39

```
Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Ala Thr Cys Ala Thr
225                 230                 235                 240

Phe Cys Thr Ala Gln Val Asn Pro Cys Pro Asn Gly Tyr Ile Val Phe
                245                 250                 255

Trp Met Asp Ser Val Thr Pro Val Cys Leu Lys Phe Ala Met Tyr Gly
            260                 265                 270

Lys Gly Thr Trp Thr Asn Leu Arg Met Met Cys Gln Ala Glu Gly Ala
        275                 280                 285

Asp Leu Ala Lys Leu Asp Gly Asn Leu His Tyr Gln Val Ile Gln Tyr
    290                 295                 300

Ile Asn Asn Gln Arg Pro Asp Leu Gln Asp Glu Ala Phe Trp Ile Gly
305                 310                 315                 320

Gly Thr Asp Ala Ala Ser Glu Gly Tyr Trp Val Trp Ala Met Asp Gly
                325                 330                 335

Thr Gln Met Asp Met Ser Asn Pro Pro Trp Tyr Pro Gly Gln Pro Asn
            340                 345                 350
```

```
Arg Gly Thr Ile Ala Asn Tyr Ala Cys Leu Tyr Thr Pro Asp Phe Met
            355                 360                 365

Phe His Ser Cys Asp Asn Asp Arg Lys Ile Tyr Ala Ile Cys Gln Ile
    370                 375                 380
```

<210> SEQ ID NO 40
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Glu Arg Leu Cys His
225                 230                 235                 240

Pro Cys Pro Trp Glu Trp Thr Phe Phe Gln Gly Asn Cys Tyr Phe Met
                245                 250                 255

Ser Asn Ser Gln Arg Asn Trp His Asp Ser Ile Thr Ala Cys Lys Glu
            260                 265                 270

Val Gly Ala Gln Leu Val Val Ile Lys Ser Ala Glu Glu Gln Asn Phe
        275                 280                 285

Leu Gln Leu Gln Ser Ser Arg Ser Asn Arg Phe Thr Trp Met Gly Leu
    290                 295                 300

Ser Asp Leu Asn Gln Glu Gly Thr Trp Gln Trp Val Asp Gly Ser Pro
305                 310                 315                 320

Leu Leu Pro Ser Phe Lys Gln Tyr Trp Asn Arg Gly Glu Pro Asn Asn
                325                 330                 335
```

-continued

```
Val Gly Glu Glu Asp Cys Ala Glu Phe Ser Gly Asn Gly Trp Asn Asp
            340                 345                 350

Asp Lys Cys Asn Leu Ala Lys Phe Trp Ile Cys Lys Lys Ser Ala Ala
            355                 360                 365

Ser Cys Ser Arg Asp Glu
            370

<210> SEQ ID NO 41
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Glu Arg Leu Cys Arg
225                 230                 235                 240

His Cys Pro Lys Asp Trp Thr Phe Phe Gln Gly Asn Cys Tyr Phe Met
                245                 250                 255

Ser Asn Ser Gln Arg Asn Trp His Asp Ser Val Thr Ala Cys Gln Glu
            260                 265                 270

Val Arg Ala Gln Leu Val Val Ile Lys Thr Ala Glu Gln Asn Phe
        275                 280                 285

Leu Gln Leu Gln Thr Ser Arg Ser Asn Arg Phe Ser Trp Met Gly Leu
    290                 295                 300

Ser Asp Leu Asn Gln Glu Gly Thr Trp Gln Trp Val Asp Gly Ser Pro
```

```
305                 310                 315                 320

Leu Ser Pro Ser Phe Gln Arg Tyr Trp Asn Ser Gly Glu Pro Asn Asn
                325                 330                 335

Ser Gly Asn Glu Asp Cys Ala Glu Phe Ser Gly Ser Gly Trp Asn Asp
                340                 345                 350

Asn Arg Cys Asp Val Asp Asn Tyr Trp Ile Cys Lys Lys Pro Ala Ala
                355                 360                 365

Cys Phe Arg Asp Glu
                370

<210> SEQ ID NO 42
<211> LENGTH: 591
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
                20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
                100                 105                 110

Asn Lys Ala Leu Pro Ala Pro Ile Glu Lys Thr Ile Ser Lys Ala Lys
            115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
                180                 185                 190

Phe Leu Tyr Ser Lys Leu Thr Val Asp Lys Ser Arg Trp Gln Gln Gly
            195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Thr Thr Pro Glu Pro
225                 230                 235                 240

Cys Glu Leu Asp Asp Glu Asp Phe Arg Cys Val Cys Asn Phe Ser Glu
                245                 250                 255

Pro Gln Pro Asp Trp Ser Glu Ala Phe Gln Cys Val Ser Ala Val Glu
                260                 265                 270

Val Glu Ile His Ala Gly Gly Leu Asn Leu Glu Pro Phe Leu Lys Arg
            275                 280                 285
```

Val Asp Ala Asp Ala Asp Pro Arg Gln Tyr Ala Asp Thr Val Lys Ala
    290                 295                 300

Leu Arg Val Arg Arg Leu Thr Val Gly Ala Ala Gln Val Pro Ala Gln
305                 310                 315                 320

Leu Leu Val Gly Ala Leu Arg Val Leu Ala Tyr Ser Arg Leu Lys Glu
                325                 330                 335

Leu Thr Leu Glu Asp Leu Lys Ile Thr Gly Thr Met Pro Pro Leu Pro
            340                 345                 350

Leu Glu Ala Thr Gly Leu Ala Leu Ser Ser Leu Arg Leu Arg Asn Val
        355                 360                 365

Ser Trp Ala Thr Gly Arg Ser Trp Leu Ala Glu Leu Gln Gln Trp Leu
    370                 375                 380

Lys Pro Gly Leu Lys Val Leu Ser Ile Ala Gln Ala His Ser Pro Ala
385                 390                 395                 400

Phe Ser Cys Glu Gln Val Arg Ala Phe Pro Ala Leu Thr Ser Leu Asp
                405                 410                 415

Leu Ser Asp Asn Pro Gly Leu Gly Glu Arg Gly Leu Met Ala Ala Leu
            420                 425                 430

Cys Pro His Lys Phe Pro Ala Ile Gln Asn Leu Ala Leu Arg Asn Thr
        435                 440                 445

Gly Met Glu Thr Pro Thr Gly Val Cys Ala Ala Leu Ala Ala Ala Gly
    450                 455                 460

Val Gln Pro His Ser Leu Asp Leu Ser His Asn Ser Leu Arg Ala Thr
465                 470                 475                 480

Val Asn Pro Ser Ala Pro Arg Cys Met Trp Ser Ser Ala Leu Asn Ser
                485                 490                 495

Leu Asn Leu Ser Phe Ala Gly Leu Glu Gln Val Pro Lys Gly Leu Pro
            500                 505                 510

Ala Lys Leu Arg Val Leu Asp Leu Ser Cys Asn Arg Leu Asn Arg Ala
        515                 520                 525

Pro Gln Pro Asp Glu Leu Pro Glu Val Asp Asn Leu Thr Leu Asp Gly
    530                 535                 540

Asn Pro Phe Leu Val Pro Gly Thr Ala Leu Pro His Glu Gly Ser Met
545                 550                 555                 560

Asn Ser Gly Val Val Pro Ala Cys Ala Arg Ser Thr Leu Ser Val Gly
                565                 570                 575

Val Ser Gly Thr Leu Val Leu Leu Gln Gly Ala Arg Gly Phe Ala
            580                 585                 590

<210> SEQ ID NO 43
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
                20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Lys Phe Asn
        50                  55                  60

Trp Tyr Val Asp Gly Val Glu Val His Asn Ala Lys Thr Lys Pro Arg
 65                  70                  75                  80

Glu Glu Gln Tyr Asp Ser Thr Tyr Arg Val Ser Val Leu Thr Val
             85                  90                  95

Leu His Gln Asp Trp Leu Asn Gly Lys Glu Tyr Lys Cys Lys Val Ser
             100                 105                 110

Asn Lys Ala Leu Pro Ala Pro Ile Glu Lys Thr Ile Ser Lys Ala Lys
             115                 120                 125

Gly Gln Pro Arg Glu Pro Gln Val Tyr Thr Leu Pro Pro Ser Arg Asp
             130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
             165                 170                 175

Asn Asn Tyr Lys Thr Thr Pro Pro Val Leu Asp Ser Asp Gly Ser Phe
             180                 185                 190

Phe Leu Tyr Ser Lys Leu Thr Val Asp Lys Ser Arg Trp Gln Gln Gly
             195                 200                 205

Asn Val Phe Ser Cys Ser Val Met His Glu Ala Leu His Asn His Tyr
210                 215                 220

Thr Gln Lys Ser Leu Ser Leu Ser Pro Gly Ala Cys Ser Phe Ile Val
225                 230                 235                 240

Pro Arg Ser Glu Trp Arg Ala Leu Pro Ser Glu Cys Ser Ser Arg Leu
             245                 250                 255

Gly His Pro Val Arg Tyr Val Val Ile Ser His Thr Ala Gly Ser Phe
             260                 265                 270

Cys Asn Ser Pro Asp Ser Cys Glu Gln Gln Ala Arg Asn Val Gln His
             275                 280                 285

Tyr His Lys Asn Glu Leu Gly Trp Cys Asp Val Ala Tyr Asn Phe Leu
             290                 295                 300

Ile Gly Glu Asp Gly His Val Tyr Glu Gly Arg Gly Trp Asn Ile Lys
305                 310                 315                 320

Gly Asp His Thr Gly Pro Ile Trp Asn Pro Met Ser Ile Gly Ile Thr
             325                 330                 335

Phe Met Gly Asn Phe Met Asp Arg Val Pro Ala Lys Arg Ala Leu Arg
             340                 345                 350

Ala Ala Leu Asn Leu Leu Glu Cys Gly Val Ser Arg Gly Phe Leu Arg
             355                 360                 365

Ser Asn Tyr Glu Val Lys Gly His Arg Asp Val Gln Ser Thr Leu Ser
             370                 375                 380

Pro Gly Asp Gln Leu Tyr Gln Val Ile Gln Ser Trp Glu His Tyr Arg
385                 390                 395                 400

Glu

<210> SEQ ID NO 44
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Pro Ser Pro Gly Cys
225                 230                 235                 240

Pro Thr Ile Val Ser Lys Asn Arg Trp Gly Gln Gln Ala Ser Gln
                245                 250                 255

Val Gln Tyr Thr Val Lys Pro Leu Lys Tyr Val Ile Ile His His Thr
            260                 265                 270

Ser Thr Pro Thr Cys Thr Asn Glu Asp Asp Cys Ser Arg Arg Leu Val
        275                 280                 285

Asn Ile Gln Asp Tyr His Met Asn Arg Leu Asp Phe Asp Asp Ile Gly
290                 295                 300

Tyr Asn Phe Met Ile Gly Gly Asp Gly Gln Ile Tyr Glu Gly Ala Gly
305                 310                 315                 320

Trp His Lys Glu Gly Ala His Ala Arg Gly Trp Asn Ser Lys Ser Leu
                325                 330                 335

Gly Ile Gly Phe Ile Gly Asp Phe Gln Thr Asn Leu Pro Ser Ser Lys
            340                 345                 350

Gln Leu Asp Ala Gly Lys Lys Phe Leu Glu Cys Ala Val Glu Lys Gly
        355                 360                 365

Glu Ile Glu Asp Thr Tyr Lys Leu Ile Gly Ala Arg Thr Val Arg Pro
370                 375                 380

Thr Asp Ser Pro Gly Thr Leu Leu Phe Arg Glu Ile Gln Thr Trp Arg
385                 390                 395                 400

Gly Phe Thr Arg Asn Pro
                405

<210> SEQ ID NO 45
<211> LENGTH: 590

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
210                 215                 220

Thr Gln Lys Ser Leu Ser Leu Ser Pro Gly Asp Ser Ser Trp Asn Lys
225                 230                 235                 240

Thr Gln Ala Lys Gln Val Ser Glu Gly Leu Gln Tyr Leu Phe Glu Asn
                245                 250                 255

Ile Ser Gln Leu Thr Glu Lys Gly Leu Pro Thr Asp Val Ser Thr Thr
            260                 265                 270

Val Ser Arg Lys Ala Trp Gly Ala Glu Ala Val Gly Cys Ser Ile Gln
        275                 280                 285

Leu Thr Thr Pro Val Asn Val Leu Val Ile His Val Pro Gly Leu
290                 295                 300

Glu Cys His Asp Gln Thr Val Cys Ser Gln Arg Leu Arg Glu Leu Gln
305                 310                 315                 320

Ala His His Val His Asn Asn Ser Gly Cys Asp Val Ala Tyr Asn Phe
                325                 330                 335

Leu Val Gly Asp Asp Gly Arg Val Tyr Glu Gly Val Gly Trp Asn Ile
            340                 345                 350

Gln Gly Val His Thr Gln Gly Tyr Asn Asn Ile Ser Leu Gly Phe Ala
        355                 360                 365

Phe Phe Gly Thr Lys Lys Gly His Ser Pro Ser Pro Ala Ala Leu Ser
370                 375                 380

```
Ala Met Glu Asn Leu Ile Thr Tyr Ala Val Gln Lys Gly His Leu Ser
385                 390                 395                 400

Ser Ser Tyr Val Gln Pro Leu Gly Lys Gly Glu Asn Cys Leu Ala
            405                 410                 415

Pro Arg Gln Lys Thr Ser Leu Lys Lys Ala Cys Pro Gly Val Val Pro
            420                 425                 430

Arg Ser Val Trp Gly Ala Arg Glu Thr His Cys Pro Arg Met Thr Leu
        435                 440                 445

Pro Ala Lys Tyr Gly Ile Ile Ile His Thr Ala Gly Arg Thr Cys Asn
        450                 455                 460

Ile Ser Asp Glu Cys Arg Leu Leu Val Arg Asp Ile Gln Ser Phe Tyr
465                 470                 475                 480

Ile Asp Arg Leu Lys Ser Cys Asp Ile Gly Tyr Asn Phe Leu Val Gly
            485                 490                 495

Gln Asp Gly Ala Ile Tyr Glu Gly Val Gly Trp Asn Val Gln Gly Ser
            500                 505                 510

Ser Thr Pro Gly Tyr Asp Asp Ile Ala Leu Gly Ile Thr Phe Met Gly
        515                 520                 525

Thr Phe Thr Gly Ile Pro Pro Asn Ala Ala Leu Glu Ala Ala Gln
        530                 535                 540

Asp Leu Ile Gln Cys Ala Met Val Lys Gly Tyr Leu Thr Pro Asn Tyr
545                 550                 555                 560

Leu Leu Val Gly His Ser Asp Val Ala Arg Thr Leu Ser Pro Gly Gln
            565                 570                 575

Ala Leu Tyr Asn Ile Ile Ser Thr Trp Pro His Phe Lys His
            580                 585                 590

<210> SEQ ID NO 46
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
            85                  90                  95

Leu His Gln Asp Trp Leu Asn Gly Lys Glu Tyr Lys Cys Lys Val Ser
        100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
```

-continued

```
           145                 150                 155                 160
Tyr Pro Ser Asp Ile Ala Val Glu Trp Glu Ser Asn Gly Gln Pro Glu
                    165                 170                 175
Asn Asn Tyr Lys Thr Thr Pro Pro Val Leu Asp Ser Asp Gly Ser Phe
                    180                 185                 190
Phe Leu Tyr Ser Lys Leu Thr Val Asp Lys Ser Arg Trp Gln Gln Gly
                    195                 200                 205
Asn Val Phe Ser Cys Ser Val Met His Glu Ala Leu His Asn His Tyr
                    210                 215                 220
Thr Gln Lys Ser Leu Ser Leu Ser Pro Gly Ala Pro Ser Pro Cys Leu
225                 230                 235                 240
Glu Val Pro Asp Ala Lys Leu Glu Ala Ile Tyr Pro Lys Gly Leu Arg
                    245                 250                 255
Val Ser Ile Pro Asp Asp Gly Tyr Thr Leu Phe Ala Phe His Gly Lys
                    260                 265                 270
Leu Asn Glu Glu Met Glu Gly Leu Glu Ala Gly His Trp Ser Arg Asp
                    275                 280                 285
Ile Thr Lys Ala Lys Asn Gly Arg Trp Ile Phe Arg Asp Arg Asn Ala
                    290                 295                 300
Lys Leu Lys Ile Gly Asp Lys Ile Tyr Phe Trp Thr Tyr Ile Leu Lys
305                 310                 315                 320
Asp Gly Leu Gly Tyr Arg Gln Asp Asn Gly Glu Trp Thr Val Thr Gly
                    325                 330                 335
Tyr Val Asn Glu Asp Gly Glu Pro Leu Asp Ala Asn Phe Glu Pro Arg
                    340                 345                 350
Ser Thr Ala Ser Thr Ala Ala Pro Gln Ala Gly Ala Gly Gln Ala
                    355                 360                 365
Pro Gly Pro Ser Tyr Pro Cys Glu Leu Ser Val Ser Glu Val Ser Val
                    370                 375                 380
Pro Gly Phe Val Cys Lys Gly Gln Met Leu Phe Glu Asp Asn Phe Asn
385                 390                 395                 400
Lys Pro Leu Ala Asp Gly Arg Ile Trp Thr Pro Glu Ile Met Phe Pro
                    405                 410                 415
Gly Glu Pro Asp Tyr Pro Phe Asn Val Tyr Met Lys Glu Thr Asp Asn
                    420                 425                 430
Leu His Val Gly Asn Gly Asn Leu Val Ile Lys Pro Met Pro Leu Val
                    435                 440                 445
Thr Ala Phe Gly Glu Asp Ala Ile Trp Lys Thr Leu Asp Leu Ser Asp
                    450                 455                 460
Arg Cys Thr Gly Leu Leu Gly Thr Ala Gln Cys Lys Arg Asp Pro Ser
465                 470                 475                 480
Asp Ala Ile Ile Val Pro Pro Ile Val Thr Ala Lys Ile Asn Thr Lys
                    485                 490                 495
Lys Thr Phe Ala Phe Lys Tyr Gly Arg Val Glu Ile Ser Ala Lys Met
                    500                 505                 510
Pro Arg Gly Asp Trp Leu Val Pro Leu Ile Gln Leu Glu Pro Val Asn
                    515                 520                 525
Lys Asn Tyr Gly Ile Arg Asn Tyr Val Ser Gly Leu Leu Arg Val Ala
                    530                 535                 540
Cys Val Lys Gly Asn Thr Glu Tyr Ile Lys Thr Leu Val Gly Gly Pro
545                 550                 555                 560
Ile Met Ser Glu Ala Glu Pro Tyr Arg Thr Ala Asn Leu Lys Glu Phe
                    565                 570                 575
```

```
Ile Ser Asn Glu Pro Trp Thr Asn Glu Phe His Asn Tyr Thr Leu Glu
            580                 585                 590

Trp Ser Pro Asp Ala Ile Thr Met Ala Val Asp Gly Ile Val Tyr Gly
            595                 600                 605

Arg Val Thr Ala Pro Ala Gly Gly Phe Tyr Lys Glu Ala Asn Glu Gln
    610                 615                 620

Asn Val Glu Ala Ala Arg Trp Ile Gln Gly Ser Asn Ile Ala Pro
625                 630                 635                 640

Phe Asp Asp Met Phe Tyr Ile Ser Leu Gly Met Asp Val Gly Gly Val
                645                 650                 655

His Glu Phe Pro Asp Glu Ala Ile Asn Lys Pro Trp Lys Asn Thr Ala
            660                 665                 670

Thr Lys Ala Met Val Asn Phe Trp Asn Ala Arg Ser Gln Trp Asn Pro
                675                 680                 685

Thr Trp Leu Glu Ser Gly Lys Ala Leu Leu Val Asp Tyr Val Arg Val
    690                 695                 700

Tyr Ala Leu
705

<210> SEQ ID NO 47
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
```

210                 215                 220
Thr Gln Lys Ser Leu Ser Leu Ser Pro Gly Ala Gln Glu Thr Glu Asp
225                 230                 235                 240

Pro Ala Cys Cys Ser Pro Ile Val Pro Arg Asn Glu Trp Lys Ala Leu
                245                 250                 255

Ala Ser Glu Cys Ala Gln His Leu Ser Leu Pro Leu Arg Tyr Val Val
            260                 265                 270

Val Ser His Thr Ala Gly Ser Ser Cys Asn Thr Pro Ala Ser Cys Gln
        275                 280                 285

Gln Gln Ala Arg Asn Val Gln His Tyr His Met Lys Thr Leu Gly Trp
    290                 295                 300

Cys Asp Val Gly Tyr Asn Phe Leu Ile Gly Glu Asp Gly Leu Val Tyr
305                 310                 315                 320

Glu Gly Arg Gly Trp Asn Phe Thr Gly Ala His Ser Gly His Leu Trp
                325                 330                 335

Asn Pro Met Ser Ile Gly Ile Ser Phe Met Gly Asn Tyr Met Asp Arg
            340                 345                 350

Val Pro Thr Pro Gln Ala Ile Arg Ala Ala Gln Gly Leu Leu Ala Cys
        355                 360                 365

Gly Val Ala Gln Gly Ala Leu Arg Ser Asn Tyr Val Leu Lys Gly His
    370                 375                 380

Arg Asp Val Gln Arg Thr Leu Ser Pro Gly Asn Gln Leu Tyr His Leu
385                 390                 395                 400

Ile Gln Asn Trp Pro His Tyr Arg Ser Pro
                405                 410

<210> SEQ ID NO 48
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

-continued

```
Tyr Pro Ser Asp Ile Ala Val Glu Trp Glu Ser Asn Gly Gln Pro Glu
            165                 170                 175

Asn Asn Tyr Lys Thr Thr Pro Pro Val Leu Asp Ser Asp Gly Ser Phe
        180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Cys Pro Asn Ile Ile
225                 230                 235                 240

Lys Arg Ser Ala Trp Glu Ala Arg Glu Thr His Cys Pro Lys Met Asn
                245                 250                 255

Leu Pro Ala Lys Tyr Val Ile Ile His Thr Ala Gly Thr Ser Cys
                260                 265                 270

Thr Val Ser Thr Asp Cys Gln Thr Val Val Arg Asn Ile Gln Ser Phe
            275                 280                 285

His Met Asp Thr Arg Asn Phe Cys Asp Ile Gly Tyr His Phe Leu Val
        290                 295                 300

Gly Gln Asp Gly Gly Val Tyr Glu Gly Val Gly Trp His Ile Gln Gly
305                 310                 315                 320

Ser His Thr Tyr Gly Phe Asn Asp Ile Ala Leu Gly Ile Ala Phe Ile
                325                 330                 335

Gly Tyr Phe Val Glu Lys Pro Pro Asn Ala Ala Ala Leu Glu Ala Ala
                340                 345                 350

Gln Asp Leu Ile Gln Cys Ala Val Val Glu Gly Tyr Leu Thr Pro Asn
        355                 360                 365

Tyr Leu Leu Met Gly His Ser Asp Val Val Asn Ile Leu Ser Pro Gly
    370                 375                 380

Gln Ala Leu Tyr Asn Ile Ile Ser Thr Trp Pro His Phe Lys His
385                 390                 395

<210> SEQ ID NO 49
<211> LENGTH: 404
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125
```

-continued

Gly Gln Pro Arg Glu Pro Gln Val Tyr Thr Leu Pro Pro Ser Arg Asp
            130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
            195                 200                 205

Asn Val Phe Ser Cys Ser Val Met His Glu Ala Leu His Asn His Tyr
            210                 215                 220

Thr Gln Lys Ser Leu Ser Leu Ser Pro Gly Ala Gln Asp Cys Gly Ser
225                 230                 235                 240

Ile Val Ser Arg Gly Lys Trp Gly Ala Leu Ala Ser Lys Cys Ser Gln
                245                 250                 255

Arg Leu Arg Gln Pro Val Arg Tyr Val Val Ser His Thr Ala Gly
            260                 265                 270

Ser Val Cys Asn Thr Pro Ala Ser Cys Gln Arg Gln Ala Gln Asn Val
            275                 280                 285

Gln Tyr Tyr His Val Arg Glu Arg Gly Trp Cys Asp Val Gly Tyr Asn
            290                 295                 300

Phe Leu Ile Gly Glu Asp Gly Leu Val Tyr Glu Gly Arg Gly Trp Asn
305                 310                 315                 320

Thr Leu Gly Ala His Ser Gly Pro Thr Trp Asn Pro Ile Ala Ile Gly
                325                 330                 335

Ile Ser Phe Met Gly Asn Tyr Met His Arg Val Pro Pro Ala Ser Ala
            340                 345                 350

Leu Arg Ala Ala Gln Ser Leu Leu Ala Cys Gly Ala Ala Arg Gly Tyr
            355                 360                 365

Leu Thr Pro Asn Tyr Glu Val Lys Gly His Arg Asp Val Gln Gln Thr
            370                 375                 380

Leu Ser Pro Gly Asp Glu Leu Tyr Lys Ile Ile Gln Gln Trp Pro His
385                 390                 395                 400

Tyr Arg Arg Val

<210> SEQ ID NO 50
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Lys Phe Asn
        50                  55                  60

Trp Tyr Val Asp Gly Val Glu Val His Asn Ala Lys Thr Lys Pro Arg
65                  70                  75                  80

```
Glu Glu Gln Tyr Asp Ser Thr Tyr Arg Val Ser Val Leu Thr Val
                 85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Cys Pro Ala Ile His
225                 230                 235                 240

Pro Arg Cys Arg Trp Gly Ala Ala Pro Tyr Arg Gly Arg Pro Lys Leu
                245                 250                 255

Leu Gln Leu Pro Leu Gly Phe Leu Tyr Val His His Thr Tyr Val Pro
            260                 265                 270

Ala Pro Pro Cys Thr Asp Phe Thr Arg Cys Ala Ala Asn Met Arg Ser
        275                 280                 285

Met Gln Arg Tyr His Gln Asp Thr Gln Gly Trp Gly Asp Ile Gly Tyr
    290                 295                 300

Ser Phe Val Val Gly Ser Asp Gly Tyr Val Tyr Glu Gly Arg Gly Trp
305                 310                 315                 320

His Trp Val Gly Ala His Thr Leu Gly His Asn Ser Arg Gly Phe Gly
                325                 330                 335

Val Ala Ile Val Gly Asn Tyr Thr Ala Ala Leu Pro Thr Glu Ala Ala
            340                 345                 350

Leu Arg Thr Val Arg Asp Thr Leu Pro Ser Cys Ala Val Arg Ala Gly
        355                 360                 365

Leu Leu Arg Pro Asp Tyr Ala Leu Leu Gly His Arg Gln Leu Val Arg
    370                 375                 380

Thr Asp Cys Pro Gly Asp Ala Leu Phe Asp Leu Leu Arg Thr Trp Pro
385                 390                 395                 400

His Phe

<210> SEQ ID NO 51
<211> LENGTH: 556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30
```

```
Pro Lys Pro Lys Asp Thr Leu Met Ile Ser Arg Thr Pro Glu Val Thr
        35                  40                  45

Cys Val Val Asp Val Ser His Glu Asp Pro Glu Val Lys Phe Asn
 50                      55                  60

Trp Tyr Val Asp Gly Val Glu Val His Asn Ala Lys Thr Lys Pro Arg
 65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
            115                 120                 125

Gly Gln Pro Arg Glu Pro Gln Val Tyr Thr Leu Pro Pro Ser Arg Asp
        130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
            195                 200                 205

Asn Val Phe Ser Cys Ser Val Met His Glu Ala Leu His Asn His Tyr
        210                 215                 220

Thr Gln Lys Ser Leu Ser Leu Ser Pro Gly Ala Pro Thr Ile Val Ser
225                 230                 235                 240

Arg Lys Glu Trp Gly Ala Arg Pro Leu Ala Cys Arg Ala Leu Leu Thr
                245                 250                 255

Leu Pro Val Ala Tyr Ile Ile Thr Asp Gln Leu Pro Gly Met Gln Cys
            260                 265                 270

Gln Gln Gln Ser Val Cys Ser Gln Met Leu Arg Gly Leu Gln Ser His
        275                 280                 285

Ser Val Tyr Thr Ile Gly Trp Cys Asp Val Ala Tyr Asn Phe Leu Val
        290                 295                 300

Gly Asp Asp Gly Arg Val Tyr Glu Gly Val Gly Trp Asn Ile Gln Gly
305                 310                 315                 320

Leu His Thr Gln Gly Tyr Asn Asn Ile Ser Leu Gly Ile Ala Phe Phe
                325                 330                 335

Gly Asn Lys Ile Gly Ser Ser Pro Ser Pro Ala Ala Leu Ser Ala Ala
            340                 345                 350

Glu Gly Leu Ile Ser Tyr Ala Ile Gln Lys Gly His Leu Ser Pro Arg
            355                 360                 365

Tyr Ile Gln Pro Leu Leu Leu Lys Glu Glu Thr Cys Leu Asp Pro Gln
        370                 375                 380

His Pro Val Met Pro Arg Lys Val Cys Pro Asn Ile Ile Lys Arg Ser
385                 390                 395                 400

Ala Trp Glu Ala Arg Glu Thr His Cys Pro Lys Met Asn Leu Pro Ala
                405                 410                 415

Lys Tyr Val Ile Ile Ile His Thr Ala Gly Thr Ser Cys Thr Val Ser
            420                 425                 430

Thr Asp Cys Gln Thr Val Val Arg Asn Ile Gln Ser Phe His Met Asp
        435                 440                 445
```

-continued

```
Thr Arg Asn Phe Cys Asp Ile Gly Tyr His Phe Leu Val Gly Gln Asp
    450                 455                 460

Gly Gly Val Tyr Glu Gly Val Gly Trp His Ile Gln Gly Ser His Thr
465                 470                 475                 480

Tyr Gly Phe Asn Asp Ile Ala Leu Gly Ile Ala Phe Ile Gly Tyr Phe
                485                 490                 495

Val Glu Lys Pro Pro Asn Ala Ala Leu Glu Ala Ala Gln Asp Leu
                500                 505                 510

Ile Gln Cys Ala Val Val Glu Gly Tyr Leu Thr Pro Asn Tyr Leu Leu
            515                 520                 525

Met Gly His Ser Asp Val Val Asn Ile Leu Ser Pro Gly Gln Ala Leu
530                 535                 540

Tyr Asn Ile Ile Ser Thr Trp Pro His Phe Lys His
545                 550                 555
```

<210> SEQ ID NO 52
<211> LENGTH: 393
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Ala Trp Gly Ala
225                 230                 235                 240

Thr Ala Thr Gly Pro Arg Lys Glu Ala Gly Asp His Val Arg Asn Asp
                245                 250                 255
```

Val Cys Pro His Pro Phe Val Asp Ile Asn Gly Arg Cys Leu Phe Val
            260                 265                 270

Asp Asn Phe Ala His Leu Asn Trp Asp Ala Ala Arg Thr Phe Cys Gln
            275                 280                 285

Gly Phe Gln Gly Asp Leu Val Thr Leu Asp Glu Ala Asn Leu Leu Gly
            290                 295                 300

Tyr Ile Val Asp Phe Ile His Gln Glu Gly Leu Thr Glu Arg Ser Tyr
305                 310                 315                 320

Trp Ile Gly Gly Ser Asp Arg Thr Ser Glu Gly Thr Trp Val Trp Thr
                325                 330                 335

Asp Gly Ser Ser Val Arg Met Gly Thr Pro Thr Trp Gly Val Asp Gly
            340                 345                 350

Glu Thr Gln Gln Pro Thr Gly Gly Thr Ser Glu Asn Cys Ile Gly Leu
            355                 360                 365

His Lys Asp Asn Phe Phe Phe Asn Asp Phe Ser Cys Asn Asn Glu
            370                 375                 380

Met Ser Leu Ile Cys Glu Phe Asn Met
385                 390

<210> SEQ ID NO 53
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Lys Phe Asn
        50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
            115                 120                 125

Gly Gln Pro Arg Glu Pro Gln Val Tyr Thr Leu Pro Pro Ser Arg Asp
            130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
            195                 200                 205

Asn Val Phe Ser Cys Ser Val Met His Glu Ala Leu His Asn His Tyr

-continued

```
                    210                 215                 220
Thr Gln Lys Ser Leu Ser Leu Ser Pro Gly Ala Arg Cys Gly Glu Gln
225                 230                 235                 240

Gly Ser Asn Met Glu Cys Pro Asn Asn Leu Cys Ser Gln Tyr Gly
                245                 250                 255

Tyr Cys Gly Met Gly Gly Asp Tyr Cys Gly Lys Gly Cys Gln Asn Gly
                260                 265                 270

Ala Cys Trp Thr Ser Lys Arg Cys Gly Ser Gln Ala Gly Gly Ala Thr
                275                 280                 285

Cys Pro Asn Asn His Cys Cys Ser Gln Tyr Gly His Cys Gly Phe Gly
                290                 295                 300

Ala Glu Tyr Cys Gly Ala Gly Cys Gln Gly Gly Pro Cys Arg Ala Asp
305                 310                 315                 320

Ile Lys Cys Gly Ser Gln Ser Gly Gly Lys Leu Cys Pro Asn Asn Leu
                325                 330                 335

Cys Cys Ser Gln Trp Gly Phe Cys Gly Leu Gly Ser Glu Phe Cys Gly
                340                 345                 350

Gly Gly Cys Gln Ser Gly Ala Cys Ser Thr Asp Lys Pro Cys Gly Lys
                355                 360                 365

Asp Ala Gly Gly Arg Val Cys Thr Asn Asn Tyr Cys Cys Ser Lys Trp
                370                 375                 380

Gly Ser Cys Gly Ile Gly Pro Gly Tyr Cys Gly Ala Gly Cys Gln Ser
385                 390                 395                 400

Gly Gly Cys Asp Ala Val Phe Ala Gly Ala Ile Thr Ala Asn Ser Thr
                405                 410                 415

Leu Leu Ala Glu
            420

<210> SEQ ID NO 54
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Ala Trp Trp Ser Tyr Trp Trp Thr Gln Trp Ala Ser Glu Leu
1               5                   10                  15

Gly Ser Pro Gly Ser Pro
            20

<210> SEQ ID NO 55

<400> SEQUENCE: 55

000

<210> SEQ ID NO 56
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Trp Gly Trp Lys Cys Leu Leu Phe Trp Ala Val Leu Val Thr Ala
1               5                   10                  15
```

-continued

```
Thr Leu Cys Thr Ala Arg Pro Ala Pro Thr Leu Pro Glu Gln Ala Gln
            20                  25                  30

Gln Ser Thr Arg Ala Asp Leu Gly Pro Gly Glu Pro Lys Ser Cys Asp
        35                  40                  45

Lys Thr His Thr Cys Pro Pro Cys Pro Ala Pro Glu Leu Leu Gly Gly
        50                  55                  60

Pro Ser Val Phe Leu Phe Pro Pro Lys Pro Lys Asp Thr Leu Met Ile
65                  70                  75                  80

Ser Arg Thr Pro Glu Val Thr Cys Val Val Val Asp Val Ser His Glu
                85                  90                  95

Asp Pro Glu Val Lys Phe Asn Trp Tyr Val Asp Gly Val Glu Val His
            100                 105                 110

Asn Ala Lys Thr Lys Pro Arg Glu Glu Gln Tyr Asn Ser Thr Tyr Arg
        115                 120                 125

Val Val Ser Val Leu Thr Val Leu His Gln Asp Trp Leu Asn Gly Lys
    130                 135                 140

Glu Tyr Lys Cys Lys Val Ser Asn Lys Ala Leu Pro Ala Pro Ile Glu
145                 150                 155                 160

Lys Thr Ile Ser Lys Ala Lys Gly Gln Pro Arg Glu Pro Gln Val Tyr
                165                 170                 175

Thr Leu Pro Pro Ser Arg Asp Glu Leu Thr Lys Asn Gln Val Ser Leu
            180                 185                 190

Thr Cys Leu Val Lys Gly Phe Tyr Pro Ser Asp Ile Ala Val Glu Trp
        195                 200                 205

Glu Ser Asn Gly Gln Pro Glu Asn Asn Tyr Lys Thr Thr Pro Pro Val
210                 215                 220

Leu Asp Ser Asp Gly Ser Phe Phe Leu Tyr Ser Lys Leu Thr Val Asp
225                 230                 235                 240

Lys Ser Arg Trp Gln Gln Gly Asn Val Phe Ser Cys Ser Val Met His
                245                 250                 255

Glu Ala Leu His Asn His Tyr Thr Gln Lys Ser Leu Ser Leu Ser Pro
            260                 265                 270

Gly Lys
```

AQUEOUS BIOMOLECULE COUPLING ON CO2-PLASMA-ACTIVATED SURFACES

RELATED APPLICATIONS

This application is a 35 U.S.C. § 371 National Phase Entry Application of International Application No. PCT/US2017/032928 filed May 16, 2017 which designates the U.S., and which claims the benefit of U.S. Ser. No. 62/336,940 filed May 16, 2016, the contents of each of which are incorporated herein by reference in its entirety.

STATEMENT CONCERNING GOVERNMENT RIGHTS IN FEDERALLY-SPONSORED RESEARCH

The invention was made with Government Support under N66001-11-1-4180 awarded by Space and Naval Warfare Systems Center U.S. Department of Defense and HR0011-13-C-0025 awarded by Defense Advanced Research Projects Agency U.S. Department of Defense. The government has certain rights in the invention.

SEQUENCE LISTING

The instant application contains a Sequence Listing which has been submitted electronically in ASCII format and is hereby incorporated by reference in its entirety. Said ASCII copy, created on Nov. 15, 2018, is named 002806-085421-PCT_SL.txt and is 119,029 bytes in size.

BACKGROUND

Current methods for targeted binding of desired moieties on surfaces can require chemical crosslinkers and/or organic washes that can damage the surface. There is a need in the art for improved methods of coupling a desired moiety to a surface.

SUMMARY OF THE INVENTION

In some aspects, the present disclosure provides a method of a method of making a substrate having an entity attached thereto the method comprising:
  i) contacting the substrate with a plasma to form a modified substrate comprising a plasma-generated-moiety (a PGM);
  ii) contacting the entity with the modified substrate under conditions sufficient for attachment of the biological polymer to the modified substrate;
  thereby making a substrate having the entity attached thereto, provided that one or more of: the substrate is fluid-permeable, ion-permeable, porous, flexible, autoclavable, or other than polystyrene; the biological polymer comprises a fusion protein; the biological polymer comprises a lectin; and
  provided that one or more of the following:
    the plasma is other than an oxygen plasma, e.g., the plasma is a $CO_2$ plasma;
    the modified substrate is not contacted with or derivatized with a crosslinking moiety, e.g., a silane, e.g., (3-Aminopropyl) trimethoxysilane (APTMS), prior to attachment of the entity; or
    the modified substrate is not contacted with an organic solvent, e.g., an organic alcohol, e.g., ethanol, prior to attachment of the entity.

In some aspects, the disclosure also provides a device comprising a substrate having an entity attached thereto, produced by or producible by the methods described herein. In embodiments, the device is a hemodialysis or hemofiltration device.

In some aspects, the disclosure also provides a method of using a device comprising a substrate having an entity attached thereto, produced by or producible by the methods described herein, comprising contacting the device with a sample under conditions that allow a molecule in the sample to bind to the entity. In some embodiments the sample is a blood sample during hemodialysis or hemofiltration that is returned to the subject's body.

In some aspects, the disclosure provides a method of making a substrate having an entity (e.g., a polypeptide, e.g., a glycopolypeptide, e.g., a glycoprotein, a nucleic acid, a carbohydrate, e.g., a polysaccharide, a biological polymer, a small molecule, a peptidomimetic, a drug, or a moiety that can interact with, e.g., specifically bind, a pathogenic or disease molecule, e.g., bind a glycopolypeptide, e.g., a glycoprotein) attached thereto, the method comprising: I:
  i) contacting the substrate with a plasma to form a modified substrate comprising a plasma-generated-moiety (PGM);
  ii) contacting the entity (e.g., a biological polymer, e.g., a polypeptide) with the modified substrate under conditions sufficient for attachment of the biological polymer to the modified substrate;
II:
  i) obtaining a modified substrate comprising a PGM; and
  ii) contacting the entity (e.g., a biological polymer, e.g., a polypeptide) with the modified substrate under conditions sufficient for attachment of the entity to the modified substrate; or
III:
  i) contacting the substrate with a plasma to form a modified substrate comprising a PGM; and
  ii.a) classifying, the modified substrate comprising a PGM as suitable for contacting with the entity (e.g., a biological polymer, e.g., a polypeptide) with the modified substrate under conditions sufficient for attachment of the entity to the modified substrate; or
  ii.b) transporting, selling, shipping, transferring control of, or transferring possession of, the modified substrate comprising a PGM to a party for contacting the entity (e.g., a biological polymer, e.g., a polypeptide) with the modified substrate under conditions sufficient for attachment of the entity to the modified substrate;
  thereby making a substrate having the entity attached thereto,
    provided that one or more (e.g., 2, 3, 4, 5, 6, 7, 8, 9, 10, or all) of the following:
      a) the substrate is fluid-permeable, ion-permeable, porous, flexible, autoclavable (e.g., retains structure at above 100C), or other than polystyrene;
      b) the substrate comprises less than 90, 80,70, 60 or 50% polystyrene
      c) the substrate comprises polysulfone (PS), polyarylethersulfone (PAES) or polyethersulfone (PES);
      d) the substrate comprises a structure having a compartment, e.g., a lumen, e.g., the structure comprises a hollow fiber;
      e) the entity comprises a first member of a specific binding pair;
      f) the entity comprises an antibody domain, e.g., an Fc domain;
      g) the entity comprises a fusion protein;

h) the entity comprises an opsonin;
i) the entity comprises a lectin;
j) the entity comprises a subunit of a multimeric protein; or
k) an attached entity is cross linked to a second entity, e.g., wherein the second entity is attached to the substrate or wherein the second entity is not attached to the substrate; and provided that one or more (e.g., 2 or all) of the following:
l) the plasma is other than an oxygen plasma, e.g., the plasma is a $CO_2$ plasma;
m) the modified substrate is not contacted with or derivatized with a crosslinking moiety (e.g., a silane, e.g., (3-Aminopropyl) trimethoxysilane (APTMS)) prior to attachment of the entity; or
n) the modified substrate is not contacted with an organic solvent (e.g., an organic alcohol, e.g., ethanol) prior to attachment of the entity.

With reference to a) through k) above, in some embodiments two or more of a) through k) are present, e.g., a) and b), a) and c), a) and d), a) and e), a) and f), a) and g), a) and h), a) and i), a) and j), a) and k), b) and c), b) and d), b) and e), b) and f), b) and g), b) and h), b) and i), b) and j), b) and k), c) and d), c) and e), c) and f), c) and g), c) and h), c) and i), c) and j), c) and k), d) and e), d) and f), d) and g), d) and h), d) and i), d) and j), d) and k), e) and f), e) and g), e) and h), e) and i), e) and j), e) and k), f) and g), f) and h), f) and i), f) and j), f) and k), g) and h), g) and i), g) and j), g) and k), h) and i), h) and j), h) and k), i) and j), i) and k), and j) and k). With reference to l) through n) above, in some embodiments two or more of l) through n) are present, e.g., l) and m), l) and n), or m) and n). In some embodiments, one of a) through k) and one of l) through n) is present, e.g., a) and l), b) and l), c) and l), d) and l), e) and l), f) and l), g) and l), h) and l), i) and l), j) and l), k) and l), a) and m), b) and m), c) and m), d) and m), e) and m), f) and m), g) and m), h) and m), i) and m), j) and m), k) and m), a) and n), b) and n), c) and n), d) and n), e) and n), f) and n), g) and n), h) and n), i) and n), j) and n), or k) and n).

In some embodiments, the method comprises: I: i) contacting the substrate with a plasma to form a modified substrate comprising a plasma-generated-moiety; and ii) contacting the entity (e.g., a biological polymer, e.g., a polypeptide) with the modified substrate under conditions sufficient for attachment of the biological polymer to the modified substrate. In some embodiments, the method comprises: II: i) obtaining a substrate modified substrate comprising a PGM; and ii) contacting the entity (e.g., a biological polymer, e.g., a polypeptide) with the modified substrate under conditions sufficient for attachment of the biological polymer to the modified substrate. In some embodiments, the method comprises: III: i) a contacting the substrate with a plasma to form a modified substrate comprising a PGM; and ii.a) classifying, the modified substrate comprising a PGM as suitable for contacting the entity (e.g., a biological polymer, e.g., a polypeptide) with the modified substrate under conditions sufficient for attachment of the biological polymer to the modified substrate; or ii.b) transporting, selling, shipping, transferring control of, or transferring possession of, the modified substrate comprising a PGM to a party for contacting the entity (e.g., a biological polymer, e.g., a polypeptide) with the modified substrate under conditions sufficient for attachment of the biological polymer to the modified substrate.

In some embodiments, the entity is attached directly to a PGM, e.g., without atoms from an activating moiety, a crosslinking moiety, a linker, or a spacer disposed between the PGM and the entity. In some embodiments, a) the entity is attached directly to a PGM, e.g., without atoms from an activating moiety disposed between the PGM and the biological polymer; b) after contacting the substrate with the plasma, the entity is attached directly to a PGM; c) the reaction or reactions for attaching the PGM with the entity are aqueous; d) the entity is contacted with the modified substrate under aqueous conditions; e) PGMs, e.g., carboxylic acids, are formed at an abundance of at least about 1%, 2%, 3%, 4%, 5%, 6%, 7%, 8%, 9%, 10%, 15%, or 20% by carbon composition, e.g., as measured by XPS, or PGMs e.g., alcohols, aldehydes, and carboxylic acids are formed at an abundance of at least about 1%, 2%, 3%, 4%, 5%, 6%, 7%, 8%, 9%, 10%, 15%, or 20% as measured by Carbon is spectra; f) entities are attached at a density of at least about $1\times10^{12}$, $1\times10^{13}$, $1\times10^{14}$, $1\times10^{15}$, $1\times10^{16}$, or $1\times10^{17}$ molecules per $cm^2$, e.g., as measured by a binding method or an imaging method; or g) the entity is contacted with the modified substrate at a pH between 6 and 8 (e.g., pH 7 or physiological conditions). In some embodiments, entities are attached to the substrate at a density of at least about 500 entities/$m^2$, e.g., about 500-2000, 500-1800, 500-1600, or 500-1200 entities/$m^2$. In some embodiments, entities are attached to the substrate at a density of at least about 600 entities/$m^2$, e.g., about 600-2000, 600-1800, 600-1600, or 600-1200 entities/$m^2$. In some embodiments, entities are attached to the substrate at a density of at least about 800 entities/$m^2$, e.g., about 800-2000, 800-1800, 800-1600, or 800-1200 entities/$m^2$. In some embodiments, entities are attached to the substrate at a density of at least about 1000 entities/$m^2$, e.g., about 1000-2000, 1000-1800, 1000-1600, or 1000-1200 entities/$m^2$. In some embodiments, entities are attached at a density of at least about 500, 600, 700, 800, 900, 1000, or 1100 entities/$m^2$. In some embodiments, the entity is a multimer.

In some embodiments, the entity is attached to the substrate in a stable manner, e.g., a hydrolysis-resistant manner, e.g., such that under aqueous conditions less than 1%, 2%, 5%, or 10% of the entity detaches from the substrate over a predetermined time period, e.g., 1, 2, 4, 6, 12, 24, 48, or 72 hours.

In some embodiments, the substrate comprises a lumen, e.g., the substrate comprises a hollow fiber. In some embodiments, the substrate comprises cellulose, substituted cellulose e.g., cellulose acetate, cellulose diacetate, or cellulose triacetate; polysulfone, polyethersulfone, polyarylethersulfone, polyvinylpyrrolidone, nylon, polyacrylonitrile (PAN), polycarbonate, polyamide, or polymethylmethacrylate (PMMA). In some embodiments, the substrate comprises polydimethylsiloxane (PDMS) or polystyrene. In some embodiments, the substrate comprises an adhesive or a sealant, and wherein the adhesive or sealant is not contacted with an organic solvent, e.g., an organic alcohol, e.g., ethanol. In some embodiments, the substrate comprises, is attached to, or is disposed in a dialysis, ultrafiltration, hemofiltration, hemodiafiltration, or hemoperfusion cartridge. In some embodiments, the substrate comprises a polymer, glass, metal, or ceramic, or any combination thereof. In some embodiments, the substrate comprises a dialysis membrane, e.g., a hemodialysis membrane. In some embodiments, the substrate comprises a hollow-fiber or non-hollow-fiber membrane.

In some embodiments, in step (ii), e.g., I(ii), the modified substrate is substantially free of a crosslinking moiety, e.g., silane, e.g., (3-Aminopropyl) trimethoxysilane (APTMS). In some embodiments, in step (ii) e.g., i(ii), the modified substrate is substantially free of organic solvent, or the method does not comprise a step of contacting the modified substrate with an organic solvent, e.g., after step (i) or before step (ii). In some embodiments, the method comprises contacting the modified substrate, the entity, or both, with an activating moiety, e.g., a water-soluble activating moiety, e.g., 1-Ethyl-3-(3-dimethylaminopropyl)carbodiimide (EDC), to activate a functional group on the modified substrate, wherein the functional group is optionally a carboxylic acid group. In some embodiments, step ii) e.g., I(ii) contacting is performed in aqueous buffer. In some embodiments, step ii) e.g., I(ii) contacting is performed in a solution comprising 2-morpholino-ethane sulfonic acid (MES) buffer. In some embodiments, step ii) e.g., I(ii) contacting is performed at a pH of about 4-5,4.5-5.5, 5-6, 6-7, 7-8, or about 5. In some embodiments, step ii) e.g., I(ii) contacting is performed for about 4-6, 6-8, 8-10, 10-12, 12-14, or 14-16 hours.

In some embodiments, the activating moiety comprises an atom that is not included in the substrate having the entity attached thereto, e.g., none of the atoms of the activating moiety are included in the substrate having the entity attached thereto.

In embodiments, the method does not include use of an activating moiety, e.g., a water-soluble activating moiety, e.g., EDC. In embodiments, the method comprises use of less than 5, 2, 1, 0.5, 0.2, 0.1, 0.05, 0.02, 0.01, 0.005, 0.002, or 0.001 mg/ml of, an activating moiety, e.g., a water-soluble activating moiety, e.g., EDC.

In some embodiments, the PGM comprises a carboxylic acid and the entity comprises an amine. In some embodiments, a carboxylic acid of the PGM covalently binds with an amine group of the entity.

In some embodiments, the method comprises contacting the substrate with the plasma under conditions suitable for forming a predetermined level or density of PGMs on the substrate. In some embodiments, the PGM comprises a hydroxyl, aldehyde, epoxide, peroxide, sulfhydryl, carbonyl, or carboxylic acid group. In some embodiments, the PGM comprises a carboxylic acid group. In some embodiments, at least 1, 2, 3, 4, 5, 6, 7, 8, 9, 10, 20, 30, 40, or 50% of the PGMs comprise a carboxylic acid group. In some embodiments, the PGM comprises an aldehyde group. In some embodiments, at least 1, 2, 3, 4, 5, 6, 7, 8, 9, 10, 20, 30, 40, or 50% of the PGMs comprise an aldehyde group. In some embodiments, the PGM comprises a moiety that is reactive with a moiety on the entity or an activated entity.

In some embodiments, the plasma is generated by a plasma generator under one or more (e.g., 2, 3, 4, or all) of the following conditions: a) a radio frequency of about 12-15 or 13-14 MHz, e.g., 13.5 MHz), or at least about 10, 11, 12, 14, 15 MHz, or no more than about 15, 14, 13, 12, 11, or 10 Hz; b) plasma treatment lasts a sufficient amount of time to link the entity to the modified substrate while maintaining an activity, e.g., a binding activity, of the entity, e.g., the plasma treatment lasts about 0.1-5 min, e.g., about 1 min, or at least about 0.1, 0.5, 1, 2, 3, 4, or 5 minutes, or no more than about 5, 4, 3, 2, or 1 minute; c) the plasma gas pressure is about 150-350 mTorr, e.g., about 200 mTorr, or at least about 150, 200, 250, 300, or 350 mTorr, or no more than about 350, 300, 250, 200, or 150 mTorr; d) a power of about 10-150 W, e.g., about 100 W; or at least about 10, 20, 30, 40, 50, 75, 100, 135, or 150 W, or no more than about 150, 125, 100, 75, 50, 40, 30, 20, or 10 W; or e) the plasma generator comprises electrodes outside the plasma generator chamber, e.g., does not comprise electrodes inside the plasma generator chamber.

In some embodiments, step i) contacting comprises contacting a plurality of substrates (e.g., at least 2, 3, 4, 5, 10, 20, 50, or 100 substrates) with a plasma in a plasma generator chamber.

In some embodiments, the entity comprises an opsonin, a carbohydrate-binding protein, a calcium-binding protein, a divalent cation binding protein, and/or a portion of an antibody, e.g., an Fc or portion thereof. In some embodiments, the entity comprises a polypeptide of SEQ ID NO: 4 or at least 80%, 85%, 90%, 95%, 96%, 97%, 98%, or 99% identical to SEQ ID NO: 4, or a polypeptide of SEQ ID NO: 6 or at least 80%, 85%, 90%, 95%, 96%, 97%, 98%, or 99% identical to SEQ ID NO: 6. In some embodiments, the entity forms a multimer, e.g., a dimer, trimer, tetramer, pentamer, hexamer, 12-mer, or 18-mer. In some embodiments, the entity forms a multimer having at least two (e.g., 3, 4, 5, 6, 12, or 18) subunits crosslinked to each other. In some embodiments, the biological polymer forms a multimer having at least two (e.g., 3, 4, 5, 6, 12, or 18) subunits covalently connected to each other. The covalent linkage may be formed, e.g., spontaneously, enzymatically, or through chemical crosslinking. The covalent linkage may comprise, e.g., a disulfide bridge. In some embodiments, the entity forms a multimer having at least two (e.g., 3, 4, 5, 6, 12, or 18) subunits noncovalently bound to each other.

In some embodiments, the method further comprises acquiring a value for a parameter related to the type of PGM, the number of PGMs, the density of PGMs, the presence of contaminants, the number of attached entities, a contact angle measurement (e.g., a water contact angle measurement), or a surface energy measurement, and comparing the acquired value with a standard. In some embodiments, the method further comprises, responsive to the comparison, classifying, accepting, rejecting, approving, incorporating into a product, packaging, transferring to a new location, or releasing into commerce, the substrate comprising an attached entity. In some embodiments, the method further comprises evaluating the modified substrate, e.g., with X-ray photon spectroscopy (XPS), for the presence of a PGM. In some embodiments, the method further comprises, evaluating the modified substrate for contaminants or manufacturing reagents, e.g., an extractable molecule, a leachable molecule, FcMBL not linked to the substrate, an activating reagent, a crosslinking reagent, EDC, solvent (e.g., MES buffer), endotoxin, pyrogen, nuclease, or an organism e.g., a bacterium or fungus.

In some embodiments, the method further comprises, further comprising: cleansing the plasma generator chamber. The cleansing step may take place before step i), e.g., I(i). The method may include, performing one or more of (e.g., 2 or all of): a) washing the chamber with a solvent (e.g., an organic solvent, e.g., ethanol) b) producing a cleansing plasma in the chamber (e.g., a cleansing plasma made of a different gas from the plasma of step i), e.g., cleansing using an O2 plasma when the plasma of step i) is a $CO_2$ plasma); and/or c) cleaning the chamber by chemical cleaning e.g., chemical etching.

In some embodiments, the cleansing plasma is produced for about 30 minutes. In some embodiments, the cleansing plasma is at a temperature (e.g., peak temperature) of 100-800C, 200-700C, 300-500C, 350-450C, or about 400 C. In some embodiments the cleansing plasma is at a temperature (e.g., peak temperature) of at least about 100 C, 200 C, 300 C, or 400 C. In some embodiments, the cleansing plasma is at a temperature (e.g., peak temperature) of no more than about 800 C, 700 C, 600 C, 500 C, or 400 C.

In embodiments, the method comprises determining the cleanliness of the plasma generator chamber. For instance, the method comprises a) during the cleansing step, monitoring the color of the plasma, e.g., wherein an $O_2$ plasma is blue when organic matter is present and white when organic matter is absent, or a $CO_2$ plasma is dark blue when organic matter is present and light blue when organic matter is absent; or b) during the contacting of step i), monitoring the temperature of the plasma, wherein the temperature of the plasma does not rise above 80 C in the first minute that the plasma is produced, or wherein temperature rising above 80 C in the first minute indicates presence of a contaminant, or c) during the cleansing step, monitoring the temperature of the plasma, wherein the temperature of the plasma drops below 10 C of peak temperature (typically between 400-500 C), or wherein temperature continuing to rise or maintaining the peak temperature indicates presence of a contaminant, or any combination thereof. In embodiments, when the method indicates that the contaminant is present, the cleansing reaction is prolonged, e.g., until the method indicates the absence of the contaminant. In embodiments, when the method indicates that the contaminant is present, another cleansing method such as chemical cleansing is performed. In embodiments, when the substrate is disposed in the plasma generator chamber, e.g., before the contacting of step i), performing one or both of a) creating a vacuum in the plasma generator chamber (e.g., a pressure of less than 1 Torr) and b) filling the plasma generator chamber with a gas, e.g., the same gas used to make the plasma of step i), e.g., $CO_2$. In embodiments, the plasma generator chamber is filled with the gas, e.g., $CO_2$, for, e.g., at least about 1, 2, 3, 4, 5, 6, 7, 8, 9, or 10 minutes, e.g., about 5 minutes. In embodiments, the method comprises measuring modification of the substrate, e.g., by performing one or more of: a) contacting the substrate with a drop of a liquid, e.g., water, and measuring the contact angle of the drop of liquid; b) contacting the substrate with a moiety that binds the entity, e.g., wherein the moiety comprises an antibody molecule or a saccharide such as mannose, wherein the moiety is optionally bound or covalently linked to a detectable label; or c) contacting the substrate with a moiety that binds a PGM, e.g., a detectable label comprising an amine group.

In embodiments, the method comprises comprising providing a masking entity during attachment of the entity to the substrate, wherein the masking entity inhibits reaction of a portion of the entity with, e.g., the activating moiety, the substrate, or another entity e.g., a biological polymer such as a polypeptide. In embodiments, the masking entity comprises a moiety to which the entity binds. In embodiments, the entity comprises an ion-binding protein, a divalent ion-binding protein, a calcium-binding protein, an opsonin, e.g., a lectin, e.g., a calcium-binding lectin, e.g., MBL. The masking entity may comprise a moiety to which the opsonin binds, e.g., a divalent cation, e.g., $Ca^{2+}$. In some embodiments, the masking entity comprises a sugar, e.g., glucose.

In an embodiment, the entity binds a sugar (e.g., mannose or glucose) and the masking entity comprises a sugar (e.g., mannose or glucose). In embodiments, the entity comprises an opsonin, opsonin fragment (e.g., a mannose-binding fragment), MBL, MBL fragment (e.g., a mannose-binding fragment, e.g., a CRD domain or a CRD domain and neck domain); and the masking entity binds the opsonin, e.g., the CRD of the opsonin. In an embodiment, the masking entity competes for binding with mannose, and in another embodiment, the masking entity does not compete for binding with mannose. In an embodiment, the masking entity that binds the opsonin is a divalent cation, e.g., $Ca^{2+}$ or a sugar, e.g., glucose or mannose. In embodiments, the masking entity, when complexed with the entity, protects one or more amino acid residues of the entity, e.g., residues in a CRD domain, e.g., amino acids in a sugar-binding site.

In an embodiment, the entity binds a protein (e.g., a bacterial or viral protein) and the masking entity comprises a protein (e.g., a bacterial or viral protein). In embodiments, the entity binds a lipid and the masking entity comprises a lipid.

In embodiments, the density of attached entities, e.g., as measured by a binding assay or an imaging method, in a first selected area, e.g., a one $cm^2$ area, is within 50% of the density of 1, 2, 3, 4, 5, or 10 other selected areas, e.g., areas of one $cm^2$ each on the substrate.

In embodiments, the density of 10, 20, 30, 40, 50, 60, or 70% of the one $cm^2$ areas on the substrate, or a portion of the substrate, e.g., the lumen of a hollow fiber, are within 50, 40, or 30% of one another or of a base of a well, bases of a plurality of wells, or a hollow fiber.

In some aspects, the disclosure also provides a device comprising a substrate, e.g., a permeable membrane, having an entity, e.g., a polypeptide, e.g., a polypeptide comprising a portion of an MBL, attached thereto, wherein the device comprises less than $1\times10^{16}$, $1\times10^{15}$, $1\times10^{14}$, $1\times10^{13}$, $1\times10^{12}$, $1\times10^{11}$, $1\times10^{10}$, $1\times10^{9}$, $1\times10^{8}$, $1\times10^{7}$, $1\times10^{6}$, $1\times10^{5}$, $1\times10^{4}$, $1\times10^{3}$, 100, 10, or 1 molecule per $cm^2$ of a crosslinking agent, e.g., silane, e.g., as measured by a binding assay.

In some aspects, the disclosure also provides a device comprising a substrate, e.g., a permeable membrane, having a plurality of entities, e.g., polypeptides, e.g., a polypeptide comprising a portion of an MBL, attached thereto, wherein the density of attached entities, e.g., as measured by a binding assay or an imaging method, in a first selected area, e.g., a one $cm^2$ area, is within 50% of the density of 1, 2, 3, 4, 5, or 10 other selected areas, e.g., one $cm^2$ areas on the substrate, or wherein the density of 10, 20, 30, 40, 50, 60, or 70% of the one $cm^2$ areas on the substrate, or a portion of the substrate, e.g., the lumen of a hollow fiber, are within 50, 40, or 30% of one another or of a base of a well, bases of a plurality of wells, or a hollow fiber.

In some aspects, the disclosure also provides a device comprising a substrate, e.g., a permeable membrane, having an entity, e.g., a polypeptide, e.g., a polypeptide comprising a portion of an MBL, attached thereto, wherein an amino group of the entity (e.g., an amino group of a lysine side chain or an N-terminus) is directly covalently bound to a PGM (e.g., a carboxylic acid) on the substrate.

In some aspects, the disclosure also provides a device comprising a substrate, e.g., a permeable membrane, having an entity, e.g., a polypeptide, e.g., a polypeptide comprising a portion of an MBL, attached thereto, wherein the device comprises less than $1\times10^{16}$, $1\times10^{15}$, $1\times10^{14}$, $1\times10^{13}$, $1\times10^{12}$, $1\times10^{11}$, $1\times10^{10}$, $1\times10^{9}$, $1\times10^{8}$, $1\times10^{7}$, $1\times10^{6}$, $1\times10^{5}$, $1\times10^{4}$, $1\times10^{3}$, 100, 10, or 1 molecules per $cm^2$ or less than $1\times10^{16}$, $1\times10^{15}$, $1\times10^{14}$, $1\times10^{13}$, $1\times10^{12}$, $1\times10^{11}$, $1\times10^{10}$, $1\times10^{9}$, $1\times10^{8}$, $1\times10^{7}$, $1\times10^{6}$, $1\times10^{5}$, $1\times10^{4}$, $1\times10^{3}$, 100, 10, or 1 molecules per device of a contaminant, e.g., an extractable molecule, a leachable molecule, FcMBL not linked to the substrate, EDC, solvent (e.g., MES buffer), endotoxin, pyrogen, nuclease, or an organism e.g., a bacterium or fungus.

In some aspects, the disclosure also provides a reaction mixture comprising:

a substrate, e.g., a permeable membrane, which comprises less than $1\times10^{16}$, $1\times10^{15}$, $1\times10^{14}$, $1\times10^{13}$, $1\times10^{12}$, $1\times10^{11}$, $1\times10^{10}$, $1\times10^{9}$, $1\times10^{8}$, $1\times10^{7}$, $1\times10^{6}$, $1\times10^{5}$, $1 \times 10^4$, $1 \times 10^3$, 100, 10, or 1 molecule per $cm^2$ of a crosslinking agent, e.g., a silane;

an entity, e.g., a polypeptide, e.g., a polypeptide comprising a portion of an MBL; and an aqueous solution comprising an activating moiety, e.g., a water-soluble activating moiety, e.g., EDC.

In some aspects, the disclosure also provides a reaction mixture comprising: a substrate, e.g., a permeable membrane, which comprises less than $1 \times 10^{16}$, $1 \times 10^{15}$, $1 \times 10^{14}$, $1 \times 10^{13}$, $1 \times 10^{12}$, $1 \times 10^{11}$, $1 \times 10^{10}$, $1 \times 10^9$, $1 \times 10^8$, $1 \times 10^7$, $1 \times 10^6$, $1 \times 10^5$, $1 \times 10^4$, $1 \times 10^3$, 100, 10, or 1 molecule per $cm^2$ of a crosslinking agent, e.g., a silane; and an entity, e.g., a polypeptide, e.g., a polypeptide comprising a portion of an MBL. In embodiments, the reaction mixture does not comprise, or comprises less than 5, 2, 1, 0.5, 0.2, 0.1, 0.05, 0.02, 0.01, 0.005, 0.002, or 0.001 mg/ml of, an activating moiety, e.g., a water-soluble activating moiety, e.g., EDC.

In some aspects, the disclosure also provides a reaction mixture comprising:

a substrate, e.g., a permeable membrane, an entity, e.g., a polypeptide, e.g., a polypeptide comprising a portion of an opsonin e.g., a portion of MBL; and a masking entity, e.g., a moiety to which the opsonin binds or a divalent cation e.g., $Ca^{2+}$.

In some embodiments, the masking entity comprises a sugar, e.g., glucose.

In some embodiments, a reaction mixture described herein is disposed within a chamber configured to produce or contain a plasma.

In embodiments, a party (e.g., a party that contacts an entity with a modified substrate) is a person or a corporate entity. In embodiments, the party contacts the entity with the modified substrate automatically, e.g., by using or configuring automated equipment to perform the contacting.

The disclosure includes all combinations of any one or more of the foregoing aspects and/or embodiments, as well as combinations with any one or more of the embodiments set forth in the detailed description and examples.

Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another.

All publications, patent applications, patents, and other references mentioned herein are incorporated by reference in their entirety.

Other features, objects, and advantages of the invention will be apparent from the description and drawings, and from the claims.

DETAILED DESCRIPTION

Definitions

Figure 1:
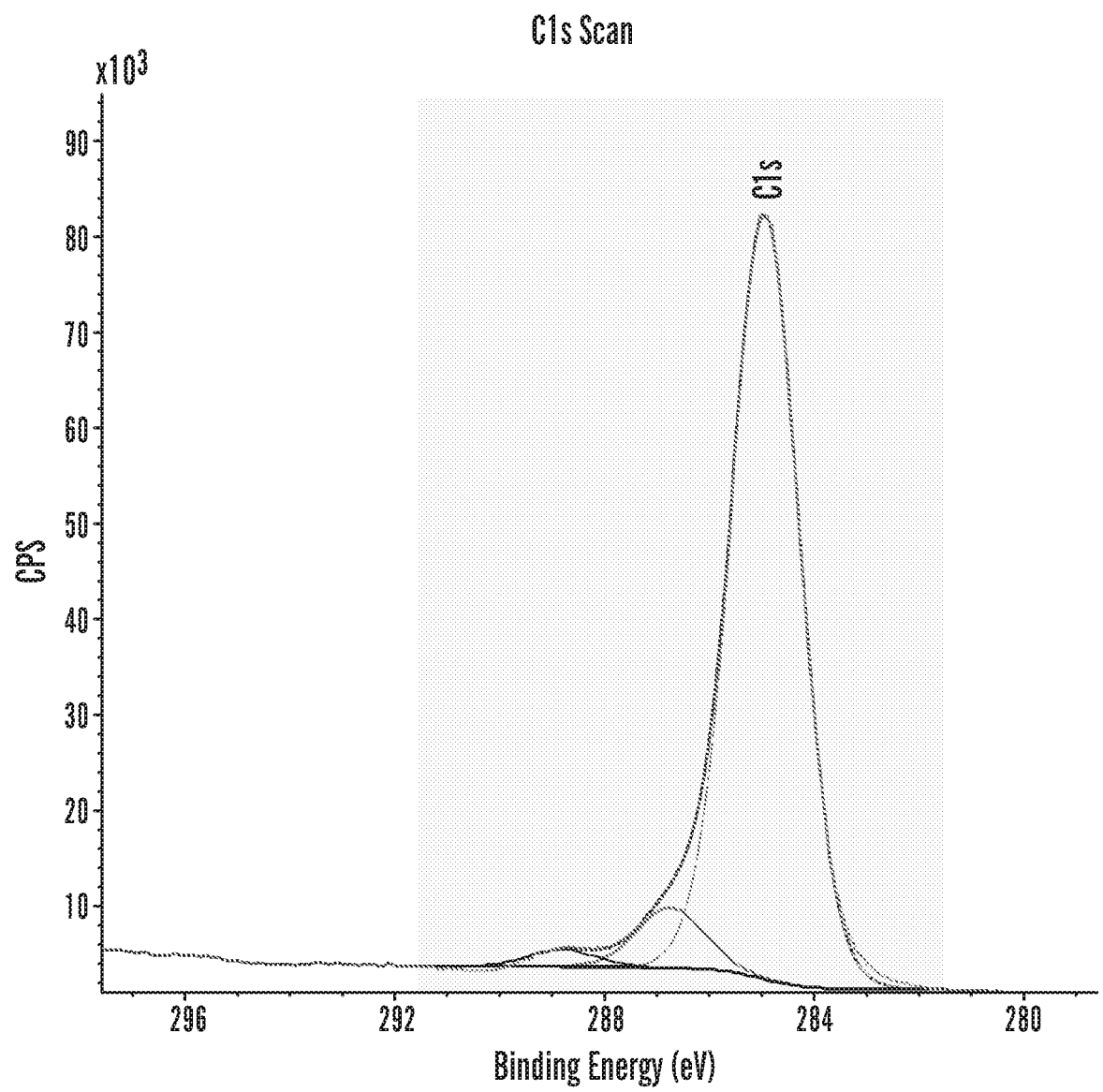
FIG. 1 shows that XPS Spectra of untreated PES specimen reveal primarily reduced carbon atoms on the surface.

As used herein, "activating moiety" refers to a molecule that makes a functional group more reactive. For example, an activating moiety can react (e.g., covalently) with the functional group to form a modified functional group with a higher reactivity towards, e.g., increased propensity to form a covalent bond with, a second functional group. In some embodiments, the first functional group is part of an entity and the second functional group is a plasma generated moiety. In some embodiments, the activating moiety comprises an atom that is not included in the substrate having the entity attached thereto, e.g., none of the atoms of the activating moiety are included in the substrate having the entity attached thereto.

The term "antibody molecule" as used herein refers to immunoglobulin molecules and immunologically active portions of immunoglobulin molecules (molecules that contain an antigen binding site which specifically binds an antigen), including monoclonal antibodies (including full length monoclonal antibodies), polyclonal antibodies, multispecific antibodies (for example, bispecific antibodies), chimeric antibodies, humanized antibodies, human antibodies, and single chain antibodies (e.g., scFvs).

The term "biological polymer" as used herein is intended to mean a polymer comprising repeating units of biological moieties. Representative biopolymers include, but are not limited to, nucleic acids, oligonucleotides, amino acid-based polymers, proteins, peptides, peptide hormones, oligosaccharides, lipids, glycolipids, lipopolysaccharides, phospholipids, synthetic analogues of the foregoing, including, but not limited to, polymers comprising inverted nucleotides, peptide nucleic acids, and combinations of the above.

The term "carbohydrate recognition domain" or CRD, as used herein refers to a region, at least a portion of which, can bind to carbohydrates on a surface of microbes or pathogens or a fragment of a microbe or pathogen. For example, the carbohydrate recognition domain, in some embodiments, can encompass mannose-binding lectin (MBL) CRD. However, in some embodiments, the carbohydrate recognition domain can be also construed to encompass a neck region in addition to MBL CRD. In some embodiments, the carbohydrate recognition domain can comprise at least about 50% of its domain, including at least about 60%, at least about 70%, at least about 80%, at least about 90% or higher, capable of binding to carbohydrates on a microbe surface. In some embodiments, 100% of the carbohydrate recognition domain can be used to bind to microbes or pathogens. In other embodiments, the carbohydrate recognition domain can comprise additional regions that are not capable of carbohydrate binding, but can have other characteristics or perform other functions, e.g., to provide flexibility to the carbohydrate recognition domain when interacting with microbes or pathogens.

As used herein, a "cartridge" refers to a device comprising a substrate and an entity attached thereto. In an embodiment the cartridge comprises a substrate and an entity attached thereto disposed within a housing. In an embodiment, the cartridge is configured to allow for connection to another element of a system. The cartridge can be, e.g., reusable or disposable. A hemodialysis cartridge refers to a cartridge configured to allow connection to a hemodialysis machine. As used herein, the term "detectable label" refers to a composition that produces a detectable signal indicative of the presence of a target.

As used herein, "crosslinking moiety" refers to a molecule that can react covalently with a first functional group (e.g., on an entity) to form a modified functional group with a higher reactivity towards (e.g., increased propensity to form a covalent bond with) a second functional group (e.g., a plasma generated moiety), and which crosslinking moiety comprises an atom (e.g., a plurality of atoms) that is covalently bonded with the first and/or second functional groups after a crosslinking reaction is complete. In some embodiments, the crosslinking moiety comprises an atom (e.g., a plurality of atoms) which, after crosslinking moiety mediated coupling of an entity to a plasma generated moiety, remains and links the first entity to the plasma generated moiety. In some embodiments, the crosslinking moiety comprises an atom (e.g., a plurality of atoms) that is included in the substrate having the entity attached thereto.

As used herein, an "entity" refers to moiety, molecule, or complex of molecules. An entity can comprise, e.g., a small molecule, a polypeptide, e.g., a glycopolypeptide, e.g., a glycoprotein, a nucleic acid, a carbohydrate, e.g., a polysaccharide, a biological polymer, a peptidomimetic, or a drug, or any combination thereof.

"Extractable molecule" as used herein, refers to a molecule that exits from, e.g., desorbs from, dissolves from, or becomes chemically unlinked from, a substrate. The extractable molecule may exit the substance, e.g. when the substance is contacted with a solvent, e.g., an aqueous or organic solvent.

"Glycopolypeptide" as used herein refers to a polypeptide that comprises a glycosyl group, e.g., a plurality of glycosyl groups, e.g., an oligosaccharide or polysaccharide chain. In embodiments, the glycopolypeptide comprises N-linked or O-linked glycosylation.

"Leachable molecule", as used herein, refers to a molecule that dissolves from a substance, e.g., when the substance is contacted with a solvent, e.g., an aqueous or organic solvent.

The term "lectin" as used herein refers to any molecules including proteins, natural or genetically modified (e.g., recombinant), that interact specifically with saccharides (e.g., carbohydrates). The term "lectin" as used herein can also refer to lectins derived from any species, including, but not limited to, plants, animals, insects and microorganisms, having a desired carbohydrate binding specificity. Examples of plant lectins include, but are not limited to, the Leguminosae lectin family, such as ConA, soybean agglutinin, peanut lectin, lentil lectin, and *Galanthus nivalis* agglutinin (GNA) from the *Galanthus* (snowdrop) plant. Other examples of plant lectins are the Gramineae and Solanaceae families of lectins. Examples of animal lectins include, but are not limited to, any known lectin of the major groups S-type lectins, C-type lectins, P-type lectins, and I-type lectins, and galectins. In some embodiments, the carbohydrate recognition domain can be derived from a C-type lectin, or a fragment thereof. C-type lectin can include any carbohydrate-binding protein that requires calcium for binding. In some embodiments, the C-type lectin can include, but are not limited to, collectin, DC-SIGN, and fragments thereof. Without wishing to be bound by theory, DC-SIGN can generally bind various microbes by recognizing high-mannose-containing glycoproteins on their envelopes and/or function as a receptor for several viruses such as HIV and Hepatitis C.

As used herein, the term "microbes" or "microbe" generally refers to microorganism(s), including bacteria, fungi, viruses, protozoan, archaea, protists, e.g., algae, and a combination thereof. The term "microbes" encompasses both live and dead microbes. The term "microbes" also includes pathogenic microbes or pathogens, e.g., bacteria causing diseases such as plague, tuberculosis and anthrax; protozoa causing diseases such as malaria, sleeping sickness and toxoplasmosis; fungi causing diseases such as ringworm, candidiasis or histoplasmosis; and bacteria or other microbes causing diseases such as sepsis.

The term "masking entity" as used herein refers to a molecule or moiety that inhibits reaction of a portion of the entity with a reactant. The reactant can be, e.g., an activating moiety such as a crosslinking agent; a substrate; or another entity e.g., a free radical or a biological polymer such as a polypeptide. In embodiments, the masking entity binds an opsonin (e.g., MBL), for instance, the masking entity comprises a divalent cation such as $Ca^{2+}$ or a sugar such as glucose.

The term "microbial matter" as used herein refers to any matter or component that is derived, originated, or secreted from a microbe. For example, microbial matter or a component derived or secreted from a microbe can include, but are not limited to, a cell wall component, an outer membrane, a plasma membrane, a ribosome, a microbial capsule, pili or flagella, any fragments of the aforementioned microbial components, any nucleic acid (e.g., DNA, including 16S ribosomal DNA, and RNA) derived from a microbe, and microbial endotoxin (e.g., lipopolysaccharide). In addition, microbial matter can encompass non-viable microbial matter that can cause an adverse effect (e.g., toxicity) to a host or an environment.

"Modified substrate," as used herein, refers to a substrate comprising a plasma-generated-moiety (a PGM), e.g., a functional group, formed by contacting a substrate with a plasma. In embodiments the moiety comprises a hydroxyl, epoxide, carbonyl, or carboxylic acid group. In embodiments the moiety comprises a group that is reactive with an entity, e.g., a biological polymer, e.g., in the presence of an activating moiety such as EDC.

The term "opsonin" as used herein refers to naturally-occurring and synthetic molecules which are capable of binding to or attaching to the surface of a microbe or a pathogen, or acting as binding enhancers for a process of phagocytosis.

As used herein, "pathogenic or disease molecule" refers to a molecule, or fragment of a molecule, that is associated with, e.g., contributes to or is indicative of, a disease, e.g., a disease caused by a pathogen. In some embodiments, the pathogenic molecule is a molecule present in a pathogen, e.g., on a pathogen's surface. The pathogenic or disease molecule comprise, e.g., microbial matter, a cell wall component, an outer membrane, a plasma membrane, a ribosome, a microbial capsule, pili or flagella, any fragments of the aforementioned microbial components, any nucleic acid (e.g., DNA, including 16S ribosomal DNA, and RNA) derived from a microbe, and microbial endotoxin (e.g., lipopolysaccharide) or exotoxins (e.g., hemolysin and toxic shock syndrome toxin-l). In embodiments, the pathogenic or disease molecule is physically associated with a pathogen or fragment of a pathogen.

The term "peptide" or "polypeptide" are used interchangeably to refer to a polymer of amino acids, or amino acid analogs, regardless of its size or function. In some embodiments, the term "peptide" refers to small polypeptides, e.g., a polymer of about 15-25 amino acids.

As used herein, a "permeable" substance refers to a substance that allows a fluid to pass through it. The term "permeable" includes semipermeable or selectively permeable substances. In some embodiments, the permeable substance allows solvent (e.g., water) to pass through it but not one or more solutes.

A "plasma" as used herein refers to a state of matter comprising primarily positive ions and free electrons. A plasma typically has no, or a very small, overall electric charge. A "$CO_2$ plasma" refers to a plasma produced from a $CO_2$ gas, e.g., comprising free electrons and carbon and oxygen nuclei.

A "specific binding pair" as used herein refers to a pair of moieties or molecules with greater affinity for each other than for a reference molecule. In some embodiments, the members of the specific binding pair have an affinity for each other of less than or equal to $10^7$, $10^8$, $10^9$, $10^{10}$, or $10^{11} K_D$.

As used herein, "subject" and "patient" are used interchangeably to mean a human or animal, e.g., mammal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate, e.g., a human. A subject can be one who has been previously diagnosed with or identified as suffering from or having a disease or disorder caused by any microbes or pathogens described herein. By way of example only, a subject can be diagnosed with sepsis, inflammatory diseases, or infections.

Entities, e.g., for Attaching to Substrates Using the Methods Herein

An entity can comprise, e.g., a small molecule, a polypeptide, e.g., a glycopolypeptide, e.g., a glycoprotein, a nucleic acid, a carbohydrate, e.g., a polysaccharide, a biological polymer, a small molecule, a peptidomimetic, a drug, a polymer (e.g. PEG or PNA), a secreted protein, a signaling molecule, a membrane-embedded protein, a nucleic acid, a chromosome, a nucleus, a mitochondrion, a chloroplast, a flagellum, a biomineral, a minicell, an antibody molecule, an antigen, a receptor, or any combination thereof. An entity can also comprise a complex of molecules, e.g., a plurality of molecules, non-covalently bound to each other, such as protein/protein complexes or nucleic acid/protein complexes. Examples of entities are described herein.

In some embodiments, entities are attached at a density described herein, e.g., at least about $1 \times 10^{12}$, $1 \times 10^{13}$, $1 \times 10^{14}$, $1 \times 10^{15}$, $1 \times 10^{16}$, or $1 \times 10^{17}$ molecules per $cm^2$ or about 500-2000, 500-1800, 500-1600, 500-1200, 600-2000, 600-1800, 600-1600, 600-1200, 800-2000, 800-1800, 800-1600, 800-1200, 1000-2000, 1000-1800, 1000-1600, or 1000-1200 entities/$m^2$. In some embodiments, the entity is a multimer.

In embodiments, density is determined using a binding assay or an imaging assay. In embodiments, the imaging assay is conducted as described in Example 7. When a non-fluorescent entity is detected, a labeling molecule can be added, e.g., if the entity is a protein, an antibody to the protein can be added. The antibody may be directly labeled or a secondary antibody with a label may be added.

Some suitable entities include proteins, peptides, nucleic acids, polysaccharides, saccharides, proteoglycans, heparin, heparin sulfate, poly(N-isopropylacrylamide), polyurethane, metals and metal oxides (e.g. ferric oxide, ferrous oxide, cupric oxide, aluminum, aluminum oxide, zinc oxide, zinc, magnesium, calcium, and the like), alginate, silk, glycosaminoglycans, keratin, silicates, phospholipids, polyethylene glycol diol, ethylene glycol, polypropylene glycol, perfluoroglutamic acid, perfluoropolyether (Krytox), hydroxyl-terminated, amine-terminated, methyl-terminated, and/or hydrocarbon-terminated polydimethylsiloxane, polysulfone, polyethersulfone, polymethylmethacrylate, poly(lactic-co-glycolic acid), polyacrylimide, polybutadiene, water, formamide, gluteraldehyde, acetic acid, cellulose, keratin, chitosan, chitin, polylactic acid, aliphatic hydrocarbons, aromatic hydrocarbons, phenyl groups and aptamers.

An entity can comprise at least one microbe surface-binding domain, including at least two, at least three, at least four, at least five, at least six, at least seven, at least eight, at least nine, at least ten or more microbe surface-binding domains. The term "microbe surface-binding domain" as used herein refers to any molecule or a fragment thereof that can specifically bind to the surface of a microbe or pathogen, e.g., any component present on a surface of a microbe or pathogen, and/or any microbial matter, e.g., any matter or component/fragment that is derived, originated or secreted from a microbe. Molecules that can be used in the microbe surface-binding domain can include, for example, but are not limited to, peptides, polypeptides, proteins, peptidomimetics, antibody molecules, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof. In some embodiments, the microbe surface-binding domain can comprise a carbohydrate recognition domain or a fragment thereof. In some embodiments, a microbe surface-binding domain can comprise a peptidomimetic that mimics any molecule or a fragment thereof that can specifically bind to the surface of a microbe or pathogen, and/or any microbial matter. For example, a microbe surface-binding domain can comprise a peptidomimetic that mimics any carbohydrate recognition domain or a fragment thereof, e.g., carbohydrate recognition domain of MBL or a fragment thereof, or any carbohydrate recognition domain that is known in the art or a fragment thereof. In some embodiments, the microbe-surface binding domain comprises the full amino acid sequence of a carbohydrate-binding protein. In some embodiments, the microbe surface-binding domain can have an amino acid sequence of about 10 to about 300 amino acid residues, or about 50 to about 150 amino acid residues. In some embodiments, the microbe surface-binding domain can have an amino acid sequence of at least about 5, at least about 10, at least about 15, at least about 20, at least about 30, at least about 40, at least about 50, at least about 60, at least about 70, at least about 80, at least about 90, at least about 100 amino acid residues or more. For any known sequences of microbe surface-binding molecules, one of skill in the art can determine the optimum length of amino acid sequence for the microbe surface-binding domain.

An entity, in some embodiments, comprises at least one amino group that can non-covalently or covalently couple with functional groups on the surface of the substrate. For example, the primary amines of the amino acid residues (e.g., lysine or cysteine residues) at the N-terminus or in close proximity to the N-terminus of a polypeptide entity can be used to couple with functional groups on the substrate surface. In some embodiments, a primary amine of an amino acid residue (e.g., lysine) in the polypeptide (e.g., near the N-terminus, near the C-terminus, or in a central region of the polypeptide) can be used to couple with functional groups on the substrate surface.

Antibody Molecules and Other Binding Proteins

In some embodiments, the entity comprises at least a portion of an immunoglobulin, e.g., IgA, IgD, IgE, IgG and IgM including their subclasses (e.g., $IgG_1$), or a modified molecule or recombinant thereof. In one embodiment, the portion retains one or more biological functions (e.g., binding properties) of the full length molecule. Immunoglobulins include IgG, IgA, IgM, IgD, and IgE. An immunoglobulin portion (e.g., fragments) and immunoglobulin derivatives include but are not limited to single chain Fv (scFv), diabodies, Fv, and (Fab')2, triabodies, Fc, Fab, CDR1, CDR2, CDR3, combinations of CDR's, variable regions of the light or heavy Ig chains, tetrabodies, bifunctional hybrid antibodies, framework regions, constant regions, and the like (see, Maynard et al, (2000) Ann. Rev. Biomed. Eng. 2:339-76; Hudson (1998) Curr. Opin. Biotechnol. 9:395-402). In one embodiment, an immunoglobulin molecule can encompass immunoglobulin ortholog genes, which are genes conserved among different biological species such as humans, dogs, cats, mice, and rats, that encode proteins (for example, homologs (including splice variants), mutants, and derivatives) having biologically equivalent functions as the human-derived protein. Immunoglobulin orthologs include any mammalian ortholog of IgG, IgA, IgM, IgD, or IgE inclusive of the ortholog in humans and other primates, experimental mammals (such as mice, rats, hamsters and guinea pigs), mammals of commercial significance (such as horses, cows, camels, pigs and sheep), and also companion mammals (such as domestic animals, e.g., rabbits, ferrets, dogs, and cats), or a camel, llama, or shark.

For example, the Fc portion of an FcMBL molecule, or the Fc portion of any entity described herein, can be replaced with any of the immunoglobulin fragments described herein.

In some embodiments, the entity comprises at least a portion of an adhesion molecule, or a modified molecule or recombinant thereof. In one embodiment, the portion retains one or more biological functions (e.g., binding properties) of the full length molecule. Non-limiting examples of adhesion molecules include: cell adhesion molecules (e.g. cadherins, selecting, integrins, addressins, lymphocyte homing receptors (e.g. CD-34, GLYCAM-1)); Synaptic Cell Adhesion Molecules (SynCAMs); Neural Cell Adhesion Molecules (NCAMs); Intercellular Cell Adhesion Molecules (ICAM-i); Vascular Cell Adhesion Molecules (VCAM-i); Platelet-endothelial Cell Adhesion Molecules (PECAM-l). In one embodiment, an adhesion molecule can encompass ortholog genes discussed herein.

Other non-limiting examples of entities include a portion of L1, CHL1, MAG, Nectins and nectin-like molecules, CD2, CD48, SIGLEC family members (e.g. CD22, CD83), and CTX family members (e.g. CTX, JAMs, BT-IgSF, CAR, VSIG, ESAM)). In one embodiment, the portion retains one or more biological functions (e.g., binding properties) of the full length molecule.

In some embodiments, the entity comprises at least a portion of heparin. Heparin binds various proteins including growth factors (e.g., FGF1, FGF2, FGF7), serine proteases (e.g., Thrombin, Factor Xa) and serine protease inhibitors (such as Antithrombin). In some embodiments, the entity comprises at least a portion of a glycosaminoglycan (GAG). In some embodiments, the entity comprises at least one glycosaminoglycan (GAG). A GAG includes, but is not limited to a heparin/heparan sulfate GAG (HSGAG), a chondroitin/dermatan sulfate GAG (CSGAG), a keratan sulfate GAG, and hyaluronic acid. In some embodiments, the entity comprises Hemopexin, or a portion thereof, e.g., a Heme-binding portion thereof.

In some embodiments, the entity comprises a heme-binding molecule described in International Application WO2014/190040, which is herein incorporated by reference in its entirety. For instance the entity can comprise an engineered heme-binding molecule comprising a hemopexin domain. The molecule may also comprise a second domain selected from the group consisting of: a linker; a microbe-binding molecule; and/or a substrate binding domain, wherein the second domain is conjugated to the hemopexin domain.

In some embodiments, the entity comprises a C-reactive protein (CRP) molecule described in International Application WO2015/095604, which is herein incorporated by reference in its entirety. For instance, the entity can comprise a microbe-targeting molecule comprising: at least one first domain comprising at least a portion of a c-reactive protein (CRP). In some embodiments, the molecule also comprises at least one second domain which optionally comprises at least a portion of a domain selected from the group consisting of: i. Fc region of an immunoglobulin; ii. microbe-binding domain of a microbe-binding protein, wherein the microbe-binding protein is not CRP; iii. neck region of a lectin; iv. a detectable label; v. domain for conjugation to surface of a carrier scaffold; vi. pattern recognition receptor domain of CRP; and vii. any combinations of (i)-(vi); and optionally c. a linker conjugating the first and second domains.

In some embodiments, the entity can comprise at least a portion of a receptor molecule, or a modified molecule or recombinant thereof. In one embodiment, the portion retains one or more biological functions (e.g., binding properties) of the full length molecule. Non-limiting examples of a receptor molecule include: an extracellular receptor molecule (e.g. nicotinic acetylcholine receptor, glycine receptor, GABA receptors, glutamate receptor, NMDA receptor, AMPA receptor, Kainate receptor, 5-HT3 receptor, P2X receptor); an intracellular receptor molecule (e.g. a cyclic nucleotide-gated ion channel, IPS receptor, intracellular ATP receptor, ryanodine receptor); an immune receptor molecule (e.g. pattern recognition receptors, toll-like receptors, killer activated and killer inhibitor receptors, complement receptors, Fc receptors, B cell receptors and T cell receptors); a G protein coupled receptor molecule, a virus receptor molecule (e.g., CAR-Coxsackie Adenovirus Receptor); an iron scavenging receptor molecule (e.g., LRP/CD91, CD163). In one embodiment, a receptor molecule can encompass ortholog genes and proteins discussed herein. In some embodiments, the entity comprises a hormone receptor. In some embodiments, the hormone receptor is a peptide hormone receptor or a steroid hormone receptor. The peptide hormone receptor can be a cell surface receptor or transmembrane receptor that binds to its cognate hormone ligand. The steroid hormone receptor is a soluble receptor that binds to its cognate hormone ligand. In one embodiment, the peptide hormone receptor comprises a thyroid-stimulating hormone receptor, a follicle-stimulating hormone receptor, a leutinizing hormone receptor, a glucagon receptor, or an insulin receptor. In another embodiment, the receptor is for glucocorticoids, estrogens, androgens, thyroid hormone (T3), calcitriol (vitamin D), or the retinoids (vitamin A). In some embodiments, the transmembrane receptor is a G-protein coupled receptor, which binds to Gs or Gi proteins.

In further embodiments, the entity comprises at least a portion of a ligand that enriches for circulating tumor cells, for example antibody molecules to tumor cell markers. Ligands that enrich for circulating tumor cells include, but are not limited to, antibody molecules to EpCAM, antibody molecules to CD46, antibody molecules to CD24, and antibody molecules to CD133. In further embodiments, the entity comprises at least a portion of a ligand that enriches for fetal cells in maternal circulation. Ligands that enrich for fetal cells include, but are not limited to, antibody molecules to CD71, and antibody molecules to glycophorin-A. In further embodiments, the entity comprises at least a portion of a ligand that enriches for circulating leukocytes, such as antibody molecules to CD45, and antibody molecules to CD15. In yet other embodiments, the entity comprises at least a portion of non-immunoglobulin binding proteins engineered for specific binding properties. For example, the entity may contain ankyrin repeats, or the entity can be anticalins. In one embodiment, anticalins can be used to screen libraries for binding to a target molecule (e.g., see Gebauer, M., & Skerra, A. (2009). Engineered protein scaffolds as next-generation antibody therapeutics. Current opinion in chemical biology, 13(3), 245-255; and Lofblom, J., Frejd, F. Y., & Stahl, S. (2011). Non-immunoglobulin based protein scaffolds. Current Opinion in Biotechnology, 22(6), 843-848, each of which are incorporated by reference in their entireties).

In some embodiments, the Fc portion or any immunoglobulin fragment described herein is coupled to any entity described herein, which targets a specific ligand, cell, or combination thereof.

In one embodiment, the amino acid sequence of a Fc region comprises SEQ ID NO: 56.

SEQ ID NO: 56 depicts the amino acid sequence of a Fc domain:

Opsonins, e.g., Lectins

In some embodiments, the entity comprises an opsonin such as a lectin. In some embodiments, the entity comprises a microbe surface-binding domain or a microbe-binding molecule.

In some embodiments, the entity comprises an opsonin or a fragment thereof. Examples of opsonins which can be used in the methods described herein include, but are not limited to, vitronectin, fibronectin, complement components such as C1q (including any of its component polypeptide chains A, B and C), complement fragments such as C3d, C3b and C4b, mannose-binding protein, conglutinin, surfactant proteins A and D, C-reactive protein (CRP), alpha2-macroglobulin, and immunoglobulins, for example, the Fc portion of an immunoglobulin.

In some embodiments, the entity can comprise a carbohydrate recognition domain. In some embodiments, the entity can further comprise at least a portion of a carbohydrate-binding protein or a portion thereof. In some embodiments, the portion of the carbohydrate-binding proteins can activate the complement system. In alternative embodiments, the portion of the carbohydrate-binding protein cannot activate the complement system. In some embodiments, the portion of the carbohydrate-binding protein can be selected or configured such that it cannot activate the complement system, e.g., via modification. Examples of carbohydrate-binding proteins include, but are not limited to, lectin, collectin, ficolin, mannose-binding lectin (MBL), maltose-binding protein, arabinose-binding protein, and glucose-binding protein. Additional carbohydrate-binding proteins that can be included in the microbe surface-binding domain described herein can include, but is not limited to, lectins or agglutinins that are derived from a plant, e.g., *Galanthus nivalis* agglutinin (GNA) from the *Galanthus* (snowdrop) plant, and peanut lectin. In some embodiments, pentraxin family members, e.g., C-reactive protein, can also be used as a carbohydrate-binding protein. Pentraxin family members can generally bind capsulated microbes. The carbohydrate-binding proteins can be wild-type, recombinant or a fusion protein. The respective carbohydrate recognition domains for such carbohydrate-binding proteins are known in the art, and can be modified for various embodiments of the engineered microbe-targeting molecules described herein. In some embodiments, peptidomimetics or any structural mimics mimicking a microbe surface-binding domain (e.g., a carbohydrate recognition domain or a fragment

```
                                                                 (SEQ ID NO: 56)
  1   MWGWKCLLFW  AVLVTATLCT  ARPAPTLPEQ  AQQSTRADLG  PGEPKSCDKT  HTCPPCPAPE

61   LLGGPSVFLF  PPKPKDTLMI  SRTPEVTCVV  VDVSHEDPEV  KFNWYVDGVE  VHNAKTKPRE

121   EQYNSTYRVV  SVLTVLHQDW  LNGKEYKCKV  SNKALPAPIE  KTISKAKGQP  REPQVYTLPP

181   SRDELTKNQV  SLTCLVKGFY  PSDIAVEWES  NGQPENNYKT  TPPVLDSDGS  FFLYSKLTVD

241   KSRWQQGNVF  SCSVMHEALH  NHYTQKSLSL  SPGK
```

In some embodiments, the N-linked glycosylation of the Fc region can be removed. For example, in Fc MBL.81 the glycosylation can be removed by changing the amino acid at residue 297 from asparagine to aspartic acid (N297D) in the Kabat system of numbering amino acids in antibodies, this corresponds to amino acid 82 in this particular Fc construct. Thus, in some embodiments position 82 is D and in some embodiments position 82 is N.

thereof) and capable of binding to a microbe surface can also be used as a microbe surface-binding domain described herein.

Collectins are soluble pattern recognition receptors (PRRs) belonging to the superfamily of collagen containing C-type lectins. Exemplary collectins include, without limitations, mannose-binding lectin (MBL) (also known as mannan-binding lectin, mannan-binding protein, or mannose-binding protein), surfactant protein A (SP-A), surfactant protein D (SP-D), collectin liver 1 (CL-L1), collectin placenta 1 (CL-P1), conglutinin, collectin of 43 kDa (CL-43), collectin of 46 kDa (CL-46), and a fragment thereof.

Mannose-binding lectin (MBL), also known as mannose binding protein (MBP), or mannan-binding lectin or mannan-binding protein, is a calcium-dependent serum protein that can play a role in the innate immune response by binding to carbohydrates on the surface of a wide range of microbes or pathogens (viruses, bacteria, fungi, protozoa) where it can activate the complement system. MBL can also serve as a direct opsonin and mediate binding and/or uptake of pathogens by tagging the surface of a pathogen to facilitate recognition and ingestion by phagocytes.

MBL is a member of the collectin family of proteins. A native MBL is a multimeric structure (e.g., about 650 kDa) composed of subunits, each of which contains three identical polypeptide chains. Each MBL polypeptide chain (containing 248 amino acid residues in length with a signal sequence: SEQ ID NO: 1) comprises a N-terminal cysteine rich region, a collagen-like region, a neck region, and a carbohydrate recognition domain (CRD). The sequence of each region has been identified and is well known in the art. SEQ ID NO: 2 shows a full-length amino acid sequence of MBL without a signal sequence.

The surface or carbohydrate recognition function of a native MBL is mediated by clusters of three C-type carbohydrate-recognition domains (CRDs) held together by coiled-coils of a-helices. The N-terminal portion collagen-like domain is composed of Gly-X-Y triplets. The short N-terminal domain contains several cysteine residues that form interchain disulfide bonds. Serum MBLs assemble into larger forms containing 2-4 trimeric subunits in rodents and as many as six subunits in humans. All three oligomeric forms of rat serum MBP, designated MBPA, can fix complement, although the larger oligomers have higher specific activity. Many species express a second form of MBP. In rats, the second form, MBP-C, is found in the liver. MBP-C does not form higher oligomers beyond the simple subunit that contains three polypeptides.

When a native MBL interacts with carbohydrates on the surface of microbes or pathogens, e.g., calcium-dependent binding to the carbohydrates mannose, N-acetylglucosamine, and/or fucose, it can form the pathogen recognition component of the lectin pathway of complement activation. The MBL binds to surface arrays containing repeated mannose or N-acetylglucosamine residues. It circulates as a complex with one or more MBP-associated serine proteases (MASPs) that autoactivate when the complex binds to an appropriate surface. The MBL and associated MASP proteins can activate C2/C4 convertase leading to the deposition of C4 on the pathogen surface and opsonization for phagocytosis. The native MBL can also activate coagulation function through MASP proteins.

While native MBL can detect microbes or pathogens and act as opsonins for tagging the microbes for phagocytosis, native MBLs may not be desirable for use in treatment of microbe-induced inflammatory diseases or infections, e.g., sepsis, because native MBLs can activate complement system and induce an inflammatory response. In one embodiment, the entity is an engineered MBL molecule that binds to microbes or pathogens, comprising at least one carbohydrate recognition domain or a fragment thereof, e.g., derived from MBL. In some embodiments, the engineered MBL molecule can comprises at least two, at least three or at least four carbohydrate recognition domains or a fragment thereof. In some embodiments, the engineered MBL molecules do not activate complement system or coagulation side effects that are present in a native MBL. Such embodiments can be used as dominant-negative inhibitors of downstream responses in vivo or as microbe-binding proteins that do not induce coagulation or complement fixation in vitro. For example, the engineered MBL molecules that do not have complement fixation and/or coagulation domains can act as a dominant negative protein in terms of activating cytokine and/or inflammatory cascades, and thus reduce system inflammatory syndrome and/or sepsis symptoms.

In some embodiments, the entity comprises a dimeric engineered MBL molecule. The dimeric molecule can comprise at least two carbohydrate recognition domains (e.g., MBL CRD) connected, directly or indirectly, to a linker, e.g., an Fc region. The N-terminal of the Fc region can further comprise an oligopeptide, e.g., comprising an amino acid sequence AKT. In some embodiments, the carbohydrate recognition domains can further comprise neck regions such as MBL neck to provide flexibility of the CRD interacting with microbes.

The full-length amino acid sequence of carbohydrate recognition domain (CRD) of MBL is shown in SEQ ID NO: 4. The carbohydrate recognition domain of an engineered MBL described herein can have an amino acid sequence of about 10 to about 300 amino acid residues, or about 50 to about 160 amino acid residues. In some embodiments, the microbe surface-binding domain can have an amino acid sequence of at least about 5, at least about 10, at least about 15, at least about 20, at least about 30, at least about 40, at least about 50, at least about 60, at least about 70, at least about 80, at least about 90, at least about 100, at least about 150 amino acid residues or more. Accordingly, in some embodiments, the carbohydrate recognition domain of the engineered MBL molecule can comprise SEQ ID NO. 4. In some embodiments, the carbohydrate recognition domain of the engineered MBL molecule can comprise a fragment of SEQ ID NO: 4. Exemplary amino acid sequences of such fragments include, but are not limited to, ND (SEQ ID NO: 10), EZN (SEQ ID NO: 11: where Z is any amino acid, e.g., P), NEGEPNNAGS (SEQ ID NO: 12) or a fragment thereof comprising EPN, GSDEDCVLL (SEQ ID NO: 13) or a fragment thereof comprising E, and LLLKNGQWNDVPCST (SEQ ID NO:14) or a fragment thereof comprising ND. Modifications to such CRD fragments, e.g., by conservative substitution, are also within the scope described herein. In some embodiments, the MBL or a fragment thereof used in the microbe surface-binding domain of the engineered microbe-targeting molecules described herein can be a wild-type molecule or a recombinant molecule.

The exemplary sequences provided herein for the carbohydrate recognition domain of the engineered microbe-targeting molecules are not construed to be limiting. For example, while the exemplary sequences provided herein are derived from a human species, amino acid sequences of the same carbohydrate recognition domain in other species such as mice, rats, porcine, bovine, feline, and canine are known in the art and within the scope described herein.

In some embodiments, the nucleic acid encodes a carbohydrate recognition domain having greater than 50% homology, including greater than 60%, greater than 70%, greater than 80%, greater than 90% homology or higher, to a fragment of at least 50, at least 60, at least 70, at least 80, at least 90, at least 100, at least 150 contiguous amino acids or more, of any known carbohydrate-binding molecules (e.g., mannose-binding lectins).

In some embodiments, the entity comprises a polypeptide having at least 70%, 75%, 80%, 85%, 90%, 95%, 96%, 97%, 98%, 99%, or 100% identity to the CRD region of SEQ ID NO: 4. In some embodiments, the entity comprises a polypeptide having at least 70%, 75%, 80%, 85%, 90%, 95%, 96%, 97%, 98%, 99%, or 100% identity to the CRD and neck region of SEQ ID NO: 5. In some embodiments, the entity comprises a polypeptide having at least 70%, 75%, 80%, 85%, 90%, 95%, 96%, 97%, 98%, 99%, or 100% identity to the FcMBL of SEQ ID NO: 6. In some embodiments, the entity comprises a polypeptide having at least 70%, 75%, 80%, 85%, 90%, 95%, 96%, 97%, 98%, 99%, or 100% identity to the FcMBL region of SEQ ID NO: 7 or 8.

In some embodiments, the carbohydrate recognition domain can further comprise a neck region of the MBL with an amino acid sequence pdgdsslaaserkalgtemarikkwltfslgkq (SEQ ID NO: 15) or a fragment thereof. Without wishing to be bound by theory, the neck region can provide flexibility and proper orientation of the CRD to bind to a microbe surface. In some embodiments, the carbohydrate recognition domain can comprises a full-length CRD of MBL (SEQ ID NO. 4; termed as "CRD head") and the neck region thereof. The amino acid sequence encoding a full-length CRD of MBL and the neck region thereof is shown in SEQ ID NO. 5. The crystal structure of a native MBL "neck and CRD head" has been previously shown in Chang et al. (1994) J Mol Biol. 241:125-7. A skilled artisan can readily modify the identified CRD and fragments thereof to modulate its orientation and binding performance to carbohydrates on a microbe surface, e.g., by theoretical modeling and/or in vitro carbohydrate-binding experiments. In addition, based on the crystal structure of the native MBL "neck and CRD head", peptidomimetics that can effectively mimic at least a fragment of the CRD head and optionally the neck region can be also used as a carbohydrate recognition domain of the engineered microbe-targeting molecule or MBL molecule described herein. One of skill in the art can readily determine such peptidomimetic structure without undue experimentations, using any methods known in the art and the known crystal structure.

In some embodiments, the carbohydrate recognition domain of the microbe-targeting molecule can further comprise a portion of a carbohydrate-binding protein.

However, in some circumstances, complement or coagulation activation induced by a carbohydrate-binding protein or a fragment thereof can be undesirable depending on various applications, e.g., in vivo administration for or extracorporeal treatment of sepsis. In such embodiments, the portion of the carbohydrate-binding protein can exclude at least one of complement and coagulation activation regions. By way of example, when the carbohydrate-binding protein is mannose-binding lectin or a fragment thereof, the mannose-binding lectin or a fragment thereof can exclude at least one of the complement and coagulation activation regions located on the collagen-like region. In such embodiments, the mannose-binding lectin or a fragment thereof can exclude at least about one amino acid residue, including at least about two amino acid residues, at least about three amino acid residues, at least about four amino acid residues, at least about five amino acid residues, at least about six amino acid residues, at least about seven amino acid residues, at least about eight amino acid residues, at least about nine amino acid residues, at least about ten amino acid residues or more, around amino acid residue K55 or L56 of SEQ ID NO: 2. Exemplary amino sequences comprising K55 or L56 of SEQ ID NO: 2 that can be excluded from the engineered MBL molecule include, but are not limited to, EPGQGLRGLQGPPGKLGPPGNPGPSGS (SEQ ID NO. 16), GKLG (SEQ ID NO. 17), GPPGKLGPPGN (SEQ ID NO. 18), RGLQGPPGKL (SEQ ID NO. 19), GKLGPPGNPGPSGS (SEQ ID NO. 20), GLR-GLQGPPGKLGPPGNPGP (SEQ ID NO. 21), or any fragments thereof.

Additional CRDs, e.g., MBL CRDs, and methods of preparing them are described in, e.g., paragraphs 68-100 of WO2013/012924, which application is herein incorporated by reference in its entirety. In certain embodiments, the entity can be derived from an engineered microbe-targeting molecule, as described in International Application WO2011/090954 or WO2013/012924; the contents of which are incorporated by reference herein in their entireties.

In some embodiments, the entity comprises at least two microbe surface-binding domains (e.g., carbohydrate recognition domains), including at least three, at least four, at least five, at least six, at least seven, at least eight, at least nine, at least ten or more microbe surface-binding domains, linked together to form a multimeric microbe surface-binding domain or carbohydrate recognition domain. In such embodiments, the distances between microbe surface-binding domains (e.g., carbohydrate recognition domains) can be engineered to match with the distance between the binding sites on the target microbe surface.

A multimeric microbe surface-binding domain can have each of the individual microbe surface-binding domains the same. Alternatively, a multimeric microbe surface-binding domain can have at least one, at least two, or at least three microbe surface-binding domains different from the rest. In such embodiments, microbe surface-binding domains that share a common binding specificity for carbohydrates on a microbe surface can be used. By way of example only, the fibrinogen-like domain of several lectins has a similar function to the CRD of C-type lectins including MBL, and function as pattern-recognition receptors to discriminate pathogens from self. One of such lectins comprising the fibrinogen-like domain is serum ficolins.

Serum ficolins have a common binding specificity for GlcNAc (N-acetyl-glucosamine), elastin or GalNAc (N-acetyl-galactosamine). The fibrinogen-like domain is responsible for the carbohydrate binding. In human serum, two types of ficolin, known as L-ficolin (also called P35, ficolin L, ficolin 2 or hucolin) and H-ficolin (also called Hakata antigen, ficolin 3 or thermolabile b2-macro glycoprotein), have been identified, and both of them have lectin activity. L-ficolin recognises GlcNAc and H-ficolin recognises GalNAc. Another ficolin known as M-ficolin (also called P3 5-related protein, ficolin 1 or ficolin A) is not considered to be a serum protein and is found in leucocytes and in the lungs. L-ficolin and H-ficolin activate the lectin-complement pathway in association with MASPs. M-Ficolin, L-ficolin and H-ficolin has calcium-independent lectin activity. Accordingly, in some embodiments, an engineered microbe-targeting, e.g., an engineered MBL molecule, can comprise MBL and L-ficolin carbohydrate recognition domains, MBL and H-ficolin carbohydrate recognition domains, or a combination thereof.

Any art-recognized recombinant carbohydrate-binding proteins or carbohydrate recognition domains can also be used in the engineered microbe-targeting molecules. For example, recombinant mannose-binding lectins, e.g., but not limited to, the ones disclosed in the U.S. Pat. Nos. 5,270,199; 6,846,649; and U.S. Patent Application No. US 2004/0229212, the contents of which are incorporated herein by reference, can be used in constructing the compositions and in the methods described herein.

In one embodiment, the microbe-binding molecule comprises an MBL, a carbohydrate recognition domain of an MBL, or a genetically engineered version of MBL (FcMBL)

as described in International Application No. WO 2011/090954, filed Jan. 19, 2011, the content of which is incorporated herein by reference. Amino acid sequences for MBL and engineered MBL include, but are not limited to:

```
(i) MBL full length (SEQ ID NO: 1):
MSLFPSLPLLLLSMVAASYSETVTCEDAQKTCPAVIACSSPGINGFPGKDGRDGTKGEKG

EPGQGLRGLQGPPGKLGPPGNPGPSGSPGPKGQKGDPGKSPDGDSSLAASERKALQTEM

ARIKKWLTFSLGKQVGNKFFLTNGEIMTFEKVKALCVKFQASVATPRNAAENGAIQNLI

KEEAFLGITDEKTEGQFVDLTGNRLTYTNWNEGEPNNAGSDEDCVLLLKNGQWNDVPC

STSHLAVCEFPI (ii) MBL without the signal sequence (SEQ ID NO: 2):
ETVTCEDAQKTCPAVIACSSPGINGFPGKDGRDGTKGEKGEPGQGLRGLQGPPGKLGPP

GNPGPSGSPGPKGQKGDPGKSPDGDSSLAASERKALQTEMARIKKWLTFSLGKQVGNK

FFLTNGEIMTFEKVKALCVKFQASVATPRNAAENGAIQNLIKEEAFLGITDEKTEGQFVD

LTGNRLTYTNWNEGEPNNAGSDEDCVLLLKNGQWNDVPCSTSHLAVCEFPI (iii) Truncated MBL (SEQ ID NO: 3):
AASERKALQTEMARIKKWLTFSLGKQVGNKFFLTNGEIMTFEKVKALCVKFQASVATP

RNAAENGAIQNLIKEEAFLGITDEKTEGQFVDLTGNRLTYTNWNEGEPNNAGSDEDCVL

LLKNGQWNDVPCSTSHLAVCEFPI (iv) Carbohydrate recognition domain (CRD) of MBL (SEQ ID NO: 4):
VGNKFFLTNGEIMTFEKVKALCVKFQASVATPRNAAENGAIQNLIKEEAFLGITDEKTEG

QFVDLTGNRLTYTNWNEGEPNNAGSDEDCVLLLKNGQWNDVPCSTSHLAVCEFPI (v) Neck + Carbohydrate recognition domain of MBL (SEQ ID NO: 5):
PDGDSSLAASERKALQTEMARIKKWLTFSLGKQVGNKFFLTNGEIMTFEKVKALCVKF

QASVATPRNAAENGAIQNLIKEEAFLGITDEKTEGQFVDLTGNRLTYTNWNEGEPNNAG

SDEDCVLLLKNGQWNDVPCSTSHLAVCEFPI (vi) FcMBL.81 (SEQ ID NO: 6):
EPKSSDKTHTCPPCPAPELLGGPSVFLFPPKPKDTLMISRTPEVTCVVVDVSHEDPEVKFN

WYVDGVEVHNAKTKPREEQYDSTYRVVSVLTVLHQDWLNGKEYKCKVSNKALPAPIE

KTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGAPDG

DSSLAASERKALQTEMARIKKWLTFSLGKQVGNKFFLTNGEIMTFEKVKALCVKFQAS

VATPRNAAENGAIQNLIKEEAFLGITDEKTEGQFVDLTGNRLTYTNWNEGEPNNAGSDE

DCVLLLKNGQWNDVPCSTSHLAVCEFPI (vii) AKT-FcMBL (SEQ ID NO: 7):
AKTEPKSSDKTHTCPPCPAPELLGGPSVFLFPPKPKDTLMISRTPEVTCVVVDVSHEDPEV

KFNWYVDGVEVHNAKTKPREEQYDSTYRVVSVLTVLHQDWLNGKEYKCKVSNKALP

APIEKTISKAKGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQKSLSLSPGA

PDGDSSLAASERKALQTEMARIKKWLTFSLGKQVGNKFFLTNGEIMTFEKVKALCVKF

QASVATPRNAAENGAIQNLIKEEAFLGITDEKTEGQFVDLTGNRLTYTNWNEGEPNNAG

SDEDCVLLLKNGQWNDVPCSTSHLAVCEFPI (viii) FcMBL.111 (SEQ ID NO: 8):
EPKSSDKTHTCPPCPAPELLGGPSVFLFPPKPKDTLMISRTPEVTCVVVDVSHEDPEVKFN

WYVDGVEVHNAKTKPREEQYDSTYRVVSVLTVLHQDWLNGKEYKCKVSNKALPAPIE

KTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGATSKQ
```

```
                          -continued
VGNKFFLTNGEWITFEKVKALCVKFQASVATPRNAAENGAIQNLIKEEAFLGITDEKTEG

QFVDLTGNRLTYTNWNEGEPNNAGSDEDCVLLLKNGQWNDVPCSTSHLAVCEFPI
```

In some embodiments, a microbe-binding molecule comprises an amino acid sequence selected from SEQ ID NO: 1-SEQ ID NO: 8 or a microbe-binding fragment thereof, or a sequence at least 70%, 75%, 80%, 85%, 90%, 95%, 96%, 97%, 98%, 99%, or 100% identical thereto.

Without wishing to be bound by a theory, microbe-binding molecules comprising lectins or modified versions thereof can act as broad-spectrum pathogen binding molecules. Accordingly, microbes and/or microbial matter present in a sample can be bound using lectin-based microbe-binding molecules without identifying the microbe.

CD209: In some embodiments, the microbe-binding domain comprises the carbohydrate recognition domain of CD209 (Cluster of Differentiation 209) or a functional fragment thereof. CD209 is a protein which in humans is encoded by the CD209 gene. CD209 is also known as DC-SIGN (Dendritic Cell-Specific Intercellular adhesion molecule-3-Grabbing Non-integrin). DC-SIGN is a C-type lectin receptor present on both macrophages and dendritic cells. CD209 on macrophages recognizes and binds to mannose type carbohydrates, a class of Pathogen associated molecular patterns (PAMPs) commonly found on viruses, bacteria and fungi. This binding interaction activates phagocytosis. On myeloid and pre-plasmacytoid dendritic cells CD209 mediates dendritic cell rolling interactions with blood endothelium and activation of CD4+T cells, as well as recognition of pathogen haptens. CD209 is a C-type lectin and has a high affinity for the ICAM3 molecule. It binds various microorganisms by recognizing high-mannose-containing glycoproteins on their envelopes and especially functions as receptor for several viruses such as HIV and Hepatitis C. Binding to DC-SIGN can promote HIV and Hepatitis C virus to infect T-cells from dendritic cells. Thus binding to DC-SIGN is an important process for HIV infection. Besides functioning as an adhesion molecule, recent study has also shown that CD209 can initiate innate immunity by modulating toll-like receptors. DC-SIGN together with other C-type lectins is involved in recognition of tumors by dendritic cells. CD209 is also a potential engineering target for dendritic cell based cancer vaccine. Exemplary binding targets of CD209 include mannose and other sugars.

In some embodiments, the entity comprises the carbohydrate recognition domain of CD209 or a microbe-binding fragment thereof and comprises the amino acid sequence of SEQ ID NO: 24, or a sequence at least 70%, 75%, 80%, 85%, 90%, 95%, 96%, 97%, 98%, 99%, or 100% identical thereto.

CD209L: In some embodiments, the entity comprises the carbohydrate recognition domain of CD209L or a functional fragment thereof. CD209L is also called L-SIGN (liver/lymph node-specific intracellular adhesion molecules-3 grabbing non-integrin) and is a type II integral membrane protein that is 77% identical to CD209 antigen, an HIV g 120-binding protein. This protein, like CD209, efficiently binds both intercellular adhesion molecule 3 (ICAM3) and HIV-1 g 120, and enhances HIV-1 infection of T cells. The gene for L-SIGN is mapped to 19p 13.3, in a cluster with the CD209 and CD23/FCER2 genes. Multiple alternatively spliced transcript variants have been found for this gene, but the biological validity of some variants has not been determined. Exemplary binding targets of CD209L include mannose and other sugars.

In some embodiments, the entity comprises the carbohydrate recognition domain of L-SIGN or a microbe-binding fragment thereof and comprises the amino acid sequence of SEQ ID NO: 25, or a sequence at least 70%, 75%, 80%, 85%, 90%, 95%, 96%, 97%, 98%, 99%, or 100% identical thereto.

Pattern Recognition Receptors (PRRs): In some embodiments, the entity comprises a pattern recognition receptor or a functional fragment thereof. Pattern recognition receptors (PRRs) are a primitive part of the immune system. They are proteins expressed by cells of the innate immune system to identify pathogen-associated molecular patterns (PAMPs), which are associated with microbial pathogens or cellular stress, as well as damage-associated molecular patterns (DAMPs), which are associated with cell components released during cell damage. They are also called pathogen recognition receptors or primitive pattern recognition receptors because they evolved before other parts of the immune system, particularly before adaptive immunity. The microbe-specific molecules that are recognized by a given PRR are called pathogen-associated molecular patterns (PAMPs) and include bacterial carbohydrates (such as lipopolysaccharide or LPS, mannose), nucleic acids (such as bacterial or viral DNA or RNA), bacterial peptides (flagellin, ax21), peptidoglycans and lipoteichoic acids (from Gram positive bacteria), N-formylmethionine, lipoproteins and fungal glucans. Endogenous stress signals are called danger-associated molecular patterns (DAMPs) and include uric acid. Exemplary binding targets for PGRPs include peptidoglycan (PGN).

PRRs are classified according to their ligand specificity, function, localization and/or evolutionary relationships. On the basis of function, PRRs may be divided into endocytic PRRs or signaling PRRs. Signaling PRRs include the large families of membrane-bound Toll-like receptors and cytoplasmic NOD-like receptors. Endocytic PRRs promote the attachment, engulfment and destruction of microorganisms by phagocytes, without relaying an intracellular signal. These PRRs recognize carbohydrates and include mannose receptors of macrophages, glucan receptors present on all phagocytes and scavenger receptors that recognize charged ligands, are found on all phagocytes and mediate removal of apoptotic cells.

In some embodiments, the PRR is a CD14. CD14 acts as a co-receptor (along with the Toll-like receptor TLR4 and MD-2) for the detection of bacterial lipopolysaccharide (LPS). CD14 can bind LPS only in the presence of lipopolysaccharide-binding protein (LBP). Although LPS is considered its main ligand, CD14 also recognizes other pathogen-associated molecular patterns. Exemplary binding targets for CD14 include, but are not limited to, lipopolysaccharide (LPS), peptidoglycan (PGN), and lipoteichoic acid (LTA).

In some embodiments, the entity comprises a PRR or a microbe-binding fragment thereof and has the amino acid of SEQ ID NO: 26, or a sequence at least 70%, 75%, 80%, 85%, 90%, 95%, 96%, 97%, 98%, 99%, or 100% identical thereto.

Peptidoglycan recognition proteins: Peptidoglycan recognition proteins (PGRPs) are pattern recognition molecules that are conserved from insects to mammals and recognize bacteria and their unique cell wall component, peptidoglycan (PGN). PGRPs have at least one carboxy-terminal PGRP domain (approximately 165 amino acids long), which is homologous to bacteriophage and bacterial type 2 amidases. Insects have up to 19 PGRPs, classified into short (S) and long (L) forms. The short forms are present in the hemolymph, cuticle, and fat-body cells, and sometimes in epidermal cells in the gut and hemocytes, whereas the long forms are mainly expressed in hemocytes.

*Drosophila*, mosquito, and mammals have families of 13, 7, and 4 PGRP genes, respectively, and some of these genes are alternatively spliced. PGRPs are differentially expressed in various cells and tissues, their expression is often upregulated by bacteria, and they mediate host responses to bacterial infections. Insect PGRPs have four known effector functions that are unique for insects: activation of prophenoloxidase cascade, activation of Toll receptor, activation of Imd pathway, and induction of phagocytosis. One function, amidase activity, is shared by some insect and mammalian PGRPs, whereas antibacterial activity of some mammalian PGRPs is unique for mammals. The expression of insect PGRPs is often upregulated by exposure to bacteria.

Mammals have a family of four PGRPs, which were initially named PGRP-S, PGRP-L, and PGRP-Ia and PGRP-I0 (for 'short', 'long', or 'intermediate' transcripts, respectively), by analogy to insect PGRPs. Subsequently, the Human Genome Organization Gene Nomenclature Committee changed their symbols to PGLYRP-1, PGLYRP-2, PGLYRP-3, and PGLYRP-4, respectively. This terminology is also used for mouse PGRPs, and is beginning to be adopted for all vertebrate PGRPs. One mammalian PGRP, PGLYRP-2, is an N-acetylmuramoyl-L-alanine amidase that hydrolyzes bacterial peptidoglycan and reduces its proinflammatory activity; PGLYRP-2 is secreted from the liver into the blood and is also induced by bacteria in epithelial cells. The three remaining mammalian PGRPs are bactericidal proteins that are secreted as disulfide-linked homo- and hetero-dimers. PGLYRP-1 is expressed primarily in polymorphonuclear leukocyte granules and PGLYRP-3 and PGLYRP-4 are expressed in the skin, eyes, salivary glands, throat, tongue, esophagus, stomach, and intestine. These three proteins kill bacteria by interacting with cell wall peptidoglycan, rather than permeabilizing bacterial membranes as other antibacterial peptides do. Direct bactericidal activity of these PGRPs either evolved in the vertebrate (or mammalian) lineage or is yet to be discovered in insects. The mammalian PGLYRP-1, PGLYRP-2, PGLYRP-3, and PGLYRP-4 are also referred respectively as PGRP-L PGRP-2, PGRP-3 and PGRP-4 herein.

In some embodiments, the microbe-binding domain comprises a PGRP or a fragment thereof. In some embodiments, the microbe-binding domain comprises a PGRP or a fragment thereof from human, mouse, bovine, or beetle. In some embodiments, the microbe-binding domain comprises a PGRP or a fragment therefore comprising the amino acid sequence selected from the group consisting of SEQ ID NO: 27, SEQ ID NO: 29, SEQ ID NO: 31, SEQ ID NO: 32, SEQ ID NO: 34, and SEQ ID NO: 35.

From other species: In some embodiments, the entity comprises a carbohydrate recognition domain or a fragment (e.g. functional) thereof from shrimp. For example, the entity can comprise the carbohydrate recognition domain or a fragment thereof of Mj Lectin C or Mj Lectin B of shrimp. Exemplary binding targets for Mj Lectin C include the microbe cell wall. In some embodiments, the entity (e.g., entity comprising a microbe binding domain) comprises the amino acid sequence SEQ ID NO: 23 or SEQ ID NO: 36.

In some embodiments, the entity (e.g., entity comprising a microbe-binding domain) comprises a carbohydrate recognition domain or a fragment (e.g. functional) thereof from wheat germ agglutinin or WGA. WGA is a lectin that protects wheat (*Triticum* vulgaris) from insects, yeast and bacteria. An agglutinin protein, it binds to N-acetyl-D-glucosamine and Sialic acid. N-acetyl-D-glucosamine in the natural environment of wheat is found in the chitin of insects, and the cell membrane of yeast & bacteria. WGA is found abundantly-but not exclusively-in the wheat kernel. In mammals the N-acetyl-D-glucosamine that WGA binds to is found in cartilage and cornea, among other places. In those animals sialic acid is found in mucous membranes, e.g., the lining of the inner nose, and digestive tract. In solution, WGA exists mostly as a heterodimer of 38,000 Daltons. It is cationic at physiological pH. In some embodiments, the microbe-binding domain comprises a carbohydrate recognition domain or a fragment thereof from WGA and comprises the amino acid sequence of SEQ ID NO: 37.

In the tobacco hookworm, Manduca sexta, Peptidoglycan recognition proteins have been shown to function as stimulatory PRRs to enhance immune responses. Accordingly, in some embodiments, the microbe-binding domain comprises a PRR domain from Manduca sexta. In some embodiments, the microbe-binding domain comprises the amino acid sequence of SEQ ID NO: 30.

Without wishing to be bound by a theory, microbe-binding molecules described herein or modified versions thereof can act as broad-spectrum pathogen binding molecules.

Accordingly, microbes and/or microbial matter present in a test sample can be captured using microbe-binding molecules described herein without identifying the microbe, In some embodiments, the microbe surface-binding domain comprises an amino acid sequence selected from the sequences shown in Table 1 and combinations thereof.

TABLE 1

Some exemplary microbe surface-binding domain amino acid sequences

| | SEQ ID NO: | Sequence |
|---|---|---|
| MBL-antimicrobial-peptide | 22 | PDGDSSLAASERKALQTEMARIKKWLTFSLGKQVGNKF FLTNGEIMTFEKVKALCVKFQASVATPRNAAENGAIQNL IKEEAFLGITDEKTEGQFVDLTGNRLTYTNWNEGEPNNA GSDEDCVLLLKNGQWNDVPCSTSHLAVCEFPIGSAWWS YWWTQWASELGSPGSP |

TABLE 1-continued

Some exemplary microbe surface-binding domain amino acid sequences

| | SEQ ID NO: | Sequence |
|---|---|---|
| MjLectinC (Shrimp, *Marsupenaeus japonicus*) | 23 | ATCATFCTAQVNPCPNGYIVFWMDSVTPVCLKFAMYGK GTWTNLRMMCQAEGADLAKLDGNLHYQVIQYINNQRP DLQDEAFWIGGTDAASEGYWVWAMDGTQMDMSNPPW YPGQPNRGTIANYACLYTPDFMFHSCDNDRKIYAICQI |
| CD209 | 24 | ERLCHPCPWEWTFFQGNCYFMSNSQRNWHDSITACKEV GAQLVVIKSAEEQNFLQLQSSRSNRFTWMGLSDLNQEG TWQWVDGSPLLPSFKQYWNRGEPNNVGEEDCAEFSGN GWNDDKCNLAKFWICKKSAASCSRDE |
| CD209L | 25 | ERLCRHCPKDWTFFQGNCYFMSNSQRNWHDSVTACQE VRAQLVVIKTAEEQNFLQLQTSRSNRFSWMGLSDLNQE GTWQWVDGSPLSPSFQRYWNSGEPNNSGNEDCAEFSGS GWNDNRCDVDNYWICKKPAACFRDE |
| CD14 | 26 | TTPEPCELDDEDFRCVCNFSEPQPDWSEAFQCVSAVEVEI HAGGLNLEPFLKRVDADADPRQYADTVKALRVRRLTV GAAQVPAQLLVGALRVLAYSRLKELTLEDLKITGTMPPL PLEATGLALSSLRLRNVSWATGRSWLAELQQWLKPGLK VLSIAQAHSPAFSCEQVRAFPALTSLDLSDNPGLGERGL MAALCPHKFPAIQNLALRNTGMETPTGVCAALAAAGVQ PHSLDLSHNSLRATVNPSAPRCMWSSALNSLNLSFAGLE QVPKGLPAKLRVLDLSCNRLNRAPQPDELPEVDNLTLDG NPFLVPGTALPHEGSMNSGVVPACARSTLSVGVSGTLVL LQGARGFA |
| PGRP-1 (mouse) | 27 | CSFIVPRSEWRALPSECSSRLGHPVRYVVISHTAGSFCNS PDSCEQQARNVQHYHKNELGWCDVAYNFLIGEDGHVY EGRGWNIKGDHTGPIWNPMSIGITFMGNFMDRVPAKRA LRAALNLLECGVSRGFLRSNYEVKGHRDVQSTLSPGDQ LYQVIQSWEHYRE |
| PGRP-2 (Beetle) | 28 | PSPGCPTIVSKNRWGGQQASVQYTVKPLKYVIIHHTST PTCTNEDDCSRRLVNIQDYHMNRLDFDDIGYNFMIGGD GQIYEGAGWHKEGAHARGWNSKSLGIGFIGDFQTNLPSS KQLDAGKKFLECAVEKGEIEDTYKLIGARTVRPTDSPGT LLFREIQTWRGFTRNP |
| PGRP-4 (human) | 29 | DSSWNKTQAKQVSEGLQYLFENISQLTEKGLPTDVSTTV SRKAWGAEAVGCSIQLTTPVNVLVIHHVPGLECHDQTV CSQRLRELQAHHVHNNSGCDVAYNFLVGDDGRVYEGV GWNIQGVHTQGYNNISLGFAFFGTKKGHSPSPAALSAME NLITYAVQKGHLSSSYVQPLLGKGENCLAPRQKTSLKKA CPGVVPRSVWGARETHCPRMTLPAKYGIIIHTAGRTCNIS DECRLLVRDIQSFYIDRLKSCDIGYNFLVGQDGAIYEGVG WNVQGSSTPGYDDIALGITFMGTFTGIPPNAAALEAAQD LIQCAMVKGYLTPNYLLVGHSDVARTLSPGQALYNIIST WPHFKH |
| GBP-1 (Tobacco Hookworm) | 30 | PSPCLEVPDAKLEAIYPKGLRVSIPDDGYTLFAFHGKLNE EMEGLEAGHWSRDITKAKNGRWIFRDRNAKLKIGDKIY FWTYILKDGLGYRQDNGEWTVTGYVNEDGEPLDANFEP RSTASTAAPPQAGAGQAPGPSYPCELSVSEVSVPGFVCK GQMLFEDNFNKPLADGRIWTPEIMFPGEPDYPFNVYMK ETDNLHVGNGNLVIKPMPLVTAFGEDAIWKTLDLSDRC TGLLGTAQCKRDPSDAIIVPPIVTAKINTKKTFAFKYGRV EISAKMPRGDWLVPLIQLEPVNKNYGIRNYVSGLLRVAC VKGNTEYIKTLVGGPIMSEAEPYRTANLKEFISNEPWTNE FHNYTLEWSPDAITMAVDGIVYGRVTAPAGGFYKEANE QNVEAAARWIQGSNIAPFDDMFYISLGMDVGGVHEFPD EAINKPWKNTATKAMVNFWNARSQWNPTWLESEKALL VDYVRVYAL |
| PGRP-1 (human) | 31 | QETEDPACCSPIVPRNEWKALASECAQHLSLPLRYVVVS HTAGSSCNTPASCQQQARNVQHYHMKTLGWCDVGYNF LIGEDGLVYEGRGWNFTGAHSGHLWNPMSIGISFMGNY MDRVPTPQAIRAAQGLLACGVAQGALRSNYVLKGHRD VQRTLSPGNQLYHLIQNWPHYRSP |
| PGRP-3 short (human) | 32 | CPNIIKRSAWEARETHCPKMNLPAKYVIIIHTAGTSCTVS TDCQTVVRNIQSFHMDTRNFCDIGYHFLVGQDGGVYEG VGWHIQGSHTYGFNDIALGIAFIGYFVEKPPNAAALEAA QDLIQCAVVEGYLTPNYLLMGHSDVVNILSPGQALYNIIS TWPHFKH |

TABLE 1-continued

Some exemplary microbe surface-binding domain amino acid sequences

| | SEQ ID NO: | Sequence |
|---|---|---|
| PGRP (cow) | 33 | QDCGSIVSRGKWGALASKCSQRLRQPVRYVVVSHTAGS VCNTPASCQRQAQNVQYYHVRERGWCDVGYNFLIGED GLVYEGRGWNTLGAHSGPTWNPIAIGISFMGNYMHRVP PASALRAAQSLLACGAARGYLTPNYEVKGHRDVQQTLS PGDELYKIIQQWPHYRRV |
| PGRP-2 (human) | 34 | CPAIHPRCRWGAAPYRGRPKLLQLPLGFLYVHHTYVPAP PCTDFTRCAANMRSMQRYHQDTQGWGDIGYSFVVGSD GYVYEGRGWHWVGAHTLGHNSRGFGVAIVGNYTAALP TEAALRTVRDTLPSCAVRAGLLRPDYALLGHRQLVRTD CPGDALFDLLRTWPHF |
| PGRP-3 (human) | 35 | PTIVSRKEWGARPLACRALLTLPVAYIITDQLPGMQCQQ QSVCSQMLRGLQSHSVYTIGWCDVAYNFLVGDDGRVY EGVGWNIQGLHTQGYNNISLGIAFFGNKIGSSPSPAALSA AEGLISYAIQKGHLSPRYIQPLLLKEETCLDPQHPVMPRK VCPNIIKRSAWEARETHCPKMNLPAKYVIIHTAGTSCTV STDCQTVVRNIQSFHMDTRNFCDIGYHFLVGQDGGVYE GVGWHIQGSHTYGFNDIALGIAFIGYFVEKPPNAAALEA AQDLIQCAVVEGYLTPNYLLMGHSDVVNILSPGQALYNI ISTWPHFKH |
| MjLectinB (shrimp) | 36 | AWGGATATGPRKEAGDHVRNDVCPHPFVDINGRCLFVD NFAHLNWDAARTFCQGFQGDLVTLDEANLLGYIVDFIH QEGLTERSYWIGGSDRTSEGTWVWTDGSSVRMGTPTW GVDGETQQPTGGTSENCIGLHKDNFFFFNDFSCNNEMSL ICEFNM |
| WGA | 37 | RCGEQGSNMECPNNLCCSQYGYCGMGGDYCGKGCQN GACWTSKRCGSQAGGATCPNNHCCSQYGHCGFGAEYC GAGCQGGPCRADIKCGSQSGGKLCPNNLCCSQWGFCGL GSEFCGGGCQSGACSTDKPCGKDAGGRVCTNNYCCSK WGSCGIGPGYCGAGCQSGGCDAVFAGAITANSTLLAE |

In some embodiments, the microbe-binding molecule comprises the amino acid sequence selected from the group consisting of the sequences shown in Table 2 and any combination thereof.

TABLE 2

Some exemplary engineered microbe-binding molecule amino acid sequences

| | SEQ ID NO: | Sequence |
|---|---|---|
| FcMBL-peptide | 38 | AKTEPKSSDKTHTCPPCPAPELLGGPSVFLFPPKPKDTLMIS RTPEVTCVVVDVSHEDPEVKFNWYVDGVEVHNAKTKPRE EQYDSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS RWQQGNVFSCSVMHEALHNHYTQKSLSLSPGAPDGDSSL AASERKALQTEMARIKKWLTFSLGKQVGNKFFLTNGEIIVIT FEKVKALCVKFQASVATPRNAAENGAIQNLIKEEAFLGITD EKTEGQFVDLTGNRLTYTNWNEGEPNNAGSDEDCVLLLK NGQWNDVPCSTSHLAVCEFPIGSAWWSYWWTQWASELG SPGSP |
| FcMjLectinC (Shrimp, Marsupenaeus japonicus) | 39 | AKTEPKSSDKTHTCPPCPAPELLGGPSVFLFPPKPKDTLMIS RTPEVTCVVVDVSHEDPEVKFNWYVDGVEVHNAKTKPRE EQYDSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS RWQQGNVFSCSVMHEALHNHYTQKSLSLSPGAATCATFC TAQVNPCPNGYIVFWMDSVTPVCLKFAMYGKGTWTNLR MMCQAEGADLAKLDGNLHYQVIQYINNQRPDLQDEAFWI GGTDAASEGYWVWAMDGTQMDMSNPPWYPGQPNRGTIA NYACLYTPDFMFHSCDNDRKIYAICQI |
| FcCD209 | 40 | AKTEPKSSDKTHTCPPCPAPELLGGPSVFLFPPKPKDTLMIS RTPEVTCVVVDVSHEDPEVKFNWYVDGVEVHNAKTKPRE EQYDSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS |

TABLE 2-continued

Some exemplary engineered microbe-binding molecule amino acid sequences

| | SEQ ID NO: | Sequence |
|---|---|---|
| | | RWQQGNVFSCSVMHEALHNHYTQKSLSLSPGAERLCHPCP
WEWTFFQGNCYFMSNSQRNWHDSITACKEVGAQLVVIKS
AEEQNFLQLQSSRSNRFTWMGLSDLNQEGTWQWVDGSPL
LPSFKQYWNRGEPNNVGEEDCAEFSGNGWNDDKCNLAKF
WICKKSAASCSRDE |
| FcCD209L | 41 | AKTEPKSSDKTHTCPPCPAPELLGGPSVFLFPPKPKDTLMIS
RTPEVTCVVVDVSHEDPEVKFNWYVDGVEVHNAKTKPRE
EQYDSTYRVVSVLTVLHQDWLNGKEYKCKVSNKALPAPIE
KTISKAKGQPREPQVYTLPPSRDELTKNQVSLTCLVKGFYP
SDIAVEWESNGQPENNYKTTPPVLDSDGSFFLYSKLTVDKS
RWQQGNVFSCSVMHEALHNHYTQKSLSLSPGAERLCRHC
PKDWTFFQGNCYFMSNSQRNWHDSVTACQEVRAQLVVIK
TAEEQNFLQLQTSRSNRFSWMGLSDLNQEGTWQWVDGSP
LSPSFQRYWNSGEPNNSGNEDCAEFSGSGWNDNRCDVDN
YWICKKPAACFRDE |
| FcCD14 | 42 | AKTEPKSSDKTHTCPPCPAPELLGGPSVFLFPPKPKDTLMIS
RTPEVTCVVVDVSHEDPEVKFNWYVDGVEVHNAKTKPRE
EQYDSTYRVVSVLTVLHQDWLNGKEYKCKVSNKALPAPIE
KTISKAKGQPREPQVYTLPPSRDELTKNQVSLTCLVKGFYP
SDIAVEWESNGQPENNYKTTPPVLDSDGSFFLYSKLTVDKS
RWQQGNVFSCSVMHEALHNHYTQKSLSLSPGATTPEPCEL
DDEDFRCVCNFSEPQPDWSEAFQCVSAVEVEIHAGGLNLE
PFLKRVDADADPRQYADTVKALRVRRLTVGAAQVPAQLL
VGALRVLAYSRLKELTLEDLKITGTMPPLPLEATGLALSSL
RLRNVSWATGRSWLAELQQWLKPGLKVLSIAQAHSPAFSC
EQVRAFPALTSLDLSDNPGLGERGLMAALCPHKFPAIQNLA
LRNTGMETPTGVCAALAAAGVQPHSLDLSHNSLRATVNPS
APRCMWSSALNSLNLSFAGLEQVPKGLPAKLRVLDLSCNR
LNRAPQPDELPEVDNLTLDGNPFLVPGTALPHEGSMNSGV
VPACARSTLSVGVSGTLVLLQGARGFA |
| FcPGRP-1 (mouse) | 43 | AKTEPKSSDKTHTCPPCPAPELLGGPSVFLFPPKPKDTLMIS
RTPEVTCVVVDVSHEDPEVKFNWYVDGVEVHNAKTKPRE
EQYDSTYRVVSVLTVLHQDWLNGKEYKCKVSNKALPAPIE
KTISKAKGQPREPQVYTLPPSRDELTKNQVSLTCLVKGFYP
SDIAVEWESNGQPENNYKTTPPVLDSDGSFFLYSKLTVDKS
RWQQGNVFSCSVMHEALHNHYTQKSLSLSPGACSFIVPRS
EWRALPSECSSRLGHPVRYVVISHTAGSFCNSPDSCEQQAR
NVQHYHKNELGWCDVAYNFLIGEDGHVYEGRGWNIKGD
HTGPIWNPMSIGITFMGNFMDRVPAKRALRAALNLLECGV
SRGFLRSNYEVKGHRDVQSTLSPGDQLYQVIQSWEHYRE |
| FcPGRP-2 (Beetle) | 44 | AKTEPKSSDKTHTCPPCPAPELLGGPSVFLFPPKPKDTLMIS
RTPEVTCVVVDVSHEDPEVKFNWYVDGVEVHNAKTKPRE
EQYDSTYRVVSVLTVLHQDWLNGKEYKCKVSNKALPAPIE
KTISKAKGQPREPQVYTLPPSRDELTKNQVSLTCLVKGFYP
SDIAVEWESNGQPENNYKTTPPVLDSDGSFFLYSKLTVDKS
RWQQGNVFSCSVMHEALHNHYTQKSLSLSPGAPSPGCPTI
VSKNRWGGQQASQVQYTVKPLKYVIIHHTSTPTCTNEDDC
SRRLVNIQDYHMNRLDFDDIGYNFMIGGDGQIYEGAGWH
KEGAHARGWNSKSLGIGFIGDFQTNLPSSKQLDAGKKFLE
CAVEKGEIEDTYKLIGARTVRPTDSPGTLLFREIQTWRGFTR
NP |
| FcPGRP-4 (human) | 45 | AKTEPKSSDKTHTCPPCPAPELLGGPSVFLFPPKPKDTLMIS
RTPEVTCVVVDVSHEDPEVKFNWYVDGVEVHNAKTKPRE
EQYDSTYRVVSVLTVLHQDWLNGKEYKCKVSNKALPAPIE
KTISKAKGQPREPQVYTLPPSRDELTKNQVSLTCLVKGFYP
SDIAVEWESNGQPENNYKTTPPVLDSDGSFFLYSKLTVDKS
RWQQGNVFSCSVMHEALHNHYTQKSLSLSPGDSSWNKTQ
AKQVSEGLQYLFENISQLTEKGLPTDVSTTVSRKAWGAEA
VGCSIQLTTPVNVLVIHHVPGLECHDQTVCSQRLRELQAHH
VHNNSGCDVAYNFLVGDDGRVYEGVGWNIQGVHTQGYN
NISLGFAFFGTKKGHSPSPAALSAMENLITYAVQKGHLSSS
YVQPLLGKGENCLAPRQKTSLKKACPGVVPRSVWGARET
HCPRMTLPAKYGIIIHTAGRTCNISDECRLLVRDIQSFYIDRL
KSCDIGYNFLVGQDGAIYEGVGWNVQGSSTPGYDDIALGI
TFMGTFTGIPPNAAALEAAQDLIQCAMVKGYLTPNYLLVG
HSDVARTLSPGQALYNIISTWPHFKH |
| FcGBP-1 (Tobacco Hookworm) | 46 | AKTEPKSSDKTHTCPPCPAPELLGGPSVFLFPPKPKDTLMIS
RTPEVTCVVVDVSHEDPEVKFNWYVDGVEVHNAKTKPRE
EQYDSTYRVVSVLTVLHQDWLNGKEYKCKVSNKALPAPIE
KTISKAKGQPREPQVYTLPPSRDELTKNQVSLTCLVKGFYP |

TABLE 2-continued

Some exemplary engineered microbe-binding molecule amino acid sequences

| | SEQ ID NO: | Sequence |
|---|---|---|
| | | SDIAVEWESNGQPENNYKTTPPVLDSDGSFFLYSKLTVDKS RWQQGNVFScSVMHEALHNHYTQKSLSLSPGAPSPCLEVP DAKLEAIYPKGLRVSIPDDGYTLFAFHGKLNEEMEGLEAG HWSRDITKAKNGRWIFRDRNAKLKIGDKIYFWTYILKDGL GYRQDNGEWTVTGYVNEDGEPLDANFEPRSTASTAAPPQ AGAGQAPGPSYPCELSVSEVSVPGFVCKGQMLFEDNFNKP LADGRIWTPEIMFPGEPDYPFNVYMKETDNLHVGNGNLVI KPMPLVTAFGEDAIWKTLDLSDRCTGLLGTAQCKRDPSDA IIVPPIVTAKINTKKTFAFKYGRVEISAKMPRGDWLVPLIQL EPVNKNYGIRNYVSGLLRVACVKGNTEYIKTLVGGPIMSE AEPYRTANLKEFISNEPWTNEFHNYTLEWSPDAITMAVDGI VYGRVTAPAGGFYKEANEQNVEAAARWIQGSNIAPFDDM FYISLGMDVGGVHEFPDEAINKPWKNTATKAMVNFWNAR SQWNPTWLESEKALLVDYVRVYAL |
| FcPGRP-1 (human) | 47 | AKTEPKSSDKTHTCPPCPAPELLGGPSVFLFPPKPKDTLMIS RTPEVTCVVVDVSHEDPEVKFNWYVDGVEVHNAKTKPRE EQYDSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS RWQQGNVFScSVMHEALHNHYTQKSLSLSPGAQETEDPA CCSPIVPRNEWKALASECAQHLSLPLRYVVVSHTAGSSCNT PASCQQQARNVQHYHMKTLGWCDVGYNFLIGEDGLVYE GRGWNFTGAHSGHLWNPMSIGISFMGNYMDRVPTPQAIR AAQGLLACGVAQGALRSNYVLKHRDVQRTLSPGNQLYH LIQNWPHYRSP |
| FcPGRP-3short (human) | 48 | AKTEPKSSDKTHTCPPCPAPELLGGPSVFLFPPKPKDTLMIS RTPEVTCVVVDVSHEDPEVKFNWYVDGVEVHNAKTKPRE EQYDSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS RWQQGNVFScSVMHEALHNHYTQKSLSLSPGACPNIIKRS AWEARETHCPKMNLPAKYVIIHTAGTSCTVSTDCQTVVR NIQSFHMDTRNFCDIGYHFLVGQDGGVYEGVGWHIQGSHT YGFNDIALGIAFIGYFVEKPPNAAALEAAQDLIQCAVVEGY LTPNYLLMGHSDVVNILSPGQALYNIISTWPHFKH |
| FcPGRP (cow) | 49 | AKTEPKSSDKTHTCPPCPAPELLGGPSVFLFPPKPKDTLMIS RTPEVTCVVVDVSHEDPEVKFNWYVDGVEVHNAKTKPRE EQYDSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS RWQQGNVFSCSVMHEALHNHYTQKSLSLSPGAQDCGSIVS RGKWGALASKCSQRLRQPVRYVVVSHTAGSVCNTPASCQ RQAQNVQYYHVRERGWCDVGYNFLIGEDGLVYEGRGWN TLGAHSGPTWNPIAIGISFMGNYMHRVPPASALRAAQSLLA CGAARGYLTPNYEVKGHRDVQQTLSPGDELYKIIQQWPHY RRV |
| FcPGRP-2 (human) | 50 | AKTEPKSSDKTHTCPPCPAPELLGGPSVFLFPPKPKDTLMIS RTPEVTCVVVDVSHEDPEVKFNWYVDGVEVHNAKTKPRE EQYDSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS RWQQGNVFSCSVMHEALHNHYTQKSLSLSPGACPAIHPRC RWGAAPYRGRPKLLQLPLGFLYVHHTYVPAPPCTDFTRCA ANMRSMQRYHQDTQGWGDIGYSFVVGSDGYVYEGRGWH WVGAHTLGHNSRGFGVAIVGNYTAALPTEAALRTVRDTLP SCAVRAGLLRPDYALLGHRQLVRTDCPGDALFDLLRTWPH F |
| FcPGRP-3 (human) | 51 | AKTEPKSSDKTHTCPPCPAPELLGGPSVFLFPPKPKDTLMIS RTPEVTCVVVDVSHEDPEVKFNWYVDGVEVHNAKTKPRE EQYDSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS RWQQGNVFSCSVMHEALHNHYTQKSLSLSPGAPTIVSRKE WGARPLACRALLTLPVAYIITDQLPGMCCQQQSVCSQMLR GLQSHSVYTIGWCDVAYNFLVGDDGRVYEGVGWNIQGLH TQGYNNISLGIAFFGNKIGSSPSPAALSAAEGLISYAIQKGHL SPRYIQPLLLKEETCLDPQHPVMPRKVCPNIIKRSAWEARET HCPKMNLPAKYVIIIHTAGTSCTVSTDCQTVVRNIQSFEIMD TRNFCDIGYHFLVGQDGGVYEGVGWHIQGSHTYGFNDIAL GIAFIGYFVEKPPNAAALEAAQDLIQCAVVEGYLTPNYLLM GHSDVVNILSPGQALYNIISTWPHFKH |

TABLE 2-continued

Some exemplary engineered microbe-binding molecule amino acid sequences

| | SEQ ID NO: | Sequence |
|---|---|---|
| FcMjLectinB (shrimp) | 52 | AKTEPKSSDKTHTCPPCPAPELLGGPSVFLFPPKPKDTLMIS RTPEVTCVVVDVSHEDPEVKFNWYVDGVEVHNAKTKPRE EQYDSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS RWQQGNVFSCSVMHEALHNHYTQKSLSLSPGAAWGGAT ATGPRKEAGDHVRNDVCPHPFVDINGRCLFVDNFAHLNW DAARTFCQGEQGDLVTLDEANLLGYIVDFIHQEGLTERSY WIGGSDRTSEGTWVWTDGSSVRMGTPTWGVDGETQQPTG GTSENCIGLHKDNEFFENDFSCNNEMSLICEFNM |
| FcWGA | 53 | AKTEPKSSDKTHTCPPCPAPELLGGPSVFLEPPKPKDTLMIS RTPEVTCVVVDVSHEDPEVKFNWYVDGVEVHNAKTKPRE EQYDSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS RWQQGNVFSCSVMHEALHNHYTQKSLSLSPGARCGEQGS NMECPNNLCCSQYGYCGMGGDYCGKGCQNGACWTSKRC GSQAGGATCPNNHCCSQYGHCGFGAEYCGAGCQGGPCRA DIKCGSQSGGKLCPNNLCCSQWGFCGLGSEFCGGGCQSGA CSTDKPCGKDAGGRVCTNNYCCSKWGSCGIGPGYCGAGC QSGGCDAVFAGAITANSTLLAE |

Antimicrobial Peptides

In some embodiments, the entity comprises an antimicrobial peptide or a functional fragment thereof. In some embodiments the entity further comprises a carbohydrate recognition domain, e.g., at the N-terminus or C-terminus of the antimicrobial peptide. Further, the antimicrobial peptide can be linked directly or via a linker (e.g., a peptide of 1, 2, 3, 4, 5, 6, 7, 8, 9, 10 or more amino acids) to the carbohydrate recognition domain. In one embodiment, the antimicrobial peptide is linked to the C-terminal of the carbohydrate recognition domain.

Antimicrobial peptides (also called host defense peptides) are an evolutionarily conserved component of the innate immune response and are found among all classes of life. Fundamental differences exist between prokaryotic and eukaryotic cells that may represent targets for antimicrobial peptides. These peptides are potent, broad spectrum antibiotics which demonstrate potential as novel therapeutic agents. Antimicrobial peptides have been demonstrated to kill Gram negative and Gram positive bacteria (including strains that are resistant to conventional antibiotics), mycobacteria (including Mycobacterium tuberculosis), enveloped viruses, fungi and even transformed or cancerous cells. Unlike the majority of conventional antibiotics it appears as though antimicrobial peptides may also have the ability to enhance immunity by functioning as immunomodulators.

Antimicrobial peptides are a unique and diverse group of molecules, which are divided into subgroups on the basis of their amino acid composition and structure.

Antimicrobial peptides are generally between 12 and 50 amino acids. These peptides include two or more positively charged residues provided by arginine, lysine or, in acidic environments, histidine, and a large proportion (generally >50%) of hydrophobic residues. The secondary structures of these molecules follow 4 themes, including i) a-helical, it) P-stranded due to the presence of 2 or more disulfide bonds, iii) p-hairpin or loop due to the presence of a single disulfide bond and/or cyclization of the peptide chain, and iv) extended. Many of these peptides are unstructured in free solution, and fold into their final configuration upon partitioning into biological membranes. It contains hydrophilic amino acid residues aligned along one side and hydrophobic amino acid residues aligned along the opposite side of a helical molecule. This amphipathicity of the antimicrobial peptides allows to partition into the membrane lipid bilayer. The ability to associate with membranes is a definitive feature of antimicrobial peptides although membrane permeabilization is not necessary. These peptides have a variety of antimicrobial activities ranging from membrane permeabilization to action on a range of cytoplasmic targets.

The modes of action by which antimicrobial peptides kill bacteria is varied and includes disrupting membranes, interfering with metabolism, and targeting cytoplasmic components. The initial contact between the peptide and the target organism is electrostatic, as most bacterial surfaces are anionic, or hydrophobic, such as in the antimicrobial peptide Piscidin. Their amino acid composition, amphipathicity, cationic charge and size allow them to attach to and insert into membrane bilayers to form pores by 'barrel-stave', 'carpet' or 'toroidal-pore' mechanisms. Alternately, they can penetrate into the cell to bind intracellular molecules which are important for cell viability, intracellular binding models includes inhibition of cell wall synthesis, alteration of the cytoplasmic membrane, activation of autolysin, inhibition of DNA, RNA, and protein synthesis, and inhibition of certain enzymes. However, in many cases, the exact mechanism of killing is not known. In contrast to many conventional antibiotics these peptides appear to be bactericidal (bacteria killer) instead of bacteriostatic (bacteria growth inhibitor). In general the antimicrobial activity of these peptides is determined by measuring the minimal inhibitory concentration (MIC), which is the lowest concentration of drag that inhibits bacterial growth.

In addition to killing bacteria directly, antimicrobial peptides have been demonstrated to have a number of immunomodulator functions that can be involved in the clearance of infection, including the ability to alter host gene expression, act as chemokines and/or induce chemokine production, inhibiting lipopolysaccharide induced pro-inflammatory cytokine production, promoting wound healing, and modulating the responses of dendritic cells and cells of the adaptive immune response. Animal models indicate that host defense peptides are important for both prevention and clearance of infection.

Antimicrobial peptides are produced by all species, including peptides from bacteria, from fungi, Hydra, insects, (mastoparan, poneratoxin, cecropin, moricin, melittin and so on), frogs (magainin, dermaseptin and others), and mammals (for example, cathelicidins, defensins and protegrins).

In the competition of bacterial cells and host cells with the antimicrobial peptides, antimicrobial peptides preferentially interact with the bacterial cell to the mammalian cells, which enables them to kill microorganisms without being significantly toxic to mammalian cells. In some embodiments, the antimicrobial peptides have electrostatic interactions and hydrophobic interactions with the outer leaflet of a bacterial cell membrane.

Exemplary types of antimicrobial peptides include, but are not limited to, anionic peptides (e.g., maximin H5 from amphibians and dermcidin from humans), generally rich in glutamic and aspartic acids; linear cationic a-helical peptides (e.g., cecropins, andropin, moricin, ceratotoxin and melittin from insects, magainin, dermaseptin, bombinin, brevmin-1, esculentins and buforin II from amphibians, CAP 18 from rabbits, LL37 from humans), generally lack cysteine; cationic peptide enriched for specific amino acid (e.g., abaecin, apidaecins from honeybees, prophenin from pigs, indoilcidin from cattle), generally rich in proline, arginine, phenylalanine, glycine, or tryptophan; and anionic and cationic peptides that generally contain 1-3 disulfide bonds (e.g. brevinins (1 bond), protegrin from pig, and tachyplesins from horseshoe crabs (2 bonds), defensins from humans (3 bonds), drosomycin in fruit flies (more than 3 bonds). In some embodiments, the antimicrobial peptide is Pexiganan.

In some embodiments, the antimicrobial peptide comprises the amino acid sequence GSAWWSYWWTQ-WASELGSPGSP (SEQ ID NO: 54).

Small Molecules

In some embodiments, the entity is a small molecule. In some embodiments, the entity is an antibiotic, antineoplastic agent, antibacterial agent, antiviral agent, antiparasitic agent, or antifungal agent.

Drugs

In some embodiments, the entity is a drug, e.g., a small molecule or protein drug. In some embodiments, the entity is an antibiotic such as ampicillin, norfloxacin, rifampin, tigecycline, cefoperazone, furazolidone, silver sulfadiazine, dapsone, gemifloxacin, sulfadimidine, enoxacin, sulfisoxazole, ceftolozane, prontosil, sulfamerazine, sulfapyridine, grepafloxacin, sulfalene, sulfamethoxypyridazine, acetic acid/hydrocortisone, sulfabenzamide, sulfametrole, sulfametoxydiazine, ciridicatumtoxin B, sulfaphenazole, sulfamoxole, sulfametomidine, sulfathiourea, or sulfaperin.

In some embodiments, the drug comprises cationic, basic peptides such as polymyxin B or a component thereof. The drug can comprise, e.g., polymyxin B1, B1-I, B2, B3, or B6 or any combination thereof.

In some embodiments, the entity is an antiplatelet (e.g. aspirin, clopridigol, thienopyridine, or a P2Y12 inhibitor) and/or anticoagulant (e.g. Coumadin, acenocoumarol, phenprocoumondabigatran, apixaban and rivaroxaban) agent.

In some embodiments, the entity is an anti-cholesterol agent (e.g. statin) or anti-lipoprotein agent.

Nucleic Acids

In some embodiments, the entity can comprise at least one oligonucleotide. The sequence and length of the oligonucleotides can be configured according to the types of the substrate, binding density, and/or desired binding strength.

For example, if the substrate is a nucleic acid scaffold, e.g., a DNA scaffold, the oligonucleotide sequence of the substrate-binding domain can be designed such that it is complementary to a sub-sequence of the nucleic acid scaffold to where the substrate-binding domain can hybridize.

In some embodiments, the oligonucleotides can include aptamers. In embodiments, an aptamer is a single-stranded, partially single-stranded, partially double-stranded or double-stranded nucleotide sequence capable of specifically recognizing a selected non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art. The oligonucleotides including aptamers can be of any length, e.g., from about 1 nucleotide to about 100 nucleotides, from about 5 nucleotides to about 50 nucleotides, or from about 10 nucleotides to about 25 nucleotides. Generally, a longer oligonucleotide for hybridization to a nucleic acid scaffold can generate a stronger binding strength between the engineered microbe surface-binding domain and substrate.

Linkers

In some embodiments an entity comprises a linker, e.g., a linker that connects two domains of the entity. In some embodiments, the two domains are domains described herein. In some embodiments, the linker can directly or indirectly connect to one or more microbe surface-binding domains. Without limitations, in some embodiments, the linker can also provide binding sites to one or more microbes, microbial matter, and/or other target molecules. In such embodiments, the microbe-binding sites on the linker can bind to the same types and/or species of microbes as the microbes bind to a microbe-surface-binding domain. Alternatively or additionally, the microbe-binding sites on the linker can capture different types and/or species of microbes than the ones that bind to a microbe surface-binding domain described herein.

A linker can be attached to the N- or C-terminal of the entity (e.g., entity comprising a microbe surface-binding domain). Further, the linker can be linked directly or via another linker (e.g., a peptide of one, two, three, four, five, six, seven, eight, nine, ten or more amino acids) to the entity (e.g., entity comprising a microbe surface-binding domain). In one embodiment the linker is attached to the N-terminal of the entity (e.g., entity comprising a microbe surface-binding domain).

In some embodiments, the linker comprises a nucleic acid, e.g., DNA or RNA.

In some embodiments, a linker can be a chemical linker of any length. In some embodiments, chemical linkers can comprise a direct bond or an atom such as oxygen or sulfur, a unit such as NH, C(O), C(O)NH, SO, $SO_2$, $SO_2NH$, or a chain of atoms, such as substituted or unsubstituted C1-C6 alkyl, substituted or unsubstituted C2-C6 alkenyl, substituted or unsubstituted C2-C6 alkynyl, substituted or unsubstituted C6-C12 aryl, substituted or unsubstituted C5-C12 heteroaryl, substituted or unsubstituted C5-C12 heterocyclyl, substituted or unsubstituted C3-C12 cycloalkyl, where one or more methylenes can be interrupted or terminated by 0, S, S(0), S02, NH, or C(O). In some embodiments, the chemical linker can be a polymer chain (branched or linear).

Substrates, e.g., for attachment of entities using the methods herein

Many types of solid substrates can be used in accordance with this disclosure. In certain embodiments, solid substrates having chemically reactive surfaces (or surfaces that can be activated to provide chemically reactive surfaces) are used. In one embodiment, the surface is smooth. In other embodiments, the surface is not limited to any degree of surface roughness. In embodiments, the surface is porous.

In some embodiments, a porous solid substrate has a smaller pore size suitable for low-flux hemodialysis or a larger pore sizes suitable for high-flux hemodialysis. In some embodiments, the porous solid substrate has an average pore diameter of about 1-2, 2-5, 5-10, 10-20, 20-50, 50-100, 100-200, 200-500, or 500-1000 nm, or about 1-2, 2-5, 5-10, 10-20, 20-50, or 50-100 m. In some embodiment, the standard deviation of pore diameters in the substrate is less than about 50%, 20%, 10%, 5%, 2%, or 1% of the average pore diameter.

In some embodiments, the solid substrate is permeable, e.g., semipermeable. In some embodiments, the substrate is permeable to water, creatine, urea, potassium, phosphate, sodium, chloride, glucose, or any combination thereof. In some embodiments, a permeable solid substrate is permeable to molecules up to 1, 2, 5, 10, 20, 50, 100, 200, 500, 1,000, 2,000, 5,000, 10,000, or 20,000 daltons in size. In some embodiments, the substrate is permeable to beta-2-microglobulin (approximately 11,600 daltons). In some embodiments, the porous solid substrate is not permeable to molecules greater than 1,000, 2,000, 5,000, 10,000, 20,000, 50,000, or 100,000 daltons in size. In some embodiments, the porous solid substrate is not permeable to albumin (approximately 66,400 daltons). In some embodiments, the porous solid substrate is not permeable to cells. In some embodiments, the porous solid substrate does not comprise pores greater than approximately 0.1, 0.2, 0.5, 1, 2, or 5 microns in diameter. In some embodiments, the porous solid substrate does not comprise pores greater than approximately 0.5 microns in diameter.

In certain embodiments, the solid substrate can be a smooth surface, such as those described in PCT Application No. PCT/US2013/021056, filed on Jan. 10, 2013, the contents of which are incorporated by reference herein in its entirety.

The geometry of the solid substrate can be any shape, form, or configuration to suit the configuration of a variety of materials. Non-limiting examples of shapes, forms, and configurations that liquid repellant surfaces can take include generally spherical (e.g., beads), tubular (e.g., for a cannula, connector, catheter, needle, capillary tube, or syringe), planar (e.g., for application to a microscope slide, plate, wafer, film, or laboratory work surface), or arbitrarily shaped (e.g., well, well plate, Petri dish, tile, jar, flask, beaker, vial, test tube, column, container, cuvette, bottle, drum, vat, or tank). The solid substrate can be flexible or rigid.

The solid substrate material can be any material that is capable of modification as described herein. Many solid substrate materials are commercially available, or can be made by a variety of manufacturing techniques known in the art. Non-limiting examples of substrate surfaces that can be functionalized as described herein include, e.g., cellulose, modified cellulose (e.g., cellulose acetate), glass, polymers (e.g., polysulfone, polyarylethersulfone, polystyrene, polydimethylsiloxane ("PDMS"), polyamide, polycarbonate, polymethylmethacrylate, polyethylene terephthalate, polyvinyl chloride, poly(lactic-co-glycolitic acid, polyvinylpyrrolidone, polyacrylonitrile), etc.), polymers with plasticizers, (e.g. polyvinyl chloride with bis(2-ethylhexyl) phthalate, etc.), metals, metal alloys, metalloids, paper, plastics, various forms of carbon (e.g., diamond, graphite, fullerene, graphene, carbon nanotubes, black carbon, etc.), metal oxides, metalloid oxides, nonmetals, nonmetal oxides, and other ceramic materials, and the like.

Furthermore, a substrate can take the form of beads (including polymer microbeads, magnetic microbeads, superparamagnetic microbeads, superparamagnetic nanoparticles, and the like), filters, fibers, screens, mesh, fibers, hollow fibers, scaffolds, plates, channels, other substrates commonly utilized in assay formats, and any combinations thereof. Examples of substrates can include, but are not limited to, microparticles or microbeads, nanotubes, medical apparatuses (e.g., needles or catheters) or implants, microchips, filtration devices or membranes, hollow-fiber reactors, microfluidic devices, extracorporeal devices, and mixing elements (e.g., impellers, or mixers).

The substrate can be made of any material, e.g., any material that is compatible to a fluid to be processed. For example, the substrate can be made of any biocompatible material known in the art, e.g., but not limited to, TEFLON®, polysulfone, polypropylene, polystyrene, metal, metal alloy, polymer, plastic, glass, fabric, hydrogels, and any combinations thereof.

In certain environments, the solid substrate is selected to be compatible with the intended use of the device. For example, in medical applications such as medical devices, in embodiments the substrate material complies with FDA standards for safety and biocompatibility.

Suitable substrate materials can contain reactive surface moieties in its native form, or can be treated to provide suitable reactive moieties for linking with a surface-treating compound. Exemplary reactive surface moieties include oxygen-containing surface groups such as oxides, hydroxides, carboxyl, carbonyl, phenol, epoxy, quinone and lactone groups and the like; nitrogen-containing surface groups such as amino, C=N groups, azides, amides, nitrile groups, pyrrole-like structure and the like, sulfur-containing moieties such as thiols, and the like, and reactive carbon containing surface groups such as alkynes and alkenes.

Substrates can be treated to activate the substrate and render it amenable to modification using one or more activation techniques. Exemplary substrate treatments include acid or base (e.g., sodium hydroxide) treatment, oxidization, ammonization, plasma (e.g., as described herein), heat, ion, electron, electromagnetic, photon, such as UV-induced grafting (e.g., introduction of an initiator such as benzophenone, followed by polymerization of a functional group or polymer initiated at grafting sites), microwave treatment, and any combinations thereof. In some embodiments, the substrate is subjected to a plasma treatment and a second activation step.

In some embodiments, the solid substrate may be a roughened surface. In certain embodiments, the solid substrate may be a porous substrate. Some suitable roughened or porous substrates are described in PCT Application No. PCT/US2012/21928, filed on Jan. 19, 2012, the contents of which are incorporated by reference herein in its entirety.

In some embodiments, the solid substrate is flexible, such as for example, a flexible tube used in medical applications. In certain embodiments, the solid substrate can be a cross-linked polymer. For example, the substrate can be flexible PDMS, or flexible PVC, e.g., flexible PVC tubing.

In some embodiments, the substrate or a device comprising the substrate comprises a material that is damaged or degraded by organic solvents. For instance, the substrate or a device comprising the substrate can comprise polyurethane, polycarbonate, polyvinylchloride, polydimethylsiloxane, polyvinylpyrrolidone, potting compounds, polypropylene, polyethylene, polyethylene terephthalate, polymethylmethacrylate, rubber, nylon, polysulfone, polyethersulfone, polyarylethersulfone, cellulose acetate, thermoplastic elastomers, epoxy resins. In some embodiments, the methods herein avoid the use of an organic solvent and thus do not damage or degrade these materials.

In some embodiments, the substrate comprises less than 90, 80, 70, 60 or 50% polystyrene, e.g., does not comprise polystyrene. In some embodiments, the substrate comprises less than 90, 80, 70, 60 or 50% PLGA, e.g., does not comprise PLGA. In some embodiments, the substrate comprises less than 90, 80, 70, 60 or 50% silicone (e.g., PDMS), e.g., does not comprise silicone (e.g., PDMS). In some embodiments, the substrate comprises less than 90, 80, 70, 60 or 50% polyurethane or polyurethane copolymer, e.g., does not comprise a polyurethane or polyurethane copolymer.

In some embodiments, the substrate is sterilizable and autoclavable, e.g., has a glass transition temperature above 100C, 110C, 120C, 130C, 140C, or 150C. Examples of sterilizable and autoclavable substrates include polysulfone (which has a glass transition temperature of above 150C) and related polymers. In contrast, polystyrene has a glass transition temperature of 100C.

In some embodiments, the substrate comprises, is attached, or is situated in a device comprising, a mixing element. The mixing element can be a structural component that facilitates mixing a fluid (e.g., to increase contact with entities conjugated on the substrate). The mixing element can be suitable for low-shear mixing or high-shear mixing. In some embodiments, the mixing element can include an impeller. In some embodiments, the mixing element can include a mixer, e.g., spiral mixer or a static mixer.

In some embodiments, the substrate comprises, is attached, or is situated in a device comprising, a plurality of posts or pillars disposed in a flow conduit that disturb the flow of a fluid.

Plasmas and Plasma Generators

In some embodiments, the plasma generator used is a capacitively coupled plasma generator, e.g., a Model Nano from Diener. The plasma generator may utilize a 13.56 MHz radio frequency. In embodiments, the plasma generator comprises a chamber in which the plasma is produced. The plasma generator chamber can be of a size suitable for exposing one or more substrates to a plasma.

In some embodiments, the plasma generator or a portion thereof, e.g., the plasma generator chamber, is cleansed before treating the substrate. In some embodiments, the cleaning comprises a cycle with an empty chamber, e.g., a vacuum of below about 0.3, 0.2, 0.15, 0.14, 0.1, 0.05, or 0.01 mbar. In embodiments, the cleaning comprises a step of input of a gas, e.g., 02 gas, e.g., at a pressure of about 0.2, 0.25, 0.26, 0.3, 0.35, or 0.4 mbar. A plasma may then be generated from the gas, e.g., the 02 gas. The plasma may be generated for, e.g., at least 5, 10, 15, 20, 25, 30, 45, or 60 min. The plasma may be generated at, e.g., 30%, 40%, 50%, 60%, 70% power.

In some embodiments, the cleansing of the plasma generator chamber comprises chemical cleaning, e.g., as described in Cras et al., "Comparison of chemical cleaning methods of glass in preparation for silanization" Biosensors & Bioelectronics 14 (1999) 683-688. In embodiments, the cleansing step uses/has both acid and/or peroxide. In embodiments, the cleansing step uses mild etching (e.g., using a base or dilute hydrofluoric acid).

In some embodiments, the substrate is exposed to a gas such as $CO_2$ immediately before the plasma treatment, e.g., while the substrate is inside the chamber. For instance, the substrate can be exposed to the same gas that will be used to generate the plasma. In embodiments, the substrate is exposed to the gas for at least about 1, 2, 3, 4, 5, or 10 minutes. According to the non-limiting theory herein, this treatment can make distribution of PGMs more even on the substrate.

In some embodiments, the plasma used to generate PGMs is a $CO_2$, $O_2$, $N_2$, or $NH_4$ plasma. While not wishing to be bound by theory, in some embodiments a $CO_2$ plasma creates PGMs (e.g., carboxyl moieties) faster than an 02 plasma does, enabling the plasma treatment step to be shorter. In some embodiments, the plasma treatment step is less than about 10, 5, 4, 3, 2, or 1 minute. In some embodiments, the plasma treatment step is less than about 50, 40, 30, 20, or 10 seconds. In some embodiments, the plasma treatment step is about 1, 2, 3, 4, 5, or 10 minutes.

Coupling Reaction Conditions

This section describes various suitable ways to couple an entity to a plasma-generated moiety, e.g., on a solid substrate. In some embodiments, an activating moiety is used.

Activating moieties can be used to activate the components to be conjugated together (e.g., conjugating an entity to a solid substrate). Any suitable process and/or reagent for conjugation activation can be used, including those known in the art. Exemplary activating moieties include, but are not limited to, 1-Ethyl-3-[3-dimethylaminopropyl]carbodiimide hydrochloride (EDC or EDAC), hydroxybenzotriazole (HOBT), N-Hydroxysuccinimide (NHS), 2-(1H-7-Azabenzotriazol-1-yl)--1,1,3,3-tetramethyl uronium hexafluorophosphate methanaminium (HATU), N,N'-diisopropylcarbodiimide, N,N'-Dicyclohexylcarbodiimide, sulfosuccinimidyl 4-(N-maleimidomethyl)cyclohexane-1-carboxylate, imidoester, sulfonyl chloride, NHS ester, fluorophenyl ester, fluorobenzene, isocyanate, isothiocyanate, maleimide, halacetyl, pyridyl disulfide, alkoxyamine, diazerine, periodate, silanization, surface activation through plasma treatment, and the like. In one embodiment, EDC is used to conjugate a microbe-binding molecule (e.g., FcMBL) to a solid substrate surface.

In some embodiments, the reaction mixture comprises a crosslinking agent according to Table 3 below.

Any reactive group, including those known in the art, can be used for coupling. For example, various surface reactive groups can be used for surface coupling including, but not limited to, alkyl halide, aldehyde, azide, amino, bromo or iodoacetyl, carboxyl, alkyne, alkene, hydroxyl, epoxy, ester, silane, thiol, and the like.

In some embodiments, the coupling reaction is carried out in a buffer. Exemplary buffers include 2-(N-morpholino) ethanesulfonic acid (MES), piperazine-N,N'-bis(2-ethanesulfonic acid) (PIPES), N-(2-Acetamido)-2-aminoethanesulfonic acid (ACES), 3-Morpholino-2-hydroxypropanesulfonic acid (MOPSO), N-(2-Acetamido)-2-iminodiacetic acid (ADA), 3-(N-morpholino) propanesulfonic acid (MOPS), N,N-Bis(2-hydroxyethyl)-2-aminoethanesulfonic acid (BES), 2-[[1,3-dihydroxy-2-(hydroxymethyl)propan-2-yl]amino]ethanesulfonic acid (TES), 4-(2-hydroxyethyl)-1-piperazineethanesulfonic acid (HEPES), N-Cyclohexyl-2-aminoethanesulfonic acid (CHES), N-cyclohexyl-3-aminopropanesulfonic acid (CAPS), 3-[4-(2-Hydroxyethyl)-1-piperazinyl]propanesulfonic acid (HEPPS), borate, acetate, carbonate, and phosphate.

In some embodiments, the methods herein allow one to avoid using a crosslinking agent such as an isocyanate, glutaraldahyde, formaldehyde, peroxide, phosphonium, or a crosslinking agent of one of the classes of Table 3:

TABLE 3

Crosslinking agents

| Crosslinking target | Crosslinker reactive groups, features |
|---|---|
| Amine-to-amine | NHS esters |
| | Imidoesters |
| Sulfhydryl-to-sulfhydryl | Maleimides |
| Nonselective | Aryl azides |
| Amine-to-sulfhydryl | NHS ester/maleimide |
| | NHS ester/pyridyldithiol |
| | NHS esters/haloacetyl |
| Amine-to-nonselective | NHS ester/aryl azide |
| | NHS ester/diazirine |
| Amine to carboxyl | carbodiimide |
| Sulfhydryl-to-carbohydrate | Maleimide/hydrazide |
| | Pyridyldithiol/hydrazide |
| Amine-to-DNA | NHS ester/psoralen |

Accordingly, in some embodiments, the methods herein do not include contacting the substrate or entity with a crosslinking agent such as an isocyanate, glutaraldahyde, formaldehyde, peroxide, phosphonium, or a crosslinking agent of Table 3. Likewise, in some embodiments, the compositions herein contain less than $1\times10^{16}$, $1\times10^{15}$, $1\times10^{14}$, $1\times10^{13}$, $1\times10^{12}$, $1\times10^{11}$, $1\times10^{10}$, $1\times10^{9}$, $1\times10^{8}$, $1\times10^{7}$, $1\times10^{6}$, $1\times10^{5}$, $1\times10^{4}$, $1\times10^{3}$, 100, 10, or 1 molecule per $cm^2$ of a crosslinking agent such as an isocyanate, glutaraldahyde, formaldehyde, peroxide, phosphonium, or a crosslinking agent of Table 3.

Masking Entities

In embodiments, the compositions and methods herein involve a masking entity. Without being limited by theory, a masking entity can bind to an entity, e.g., an opsonin, e.g., an MBL, e.g., FcMBL, and help the entity retain activity by masking at least a portion of the entity from a reactant, e.g., an activating moiety, crosslinking agent, or free radical. In some embodiments, the masking entity binds to an active site or binding surface of the entity (e.g., a polypeptide). The masking entity may comprise, e.g., a divalent ion such as calcium. The masking entity may also comprise, e.g., a sugar such as glucose. The masking entity may comprise a polypeptide, nucleic acid (e.g., DNA or RNA), lipid, carbohydrate, or small molecule.

In some embodiments, the masking entity comprises a blocking agent described in International Application WO2014144325, which is herein incorporated by reference in its entirety.

Examples of a saccharide-based masking entities include, without limitations, hexose (e.g., glucose), maltose, mannose, N-acetyl-muramic acid, amino sugars (e.g., galactosamine, glucosamine, sialic acid, N-acetylglucosamine), sulfosugars (e.g., sulfoquinovose), trehalose, cellobiose, lactose, lactulose, sucrose, fructo-oligosaccharides, cellulose, chitin, or any combinations thereof. In some embodiments, a saccharide-based blocking agent can be glucose, maltose, N-acetyl-muramic acid, or any combinations thereof. In one embodiment, a saccharide-based blocking agent can comprise glucose. In one embodiment, a saccharide-based blocking agent can comprise mannose.

Uses, e.g., for Hemodialysis or Hemofiltration

The substrates made by the methods described herein can be used in/as devices for capturing a target moiety, such as a soluble or suspended target moiety in a liquid. Non-limiting examples of target moieties include a microbe and/or microbial matter, which can optionally be present in a bodily fluid, e.g., blood. In an embodiment, the devices can bind or capture at least one target moiety, such as an intact microbe, and/or microbial matter.

In one aspect, the device is for capturing a microbe, microbial matter and/or a target molecule comprising (i) a chamber with an inlet and an outlet, (ii) at least one capture element disposed in the chamber between the inlet and outlet, wherein the capture element has on its surface at least one entity, e.g., a microbe-binding molecule described herein. The chamber may have, e.g., a circular, rectangular, square, oval, triangular, polygonal or any irregular-shaped cross-section.

In some embodiments, the device described herein can be integrated with a shunt system or adapted to connect to a shunt system. The shunt system can comprise a first end, e.g., for collecting a fluid such as blood, and a second end, e.g., for returning the filtered fluid such as blood to a patient. In such embodiments, a fluid flowing through the device can have any microbes, if present, bound to an entity, e.g., microbe-binding molecules, and get filtered before returning to a patient. This device can be designed to be portable, e.g., for emergency applications such as military field applications. A standard shunt can be inserted into a jugular vein or femoral vein with a device attached to the shunt. The device can be disposable such that a patient can change the device regularly to maintain microbe-capture efficiency until he/she is transported to a hospital for treatment.

In some embodiments, the device is a hemodialysis device that has a membrane area (A) and a membrane permeability coefficient $K_0$ for the solute in question. Dialyzer efficiency is usually expressed as the $K_0A$—the product of permeability coefficient and area. In some embodiments, a dialyzer described herein has a membrane surface area of 0.3 to 2.2 square meters, e.g., 0.8 to 2.2 square meters, and values of $K_0A$ range from about 500 to 1500 mL/min. $K_0A$, expressed in mL/min, can be thought of as the maximum clearance of a dialyzer at very high blood and dialysate flow rates.

Non-limiting examples of bacteria that can be selective bound by substrates modified in accordance with the present disclosure include members of the genus selected from the group consisting of *Actinobacillus* (e.g., *Actinobacillus actinomycetemcomitans*), *Acinetobacter* (e.g., *Acinetobacter baumannii*), *Aeromonas*, *Bordetella* (e.g., *Bordetella pertussis*, *Bordetella bronchiseptica*, and *Bordetella parapertussis*), *Brevibacillus*, *Brucella*, *Bacteroides* (e.g., *Bacteroides fragilis*), *Burkholderia* (e.g., *Burkholderia cepacia* and *Burkholderia pseudomallei*), *Borelia* (e.g., *Borelia burgdorferi*), *Bacillus* (e.g., *Bacillus anthracis* and *Bacillus subtilis*), *Campylobacter* (e.g., *Campylobacter jejuni*), *Capnocytophaga*, *Cardiobacterium* (e.g., *Cardiohacterium hominis*), *Citrobacter*, *Clostridium* (e.g., *Clostridium tetani* or *Clostridium difficile*), *Chlamydia* (e.g., *Chlamydia trachomatis*, *Chlamydia pneumoniae*, and *Chlamydia* psiffaci), *Eikenella* (e.g., *Eikenella corrodens*), *Enterobacter*, *Enterococcus*, *Escherichia* (e.g., *Escherichia coli*), *Francisella* (e.g., *Francisella tularensis*), *Fusobacterium*, *Flavobacterium*, *Haemophilus* (e.g., *Haemophilus ducreyi* or *Haemophilus influenzae*), *Helicobacter* (e.g., *Helicobacter pylori*), *Kingella* (e.g., *Kingella kingae*), *Klebsiella* (e.g., *Klebsiella pneumoniae*), *Lactobacillus*, *Legionella* (e.g., *Legionella*

*pneumophila*), *Listeria* (e.g., *Listeria monocytogenes*), *Leptospirae*, *Moraxella* (e.g., *Moraxella catarrhalis*), *Morganella*, *Mycoplasma* (e.g., *Mycoplasma hominis* and *Mycoplasma pneumoniae*), *Mycobacterium* (e.g., *Mycobacterium tuberculosis* or *Mycobacterium leprae*), *Neisseria* (e.g., *Neisseria gonorrhoeae* or *Neisseria meningitidis*), *Nocardia*, *Pasteurella* (e.g., *Pasteurella multocida*), *Proteus* (e.g., *Proteus vulgaris* and *Proteus* mirablis), *Prevotella*, *Plesiomonas* (e.g., *Plesiomonas shigelloides*), *Pseudomonas* (e.g., *Pseudomonas aeruginosa*), *Providencia*, *Rickettsia* (e.g., *Rickettsia rickettsii* and *Rickettsia typhi*), *Stenotrophomonas* (e.g., *Stenotrophomonas maltophila*), *Staphylococcus* (e.g., *Staphylococcus aureus* and *Staphylococcus epidermidis*), *Streptococcus* (e.g., *Streptococcus viridans*, *Streptococcus pyogenes* (group A), *Streptococcus agalactiae* (group B), *Streptococcus bovis*, and *Streptococcus pneumoniae*), *Streptomyces* (e.g., *Streptomyces hygroscopicus*), *Salmonella* (e.g., *Salmonella enteriditis*, *Salmonella typhi*, and *Salmonella typhimurium*), *Serratia* (e.g., *Serratia marcescens*), *Shigella*, *Spirillum* (e.g., *Spirillum* minus), *Treponema* (e.g., *Treponema pallidum*), *Veillonella*, *Vibrio* (e.g., *Vibrio cholerae*, *Vibrio parahemolyticus*, and *Vibrio* vulnifrcus), *Yersinia* (e.g., *Yersinia enterocolitica*, *Yersinia pestis*, and *Yersinia pseudotuberculosis*), *Xanthomonas* (e.g., *Xanthomonas maltophilia*) and combinations thereof.

A substrate modified according to the present disclosure can selectively bind various types of fungi. Non-limiting examples of fungi selectively bound by modified surfaces include members of the genus *Aspergillus* (e.g., *Aspergillus flavus*, *Aspergillus fumigatus*, *Aspergillus glaucus*, *Aspergillus nidulans*, *Aspergillus niger*, and *Aspergillus terreus*), *Blastomyces dermatitidis*, *Candida* (e.g., *Candida albicans*, *Candida glabrata*, *Candida tropicalis*, *Candida parapsilosis*, *Candida krusei*, and *Candida* gillermondii), *Coccidioides immitis*, *Cryptococcus* (e.g., *Cryptococcus neoformans*, *Cryptococcus albidus*, and *Cryptococcus laurentii*), *Fusarium*, *Histoplasma capsulatum* var. *capsulatum*, *Histoplasma capsulatum* var. duboisii, *Mucor*, *Paracoccidioides brasiliensis*, *Pneumocystis*, *Saccharomyces*, *Sporothrix schenckii*, *Absidia corymbifera*; *Rhizomucor pusillus*, *Rhizopus* arrhizous, and combinations thereof.

A substrate modified according to the present disclosure can also selectively bind various types of viruses and virus-like particles. In one or more embodiments, the virus selectively bound by these surfaces is selected from the group consisting of dsDNA viruses, ssDNA viruses, dsRNA viruses, (+)ssRNA viruses, (−)ssRNA viruses, ssRNA-RT viruses, dsDNA-RT viruses, and combinations thereof. Non-limiting examples of viruses repelled and/or selective bound by surfaces modified in accordance with the present disclosure include cytomegalovirus (CMV), dengue, Epstein-Barr, Hantavirus, human T-cell lymphotropic vims (HTLV I/II), Parvovirus, hepatitides (e.g., hepatitis A, hepatitis B, and hepatitis C), human papillomavirus (HPV), human immunodeficiency virus (HIV), acquired immunodeficiency syndrome (AIDS), respiratory syncytial virus (RSV), Varicella zoster, West Nile, Ebola, Zika, herpes, polio, smallpox, yellow fever, rhinovirus, coronavirus, Orthomyxoviridae (influenza viruses) (e.g., Influenzavirus A, Influenzavirus B, Influenzavirus C, Isavirus and Thogotovirus), and combinations thereof.

In still another embodiment, a substrate modified according to the present disclosure is capable of selectively binding particles in suspension or solution without causing surface adhesion, surface-mediated clot formation, coagulation, fouling, or aggregation. Non-limiting examples of a particles in suspension or solution include cells (e.g., normal cells, diseased cells, parasitized cells, cancer cells, foreign cells, stem cells, and infected cells), microorganisms (e.g., viruses, virus-like particles, bacteria, bacteriophages), proteins and cellular components (e.g., cell organelles, cell fragments, cell membranes, exosomes, cell membrane fragments, viruses, virus-like particles, bacteriophage, cytosolic proteins, secreted proteins, signaling molecules, embedded proteins, nucleic acid/protein complexes, nucleic acid precipitants, chromosomes, nuclei, mitochondria, chloroplasts, flagella, biominerals, protein complexes, and minicells).

Uses, e.g., for Assays and Diagnostics

In some embodiments, a device described herein (e.g., a device made according to a method herein) is used for diagnosis, e.g., of sepsis or an infectious disease. In embodiments, the device comprises a solid substrate attached to an entity, where the entity binds a microbe or microbial matter. In some embodiments, a diagnostic device is produced by plasma treating a solid substrate, contacting the solid substrate with an entity, contacting the solid substrate with a biological sample, and determining whether a microbe in the biological sample binds to the entity. The diagnostic method or system may also comprise a detectable label.

In some aspects, this disclosure provides a kit comprising: a solid substrate attached (e.g., covalently) to an entity such as a microbe targeting molecule, e.g., an unlabeled microbe-targeting molecule, e.g., one comprising a lectin or carbohydrate-binding portion thereof, e.g., one comprising MBL, e.g., an FcMBL; and a detectable label conjugated to a targeting agent specific for a microbe.

In some aspects, this disclosure provides a method of detecting a microbe or microbial matter, comprising contacting the microbe or microbial matter with a solid substrate attached to a microbe targeting molecule, e.g., an unlabeled microbe-targeting molecule, e.g., one comprising a lectin or carbohydrate-binding portion thereof, e.g., one comprising MBL, e.g., an FcMBL; and a detectable label conjugated to a targeting agent specific for the microbe or microbial matter.

In some aspects, this disclosure provides a composition comprising: a microbe or microbial matter; a solid substrate attached to a microbe targeting molecule, e.g., an unlabeled microbe-targeting molecule, e.g., one comprising a lectin or carbohydrate-binding portion thereof, e.g., one comprising MBL, e.g., an FcMBL; and a detectable label conjugated to a targeting agent specific for the microbe.

In some embodiments of the kits, methods, and compositions herein, the detectable label comprises an enzyme. In some embodiments, the enzyme is horseradish peroxidase (HRP). In some embodiments, the targeting agent specific for the microbe comprises an engineered microbe-targeting molecule, an antibody molecule, a lectin, or MBL (e.g., human MBL). In embodiments, the solid substrate is attached to the microbe-targeting molecule by a method described herein, e.g., a method comprising plasma treatment of the substrate. In embodiments, the solid substrate attached to the microbe-targeting molecule is a composition described herein, e.g., comprises little or none of a cross-linking agent such as a silane. In some embodiments, the kit or composition further comprises, or the method further comprises contacting the enzyme with, a substrate for the enzyme, e.g., TMB (3,3',5,5'-tetramethylbenzidine).

Some embodiments of any aspects of the kits described herein can further comprise an additional agent. For example, in some embodiments where the entity, e.g., microbe-targeting molecule attached to the substrate is unlabeled, the kit can further comprise one or more detectable labels conjugated to a targeting agent specific for a microbe, e.g., without limitations, one or more embodiments of an engineered microbe-targeting molecule or a fragment thereof, an antibody molecule specific for at least one microbe (e.g., antibody molecules specific for Gram-positive microbes such as anti-LTA antibody molecules, antibody molecules specific for Gram-negative microbes such as anti-LPS antibody molecules, or antibody molecules specific for fungus, and any combinations thereof). The use of an additional targeting agent specific for a microbe conjugated to a detectable label can not only facilitate the detection of microbes or pathogens, but can also increase the specificity of the detection for a microbe or a pathogen.

In any aspects of the kits provided herein, when the detectable label includes an enzyme (e.g., horseradish peroxidase, alkaline phosphatase and any others suitable for colorimetric detection), the kits can further comprise one or more containers containing an enzyme substrate that produces a color change in the presence of the enzyme. One of skill in the art can readily recognize an appropriate enzyme substrate for any art-recognized enzymes used for colorimetric detection. By way of example only, an exemplary substrate for alkaline phosphatase can include BCIP/NBT (5-bromo-4-chloro-3-indolyl-phosphate/nitro blue tetrazolium) or PNPP (p-Nitrophenyl Phosphate); an exemplary substrate for horseradish peroxidase can include TMB (3,3', 5,5'-tetramethylbenzidine).

In some embodiment, the diagnostic devices described herein provide a signal-to-noise ratio that exceeds 3, 5, 10, 100, 1000, 10,000, 100,000, or 1,000,000.

Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, bioluminescent moieties, and the like. A label can be a composition detectable by spectroscopic, photochemical, biochemical, immunochemical, electrical, optical or chemical means.

A wide variety of fluorescent reporter dyes can be used. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350; Alexa Fluor 430; Alexa Fluor 488; Alexa Fluor 532; Alexa Fluor 546; Alexa Fluor 568; Alexa Fluor 594; Alexa Fluor 633; Alexa Fluor 647; Alexa Fluor 660; Alexa Fluor 680; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAG CBQCA; ATTO-TAG FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO-1; BOBO-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 6501665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO-1; BO-PRO-3; Brilliant Sulphoflavin FF; Calcein; Calcein Blue; Calcium Crimson; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue; Cascade Yellow; Catecholamine; CFDA; CFP (Cyan Fluorescent Protein); Chlorophyll; Chromomycin A; Chromomycin A; CMFDA; Coelenterazine; Coelenterazine cp; Coelenterazine f, Coelenterazine fcp; Coelenterazine h; Coelenterazine hcp; Coelenterazine ip; Coelenterazine 0; Coumarin Phalloidin; CPM Methylcoumarin; CTC; Cy2; Cy3.1 8; Cy3.5; Cy3; Cy5.1 8; Cy5.5; Cy5; Cy7; Cyan GFP; cyclic AMP Fluorosensor (FiCRhR); d2; Dabcyl; Dansyl; Dansyl Amine; Dansyl Cadaverine; Dansyl Chloride; Dansyl DUPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydorhodamine 123 (DHR); DiO (DiOC 18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-l); Euchrysin; Europium (111) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43.TM.; FM 4-46; Fura Red (high pH); Fura-2, high calcium; Fura-2, low calcium; Genacryl Brilliant Red B; Genacryl Brilliant Yellow IOGF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green.TM.; Oregon Green 488-X; Oregon Green 488; Oregon Green 500; Oregon Green 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R;

PhotoResist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP.TM.; sgBFP (super glow BFP); sgGFP; sgGFP (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red; Texas Red-X conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (Tetramethyl-RodamineIsoThioCyanate); True Blue; TruRed; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

Other exemplary detectable labels include luminescent, chemiluminescent, electrochemiluminescent, and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference. In some embodiments, the detectable label is a fluorophore or a quantum dot.

Means of detecting such labels are well known to those of skill in the art. Exemplary detection methods include, but are not limited to, spectrometry, fluorometry, microscopy imaging, voltammetry, immunoassay, and the like. Thus, for example, radiolabels can be detected using photographic film or scintillation counters, fluorescent markers can be detected using a photo-detector to detect emitted light. Enzymatic labels can be detected, e.g., by providing the enzyme with an enzyme substrate and detecting the reaction product produced by the action of the enzyme on the enzyme substrate, and colorimetric labels can be detected by visualizing the colored label. In some embodiments, a microbe or microbial matter is detected through use of one or more enzyme assays, e.g., enzyme-linked assay (ELISA). Numerous enzyme assays can be used to provide for detection. Examples of such enzyme assays include, but are not limited to, beta-galactosidase assays, peroxidase assays, catalase assays, alkaline phosphatase assays, and the like. In some embodiments, enzyme assays can be configured such that an enzyme will catalyze a reaction involving an enzyme substrate that produces a fluorescent product. Additionally, imaging analysis can be performed via automated image acquisition and analysis.

In some embodiments, a detectable label can be a "smart label", which is undetectable when conjugated to the entity (e.g., entity comprising a microbe-binding molecules), but produces a color change when released from the engineered molecules in the presence of a microbe enzyme. Thus, when a microbe binds to the engineered microbe-binding molecules, the microbe releases enzymes that release the detectable label from the engineered molecules. An observation of a color change indicates presence of the microbe in the sample.

In some embodiments, the substrate or the entity attached thereto can be conjugated with a label, such as a detectable label.

In some embodiments, the detectable label is conjugated to a wild-type microbe-binding molecule (e.g. MBL, e.g., human MBL) or a microbe-binding molecule described herein. In some embodiment, the labeling molecule comprises FcMBL. Without washing to be bound by a theory, labeling molecules based on microbe-binding molecules described herein and MBL (e.g., FcMBL) attach selectively to a broad range of microbes, and so they enable the methods described herein to detect the majority of blood-borne microbes with high sensitivity and specificity.

In some embodiments, an enzyme-linked assay (ELISA) can be used to detect signals from a labeling molecule. In ELISA, the labeling molecule can comprise an enzyme as the detectable label. Each labeling molecule can comprise one or more (e.g., 1, 2, 3, 4, 5, 6, 7, 8, 9, 10 or more) enzymes. Additionally, each labeling molecule can comprise one or more (e.g., 1, 2, 3, 4, 5, 6, 7, 8, 9, 10 or more) sites for binding with a microbe.

For ELISA, any labeling molecule conjugated to an enzyme can be used. Exemplary labeling molecules include those comprising a microbe-binding molecule described herein. Other exemplary labeling molecules include those comprising MBL (e.g., human MBL), FcMBL, AKT-FcMBL, wheat germ agglutinin, lectins, antibody molecules (e.g., gram-negative antibody molecules or gram-positive antibody molecules), antigen binding fragments of antibodies, aptamers, ligands (agonists or antagonists) of cell-surface receptors and the like. In some embodiments, the labeling molecule comprises MBL or FcMBL labeled with a detectable label, e.g., an enzyme, e.g., horseradish peroxidase.

Similarly, a variety of enzymes can be used, with either colorimetric or fluorogenic substrates. In some embodiments, the reporter-enzyme produces a calorimetric change which can be measured as light absorption at a particular wavelength. Exemplary enzymes include, but are not limited to, beta-galactosidases, peroxidases, catalases, alkaline phosphatases, and the like. In some embodiments, the enzyme is a horseradish peroxidase (HRP) or an alkaline peroxidase (AP).

A microbe-binding molecule and the enzyme can be linked to each other by a linker. In some embodiments, the linker between the microbe-binding molecule and the enzyme is an amide bond. In some embodiments, the linker between the microbe-binding molecule and the enzyme is a disulfide (S-S) bond. In some embodiments when the microbe-binding molecule is a peptide, polypeptide or a protein, the enzyme can be linked at the N-terminus, the C-terminus, or at an internal position of the microbe-binding molecule. Similarly, the enzyme can be linked by its N-terminus, C-terminus, or an internal position.

In one embodiment, the ELISA probe molecule can comprise a MBL or a portion there of or a FcMBL molecule linked to a HRP. Conjugation of HRP to any proteins and antibody molecules are known in the art. In one embodiment, FcMBL-HRP construct is generated by direct coupling HRP to FcMBL using any commercially-available HRP conjugation kit. In some embodiments, the microbes isolated from or remained bound on the substrate comprising an entity can be incubated with the RP-labeled microbe-binding molecules, e.g., MBL or a portion thereof, or a FcMBL molecule linked to a HRP for a period of time, e.g., at least about 5 mins, at least about 10 mins, at least about 15 mins, at least about 20 mins, at least about 25 mins, at least about 30 mins. The typical concentrations of HRP-labeled molecules used in the ELISA assay can range from about 1: 500 to about 1:20,000 dilutions, in one embodiment, the concentration of HRP-labeled microbe-binding molecules, e.g., MBL or a portion thereof, or a FcMBL molecule linked to a HRP molecule, can be about 1: 1000 to about 1: 10000 dilutions.

Further amplification of the ELISA signal can be obtained by multimerizing the recognition molecule (e.g., the microbe-binding molecule) or by multimerizing the detection enzyme (HRP, etc.). For instance, phage expression can be used to yield multimerized MBL and provide a scaffold to increase the concentration of HRP (either through direct coupling of HRP to the phage particles or using an HRP-antiMI3 conjugated antibody molecule).

In some embodiments, the processes or assays described herein can detect the presence or absence of a microbe or microbial matter and/or identify a microbe or microbial matter in a test sample in less than 24 hours, less than 12 hours, less than 10 hours, less than 8 hours, less than 6 hours, less than 4 hours, less than 3 hours, less than 2 hours, less than 1 hour, or lower. In some embodiments, the processes or assays described herein can detect the presence or absence of a microbe or microbial matter and/or identify a microbe or microbial matter in a test sample in less than 6 hours, less than 4 hours, less than 3 hours, less than 2. hours, less than 1 hour, or lower.

In accordance with various embodiments described herein, a test sample or sample, including any fluid or specimen (processed or unprocessed), that is suspected of comprising a microbe and/or microbial matter can be subjected to an assay or method, kit and system described herein. The test sample or fluid can be liquid, supercritical fluid, solutions, suspensions, gases, gels, slurries, and combinations thereof. The test sample or fluid can be aqueous or non-aqueous.

In some embodiments, the test sample can include a biological fluid obtained from a subject. Non-limiting examples of biological fluids that can be contacted with the devices and compositions herein include water, blood (including whole blood, plasma, cord blood and serum), lactation products (e.g., milk), sweat, feces, urine, saliva, tears, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, mucus, peritoneal fluid, pleural fluid, sebum, vomit, bronchial aspirate, synovial fluid, tracheal aspirate, synthetic fluid (e.g., synthetic blood, hormones, nutrients), fractions thereof, and combinations thereof. In some embodiments, a biological fluid can include a homogenate of a tissue specimen (e.g., biopsy) from a subject.

In some embodiments, the biological fluid sample obtained from a subject, e.g., a mammalian subject such as a human subject or a domestic pet such as a cat or dog, can contain cells from the subject. In other embodiments, the biological fluid sample can contain non-cellular biological material, such as non-cellular fractions of blood, saliva, or urine.

The biological fluid sample can be freshly collected from a subject or a previously collected sample. In some embodiments, the biological fluid sample used in the assays and/or methods described herein can be collected from a subject no more than 24 hours, no more than 12 hours, no more than 6 hours, no more than 3 hours, no more than 2 hours, no more than 1 hour, no more than 30 minutes or shorter.

In some embodiments, the biological fluid sample or any fluid sample described herein can be treated with a chemical and/or biological reagent prior to use with the assays and/or methods described herein. In some embodiments, at least one of the chemical and/or biological reagents can be present in the sample container before a fluid sample is added to the sample container. For example, blood can be collected into a blood collection tube such as VACUTAINER®, which comprises heparin. Examples of the chemical and/or biological reagents can include, without limitations, surfactants and detergents, salts, chelating agents, cell lysing reagents, anticoagulants, degradative enzymes (e.g., proteases, lipases, nucleases, collagenases, cellulases, amylases), and solvents such as buffer solutions. Reagents include, but are not limited to, saline solutions, PBS solutions, buffered solutions, such as phosphate buffers, EDTA, Tris solutions, and any combinations thereof.

In some embodiments, the test sample can include a fluid or specimen obtained from an environmental source, e.g., but not limited to, water supplies (including wastewater), ponds, rivers, reservoirs, swimming pools, soils, food processing and/or packaging plants, agricultural places, hydrocultures (including hydroponic food farms), pharmaceutical manufacturing plants, animal colony facilities, and any combinations thereof.

In some embodiments, the test sample can include a fluid (e.g., culture medium) from a biological culture. Examples of a fluid (e.g., culture medium) obtained from a biological culture includes the one obtained from culturing or fermentation, for example, of single- or multi-cell organisms, including prokaryotes (e.g., bacteria) and eukaryotes (e.g., animal cells, plant cells, yeasts, fungi), and including fractions thereof. In some embodiments, the test sample can include a fluid from a blood culture. In some embodiments, the culture medium can be obtained from any source, e.g., without limitations, research laboratories, pharmaceutical manufacturing plants, hydrocultures (e.g., hydroponic food farms), diagnostic testing facilities, clinical settings, and any combinations thereof.

In some embodiments, the test sample can include a media or reagent solution used in a laboratory or clinical setting, such as for biomedical and molecular biology applications. The media can be a medium for maintaining a tissue, an organism, or a cell population, or a medium for culturing a tissue, an organism, or a cell population, which contains nutrients that maintain viability of the tissue, organism, or cell population, and support proliferation and growth.

In some embodiments, the test sample can be a non-biological fluid. Exemplary non-biological fluids include, but are not limited to, water, salt water, brine, ionic liquids, buffered solutions, saline solutions, sugar solutions, carbohydrate solutions, lipid solutions, suspensions, colloids, nucleic acid solutions, hydrocarbons (e.g. liquid hydrocarbons), acids, gasoline, petroleum, liquefied samples (e.g., liquefied samples), and mixtures thereof.

In some embodiments, the substrate having an entity attached thereto binds one or more of a bacterium, fungus, virus, virus-like particle, particles in solution, or particles in suspension as described herein, e.g., as described in the previous section.

In some embodiments, an assay described herein, e.g., ELISA, comprises a blocking agent. The blocking agent can be, e.g., a blocking agent described in International Application WO2014144325, which is herein incorporated by reference in its entirety. Examples of a saccharide-based blocking agent include, without limitations, hexose (e.g., glucose), maltose, mannose, N-acetyl-muramic acid, amino sugars (e.g., galactosamine, glucosamine, sialic acid, N-acetylglucosamine), sulfosugars (e.g., sulfoquinovose), trehalose, cellobiose, lactose, lactulose, sucrose, fructo-oligosaccharides, cellulose, chitin, or any combinations thereof.

Additional Uses

In some embodiments, the products and kits herein can be used to detect microbes and/or associated microbial matter present in a biofilm or to treat equipment surfaces to prevent or inhibit formation of a biofilm. For example, *Listeria monocytogenes* can form biofilms on a variety of materials used in food processing equipment and other food and non-food contact surfaces (Blackmail, J Food Prot 1996; 59:827-31; Frank, J Food Prot 1990; 53:550-4; Krysinski, J Food Prot 1992; 55:246-51; Ronner, J Food Prot 1993; 56:750-8). Typically, in biofilms, microbial cells are attached to a surface, and are embedded in a matrix of extracellular polymeric substances produced by the microorganisms. Biofilms occur in many environments and frequently lead to a wide diversity of undesirable effects. For example, biofilms cause fouling of industrial equipment such as heat exchangers, pipelines, and ship hulls, resulting in reduced heat transfer, energy loss, increased fluid frictional resistance, and accelerated corrosion. Biofilm accumulation on teeth and gums, urinary and intestinal tracts, and implanted medical devices such as catheters and prostheses frequently lead to infections (Characklis W G. Biofilm processes. In: Characklis W G and Marshall K C eds. New York: John Wiley & Sons, 1990: 195-231; Costerton et at, Annu Rev Microbiol 1995; 49:711-45).

In still further embodiments, the products and kits described herein can be used to target plant microbes and/or associated microbial matter. Plant fungi have caused major epidemics with huge societal impacts. Examples of plant fungi include, but are not limited to, *Phytophthora infestans*, Crinipellis perniciosa, frosty pod (Moniliophthora roreri), oomycete *Phytophthora capsici, Mycosphaerella fijiensis, Fusarium Ganoderma* spp fungi and *Phytophthora*. An exemplary plant bacterium includes *Burkholderia cepacia*. Exemplary plant viruses include, but are not limited to, soybean mosaic virus, bean pod mottle virus, tobacco ring spot virus, barley yellow dwarf virus, wheat spindle streak vims, soil born mosaic virus, wheat streak virus in maize, maize dwarf mosaic virus, maize chlorotic dwarf virus, cucumber mosaic virus, tobacco mosaic virus, alfalfa mosaic virus, potato virus X, potato virus Y, potato leaf roll virus and tomato golden mosaic virus.

In yet other embodiments, the products and kits described herein can be used to detect or combat bioterror agents (e.g., B. *Anthracis* and smallpox).

Quality Control

In some embodiments, a device produced by a method herein is tested before being released or sold. For instance, a cell toxicity assay such as ISO 10993-1 can be performed. In some embodiments, a biocompatibility test is performed. In some embodiments, the test indicates that the contaminant is present at less than about 1000, 900, 800, 700, 600, 500, 400, 300, 200, 100, 50, or 10 nM.

In one respect, the present invention relates to the herein described compositions, methods, and respective component (s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of")

The present invention may be as defined in any one of the following numbered paragraphs.

1. A method of making a substrate having an entity (e.g., a polypeptide, e.g., a glycopolypeptide, e.g., a glycoprotein, a nucleic acid, a carbohydrate, e.g., a polysaccharide, a biological polymer, a small molecule, a peptidomimetic, a drug, or a moiety that can interact with, e.g., specifically bind, a pathogenic or disease molecule, e.g., bind a glycopolypeptide, e.g., a glycoprotein) attached thereto, the method comprising:

I:
   i) contacting the substrate with a plasma to form a modified substrate comprising a plasma-generated-moiety (PGM); and
   ii) contacting the entity (e.g., a biological polymer, e.g., a polypeptide) with the modified substrate under conditions sufficient for attachment of the entity to the modified substrate;

II:
   i) obtaining a modified substrate comprising a PGM; and
   ii) contacting the entity (e.g., a biological polymer, e.g., a polypeptide) with the modified substrate under conditions sufficient for attachment of the entity to the modified substrate; or III:
   i) contacting the substrate with a plasma to form a modified substrate comprising a PGM; and
   ii.a) classifying the modified substrate comprising a PGM as suitable for contacting the entity (e.g., a biological polymer, e.g., a polypeptide) with the modified substrate under conditions sufficient for attachment of the entity to the modified substrate; or
   ii.b) transporting, selling, shipping, transferring control of, or transferring possession of, the modified substrate comprising a PGM to a party for contacting the entity (e.g., a biological polymer, e.g., a polypeptide) with the modified substrate under conditions sufficient for attachment of the entity to the modified substrate;

thereby making a substrate having the entity attached thereto, provided that one or more (e.g., 2, 3, 4, 5, 6, 7, 8, 9, 10, or all) of the following:
   a) the substrate is fluid-permeable, ion-permeable, porous, flexible, autoclavable (e.g., retains structure at above 100C), or other than polystyrene;

b) the substrate comprises less than 90, 80, 70, 60 or 50% polystyrene;
c) the substrate comprises polysulfone (PS), polyarylethersulfone (PAES) or polyethersulfone (PES);
d) the substrate comprises a structure having a compartment, e.g., a lumen, e.g., the structure comprises a hollow fiber;
e) the entity comprises a first member of a specific binding pair;
f) the entity comprises an antibody domain, e.g., an Fc domain;
g) the entity comprises a fusion protein;
h) the entity comprises an opsonin;
i) the entity comprises a lectin;
j) the entity comprises a subunit of a multimeric protein; or
k) an attached entity is cross linked to a second entity (e.g., wherein the second entity is attached to the substrate or wherein the second entity is not attached to the substrate); and provided that one or more (e.g., 2 or all) of the following:
l) the plasma is other than an oxygen plasma (e.g., the plasma is a $CO_2$ plasma);
m) the modified substrate is not contacted with or derivatized with a crosslinking moiety (e.g., a silane, e.g., (3-Aminopropyl) trimethoxysilane (APTMS)), prior to attachment of the entity; or
n) the modified substrate is not contacted with an organic solvent (e.g., an organic alcohol, e.g., ethanol) prior to attachment of the entity.

2. The method of paragraph 1, which comprises:
I:
i) contacting the substrate with a plasma to form a modified substrate comprising a plasma-generated-moiety; and
ii) contacting the entity (e.g., a biological polymer, e.g., a polypeptide) with the modified substrate under conditions sufficient for attachment of the entity to the modified substrate.

3. The method of paragraph 1, which comprises:
II:
i) obtaining a modified substrate comprising a PGM; and
ii) contacting the entity (e.g., a biological polymer, e.g., a polypeptide) with the modified substrate under conditions sufficient for attachment of the entity to the modified substrate.

4. The method of paragraph 1, which comprises:
III:
i) contacting the substrate with a plasma to form a modified substrate comprising a PGM; and
ii.a) classifying, the modified substrate comprising a PGM as suitable for contacting the entity, e.g., a biological polymer, e.g., a polypeptide, with the modified substrate under conditions sufficient for attachment of the entity to the modified substrate; or
ii.b) transporting, selling, shipping, transferring control of, or transferring possession of, the modified substrate comprising a PGM to a party for contacting the entity (e.g., a biological polymer, e.g., a polypeptide) with the modified substrate under conditions sufficient for attachment of the entity to the modified substrate.

5. The method of paragraph 1, wherein:
a) the entity is attached directly to a PGM, e.g., without atoms from an activating moiety disposed between the PGM and the entity;
b) after contacting the substrate with the plasma, the entity is attached directly to a PGM;
c) the reaction or reactions for attaching the PGM with the entity are aqueous;
d) the entity is contacted with the modified substrate under aqueous conditions;
e) PGMs, e.g., carboxylic acids, are formed at an abundance of at least about 1%, 2%, 3%, 4%, 5%, 6%, 7%, 8%, 9%, 10%, 15%, or 20% by carbon composition, e.g., as measured by XPS;
f) entities are attached at a density of at least about $1 \times 10^{12}$, $1 \times 10^{13}$, $1 \times 10^{14}$, $1 \times 10^{15}$, $1 \times 10^{16}$, or $1 \times 10^{17}$ molecules per $cm^2$, e.g., as measured by a binding method; or
g) the entity is contacted with the modified substrate at a pH between 6 and 8 (e.g., pH 7 or physiological conditions); or
h) entities are attached at a density of at least about 500, 600, 700, 800, 900, 1000, or 1100 entities/$m^2$.

6. The method of any of the preceding paragraphs, wherein the substrate comprises a lumen, e.g., the substrate comprises a hollow fiber.

7. The method of any of the preceding paragraphs, wherein the substrate comprises cellulose, substituted cellulose e.g., cellulose acetate, cellulose diacetate, or cellulose triacetate; polysulfone, polyethersulfone, polyarylethersulfone, polyvinylpyrrolidone, nylon, polyacrylonitrile (PAN), polycarbonate, polyamide, or polymethylmethacrylate (PMMA).

8. The method of any of the preceding paragraphs, wherein the substrate comprises polydimethylsiloxane (PDMS) or polystyrene.

9. The method of any of the preceding paragraphs, wherein the substrate comprises an adhesive or a sealant, and wherein the adhesive or sealant is not contacted with an organic solvent, e.g., an organic alcohol, e.g., ethanol.

10. The method of any of the preceding paragraphs, wherein the substrate comprises a dialysis, ultrafiltration, hemofiltration, hemodiafiltration, or hemoperfusion cartridge.

11. The method of any of the preceding paragraphs, wherein the substrate comprises a polymer, glass, metal, or ceramic, or any combination thereof.

12. The method of any of the preceding paragraphs, wherein the substrate comprises a hollow-fiber or non-hollow fiber membrane.

13. The method of any of the preceding paragraphs, wherein in step (ii), the modified substrate is substantially free of a crosslinking moiety, e.g., silane, e.g., (3-Aminopropyl) trimethoxysilane (APTMS).

14. The method of any of the preceding paragraphs, wherein in step (ii), the modified substrate is substantially free of organic solvent, or wherein the method does not comprise a step of contacting the modified substrate with an organic solvent, e.g., after step (i) or before step (ii).

15. The method of any of the preceding paragraphs, comprising contacting the modified substrate, the entity, or both, with an activating moiety, e.g., a water-soluble activating moiety, e.g., 1-Ethyl-3-(3-dimethylaminopropyl)carbodiimide (EDC), to activate a functional group on the modified substrate, wherein the functional group is optionally a carboxylic acid group.

16. The method of any of the preceding paragraphs wherein step ii) contacting is performed in aqueous buffer.

17. The method of any of the preceding paragraphs wherein step ii) contacting is performed in a solution comprising 2-morpholino-ethane sulfonic acid (MES) buffer.
18. The method of any of the preceding paragraphs, wherein step ii) contacting is performed at a pH of about 4-5, 4.5-5.5, 5-6, 6-7, 7-8, or about 5.
19. The method of any of the preceding paragraphs, wherein step ii) contacting is performed for about 4-6, 6-8, 8-10, 10-12, 12-14, or 14-16 hours.
20. The method of any of the preceding paragraphs, wherein the activating moiety comprises an atom that is not included in the substrate having the entity attached thereto, e.g., none of the atoms of the activating moiety are included in the substrate having the entity attached thereto.
21. The method of any of the preceding paragraphs, wherein the PGM comprises a carboxylic acid and the entity comprises an amine.
22. The method of any of the preceding paragraphs, wherein a carboxylic acid of the PGM covalently binds with an amine group of the entity.
23. The method of any of the preceding paragraphs, wherein the plasma is a $CO_2$ plasma.
24. The method of any of the preceding paragraphs, wherein the plasma is an $O_2$, $N_2$, or $NH_4$ plasma.
25. The method of any of the preceding paragraphs, wherein contacting the substrate with the plasma is under conditions suitable for forming a predetermined level or density of PGMs on the substrate.
26. The method of any of the preceding paragraphs, wherein the PGM comprises a hydroxyl, aldehyde, epoxide, peroxide, sulfhydryl, carbonyl, or carboxylic acid group.
27. The method of any of the preceding paragraphs, wherein the PGM comprises a carboxylic acid group.
28. The method of any of the preceding paragraphs, wherein at least 1, 2, 3, 4, 5, 6, 7, 8, 9, 10, 20, 30, 40, or 50% of the PGMs comprise a carboxylic acid group.
29. The method of any of the preceding paragraphs, wherein the PGM comprises an aldehyde group.
30. The method of any of the preceding paragraphs, wherein at least 1, 2, 3, 4, 5, 6, 7, 8, 9, 10, 20, 30, 40, or 50% of the PGMs comprise an aldehyde group.
31. The method of any of the preceding paragraphs, wherein the PGM comprises a moiety that is reactive with a moiety on the entity, e.g., an entity that has been contacted with an activating moiety.
32. The method of any of the preceding paragraphs, wherein the plasma is generated by a plasma generator under one or more (e.g., 2, 3, 4, or all) of the following conditions:
a) a radio frequency of about 13-14 MHz, e.g., 13.5 MHz);
b) plasma treatment lasts a sufficient amount of time to link the entity to the modified substrate while maintaining an activity, e.g., a binding activity, of the entity, e.g., the plasma treatment lasts about 0.1-5 min, e.g., about 1 min;
c) the plasma gas pressure is about 150-350 mTorr, e.g., about 200 mTorr;
d) a power of about 10-150 W, e.g., about 100 W; or
e) the plasma generator comprises electrodes outside the plasma generator chamber, e.g., does not comprise electrodes inside the plasma generator chamber.
33. The method of any of the preceding paragraphs, wherein step i) contacting comprises contacting a plurality of substrates (e.g., at least 2, 3, 4, 5, 10, 20, 50, or 100 substrates) with a plasma in a plasma generator chamber.
34. The method of any of the preceding paragraphs, wherein the entity comprises an opsonin, a carbohydrate-binding protein, a calcium-binding protein, a divalent cation binding protein, and/or a portion of an antibody, e.g., an Fc or portion thereof.
35. The method of any of the preceding paragraphs, wherein the entity comprises a polypeptide of SEQ ID NO: 4 or at least 80%, 85%, 90%, 95%, 96%, 97%, 98%, or 99% identical to SEQ ID NO: 4, or a polypeptide of SEQ ID NO: 6 or at least 80%, 85%, 90%, 95%, 96%, 97%, 98%, or 99% identical to SEQ ID NO: 6.
36. The method of any of the preceding paragraphs, wherein the entity forms a multimer, e.g., a dimer, trimer, tetramer, pentamer, hexamer, 12-mer, or 18-mer.
37. The method of paragraph 36, wherein the entity forms a multimer having at least two subunits crosslinked to each other.
38. The method of any of the preceding paragraphs, further comprising acquiring a value for a parameter related to the type of PGM, the number of PGMs, the density of PGMs, the presence of contaminants, the number of attached entities, a contact angle measurement (e.g., a water contact angle measurement), or a surface energy measurement; and comparing the acquired value with a standard.
39. The method of paragraph 38, further comprising, responsive to the comparison, classifying, accepting, rejecting, approving, incorporating into a product, packaging, transferring to a new location, or releasing into commerce, the substrate comprising the attached entity.
40. The method of any of the preceding paragraphs, further comprising, evaluating the modified substrate, e.g., with X-ray photon spectroscopy (XPS), for the presence of a PGM.
41. The method of any of the preceding paragraphs, further comprising, evaluating the modified substrate for contaminants or manufacturing reagents, e.g., an extractable molecule, a leachable molecule, FcMBL not linked to the substrate, EDC, solvent (e.g., MES buffer), endotoxin, pyrogen, nuclease, or an organism e.g., a bacterium or fungus.
42. The method of any of the preceding paragraphs, further comprising: cleansing the plasma generator chamber before step i), e.g., by performing one or more of (e.g., 2 or all of):
a) washing the chamber with a solvent (e.g., an organic solvent, e.g., ethanol),
b) producing a cleansing plasma in the chamber (e.g., a cleansing plasma made of a different gas from the plasma of step i), e.g., cleansing using an 02 plasma when the plasma of step i) is a $CO_2$ plasma); and/or
c) cleaning the chamber by chemical cleaning.
43. The method of paragraph 42, wherein the cleansing plasma is produced for about 30 minutes, at a temperature of about 400 C, or both.
44. The method of any of the preceding paragraphs, comprising determining the cleanliness of the plasma generator chamber by performing one or more (e.g., 2 or all) of the following:
a) during the cleansing step, monitoring the color of the plasma, e.g., wherein an $O_2$ plasma is blue when organic matter is present and white when organic matter is absent, or a $CO_2$ plasma is dark blue when organic matter is present and light blue when organic matter is absent; or b) during the contacting of step i), monitoring the temperature of the plasma, wherein the temperature of the plasma does not rise above 80 C in the first minute that the plasma is produced, wherein temperature rising above 80 C in the first minute indicates presence of a contaminant; or c) during the cleansing step, monitoring the temperature of the plasma, wherein the temperature of the plasma drops below 10 C of peak temperature (typically between 400-500 C), wherein temperature continuing to rise or maintaining the peak temperature indicates presence of a contaminant.

45. The method of any of the preceding paragraphs, comprising, when the substrate is disposed in the plasma generator chamber, e.g., before the contacting of step i), performing one or both of a) creating a vacuum in the plasma generator chamber (e.g., a pressure of less than 1 Torr) and b) filling the plasma generator chamber with a gas, e.g., the same gas used to make the plasma of step i), e.g., $CO_2$.

46. The method of paragraph 45, wherein the plasma generator chamber is filled with the gas, e.g., $CO_2$, for, e.g., at least about 1, 2, 3, 4, 5, 6, 7, 8, 9, or 10 minutes, e.g., about 5 minutes.

47. The method of any of the preceding paragraphs, comprising measuring modification of the substrate, e.g., by performing one or more of:

a) contacting the substrate with a drop of a liquid, e.g., water, and measuring the contact angle of the drop of liquid;

b) contacting the substrate with a moiety that binds the entity, e.g., wherein the moiety comprises an antibody molecule or a saccharide such as mannose, wherein the moiety is optionally bound or covalently linked to a detectable label; or c) contacting the substrate with a moiety that binds a PGM, e.g., a detectable label comprising an amine group.

48. The method of any of the preceding paragraphs comprising providing a masking entity during attachment of the entity to the substrate, wherein the masking entity inhibits reaction of a portion of the entity with, e.g., the activating moiety, the substrate, or another entity e.g., a biological polymer such as a polypeptide.

49. The method of paragraph 48, wherein the masking entity comprises a moiety to which the entity binds.

50. The method of paragraph 48, wherein the entity comprises an opsonin, e.g., MBL, and the masking entity comprises a moiety to which the opsonin binds, e.g., a divalent cation, e.g., $Ca^{2+}$, or a sugar, e.g., glucose.

51. The method of any of the preceding paragraphs, wherein the density of attached entities, e.g., as measured by a binding assay, in a first selected area, e.g., a one $cm^2$ area, is within 50% of the density of 1, 2, 3, 4, 5, or 10 other selected areas, e.g., areas of one $cm^2$ each on the substrate.

52. The method of any of the preceding paragraphs, wherein the density of 10, 20, 30, 40, 50, 60, or 70% of the one $cm^2$ areas on the substrate, or a portion of the substrate, e.g., the lumen of a hollow fiber, are within 50, 40, or 30% of one another or of a base of a well, bases of a plurality of wells, or a hollow fiber.

53. A device comprising a substrate having an entity attached thereto, produced by the method of any of paragraphs 1-52.

54. A device comprising a substrate having an entity attached thereto, producible by the method of any of paragraphs 1-52.

55. A device comprising a substrate, e.g., a permeable membrane, having an entity, e.g., a polypeptide, e.g., a polypeptide comprising a portion of an MBL, attached thereto, wherein the device comprises less than $1\times10^{16}$, $1\times10^{15}$, $1\times10^{14}$, $1\times10^{13}$, $1\times10^{12}$, $1\times10^{11}$, $1\times10^{10}$, $1\times10^9$, $1\times10^8$, $1\times10^7$, $1\times10^6$, $1\times10^5$, $1\times10^4$, $1\times10^3$, 100, 10, or 1 molecule per $cm^2$ of a crosslinking agent, e.g., silane, e.g., as measured by a binding assay.

56. A device comprising a substrate, e.g., a permeable membrane, having a plurality of entities, e.g., polypeptides, e.g., a polypeptide comprising a portion of an MBL, attached thereto, wherein the density of attached entities, e.g., as measured by a binding assay, in a first selected area, e.g., a one $cm^2$ area, is within 50% of the density of 1, 2, 3, 4, 5, or 10 other selected areas, e.g., one $cm^2$ areas on the substrate, or wherein the density of 10, 20, 30, 40, 50, 60, or 70% of the one $cm^2$ areas on the substrate, or a portion of the substrate, e.g., the lumen of a hollow fiber, are within 50, 40, or 30% of one another or of a base of a well, bases of a plurality of wells, or a hollow fiber.

57. A device comprising a substrate, e.g., a permeable membrane, having an entity, e.g., a polypeptide, e.g., a polypeptide comprising a portion of an MBL, attached thereto, wherein an amino group of the entity (e.g., an amino group of a lysine side chain or an N-terminus) is directly covalently bound to a PGM (e.g., a carboxylic acid) on the substrate.

58. A device comprising a substrate, e.g., a permeable membrane, having an entity, e.g., a polypeptide, e.g., a polypeptide comprising a portion of an MBL, attached thereto, wherein the device comprises less than $1\times10^{16}$, $1\times10^{15}$, $1\times10^{14}$, $1\times10^{13}$, $1\times10^{12}$, $1\times10^{11}$, $1\times10^{10}$, $1\times10^9$, $1\times10^8$, $1\times10^7$, $1\times10^6$, $1\times10^5$, $1\times10^4$, $1\times10^3$, 100, 10, or 1 molecules per $cm^2$ or less than $1\times10^{16}$, $1\times10^{15}$, $1\times10^{14}$, $1\times10^{13}$, $1\times10^{12}$, $1\times10^{11}$, $1\times10^{10}$, $1\times10^9$, $1\times10^8$, $1\times10^7$, $1\times10^6$, $1\times10^5$, $1\times10^4$, $1\times10^3$, 100, 10, or 1 molecules per device of a contaminant, e.g., an extractable molecule, a leachable molecule, FcMBL not linked to the substrate, EDC, solvent (e.g., MES buffer), endotoxin, pyrogen, nuclease, or an organism e.g., a bacterium or fungus.

59. A reaction mixture comprising:

a substrate, e.g., a permeable membrane, which comprises less than $1\times10^{16}$, $1\times10^{15}$, $1\times10^{14}$, $1\times10^{13}$, $1\times10^{12}$, $1\times10^{11}$, $1\times10^{10}$, $1\times10^9$, $1\times10^8$, $1\times10^7$, $1\times10^6$, $1\times10^5$, $1\times10^4$, $1\times10^3$, 100, 10, or 1 molecule per $cm^2$ of a crosslinking agent, e.g., a silane;

an entity, e.g., a polypeptide, e.g., a polypeptide comprising a portion of an MBL; and an aqueous solution comprising an activating moiety, e.g., a water-soluble activating moiety, e.g., EDC.

60. A reaction mixture comprising:

a substrate, e.g., a permeable membrane, an entity, e.g., a polypeptide, e.g., a polypeptide comprising a portion of an opsonin e.g., a portion of MBL; and a masking entity, e.g., a moiety to which the opsonin binds or a divalent cation, e.g., $Ca^{2+}$.

61. The reaction mixture of paragraph 60, wherein the masking entity comprises a sugar, e.g., glucose.

62. A device comprising a substrate, e.g., a permeable membrane, having an entity, e.g., a polypeptide, e.g., a polypeptide comprising a portion of an MBL, attached thereto, wherein entities are attached to the substrate at a density of about 500-2000, 500-1800, 500-1600, 500-1200, 600-2000, 600-1800, 600-1600, 600-1200, 800-2000, 800-1800, 800-1600, 800-1200, 1000-2000, 1000-1800, 1000-1600, or 1000-1200 entities/m².

EXAMPLES

The invention now being generally described, it will be more readily understood by reference to the following examples, which are included merely for purposes of illustration of certain aspects and embodiments of the present invention, and are not intended to limit the invention. As such, it will be readily apparent that any of the disclosed specific constructs and experimental plan can be substituted within the scope of the present disclosure.

Example 1: X-ray Photon Spectroscopy (XPS) Studies of $CO_2$-Treated Polyethersulfone Most plastics do not have enough reactive groups on their surface to adequately functionalize a surface with a biomolecule. XPS was used to characterize the extent of oxidation on the surface of plastics modified with plasma to verify required reactive moieties were present before coupling.

Preparation of PES samples

Polyethersulfone (PES) sheets were acquired from Goodfellow Cambridge Limited. Samples of the sheets were prepared by cutting the material into 8 mm×11 mm rectangles. The samples were washed 3 times in a 70% ethanol/water solution by vortex, followed by three rinses with 70% ethanol/water. The samples were dried in room air prior to plasma treatment. $CO_2$ Plasma treatment of PES PES samples were exposed to $CO_2$ plasma at either varying time or varying power. The 18.56 MHz radio frequency capacitively coupled plasma generator was a Model Nano from Diener. The chamber was first cleaned of contaminants through a cycle with an empty chamber. The chamber was first pulled to a vacuum at 0.14 mbar and then raised to a pressure of 0.26 mbar with pure 02 gas input for 1 min. Plasma was then generated for 30 min at 150 W (50% power). Samples were introduced into the chamber once the unit has cooled (up to four hours). The chamber was then pulled to a vacuum at 0.14 mbar and then raised to a pressure of 0.26 mbar with pure $CO_2$ gas input for 5 min. Plasma treatment times varied from 0 min, 0.5 min, 1 min, 3 min, and 5 min at 100 Watts. The samples were analyzed on the same day by XPS to identify the presence of added carboxylate functionality on PES surface.

XPS of PES

X-ray photoelectron spectroscopy (XPS) analysis of the PES samples was performed on a Thermo Scientific K-Alpha spectrometer. The spectrometer generates a 12V electron beam from an aluminum Kα source. The PES samples were probed at an x-ray energy of 1.4866 keV with a line width of 0.85 eV. An x-ray spot size was 400 m was employed to obtain the derived functional changes over an average area. The chemical composition was analyzed at one spot on each PES sample.

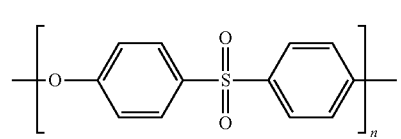

Structure of Polyethersulfone

Component analyses of each spectra was done on the program CasaXPS.

For the C1s spectra the following peaks were quantified:

TABLE 4

| Peak assignments for carbon is | |
|---|---|
| Chemistry | BE(eV) |
| C—C | 285.0 |
| C—O | 286.6 |
| C=O | 287.6 |
| O—C=O | 289.0 |

Figure 2:
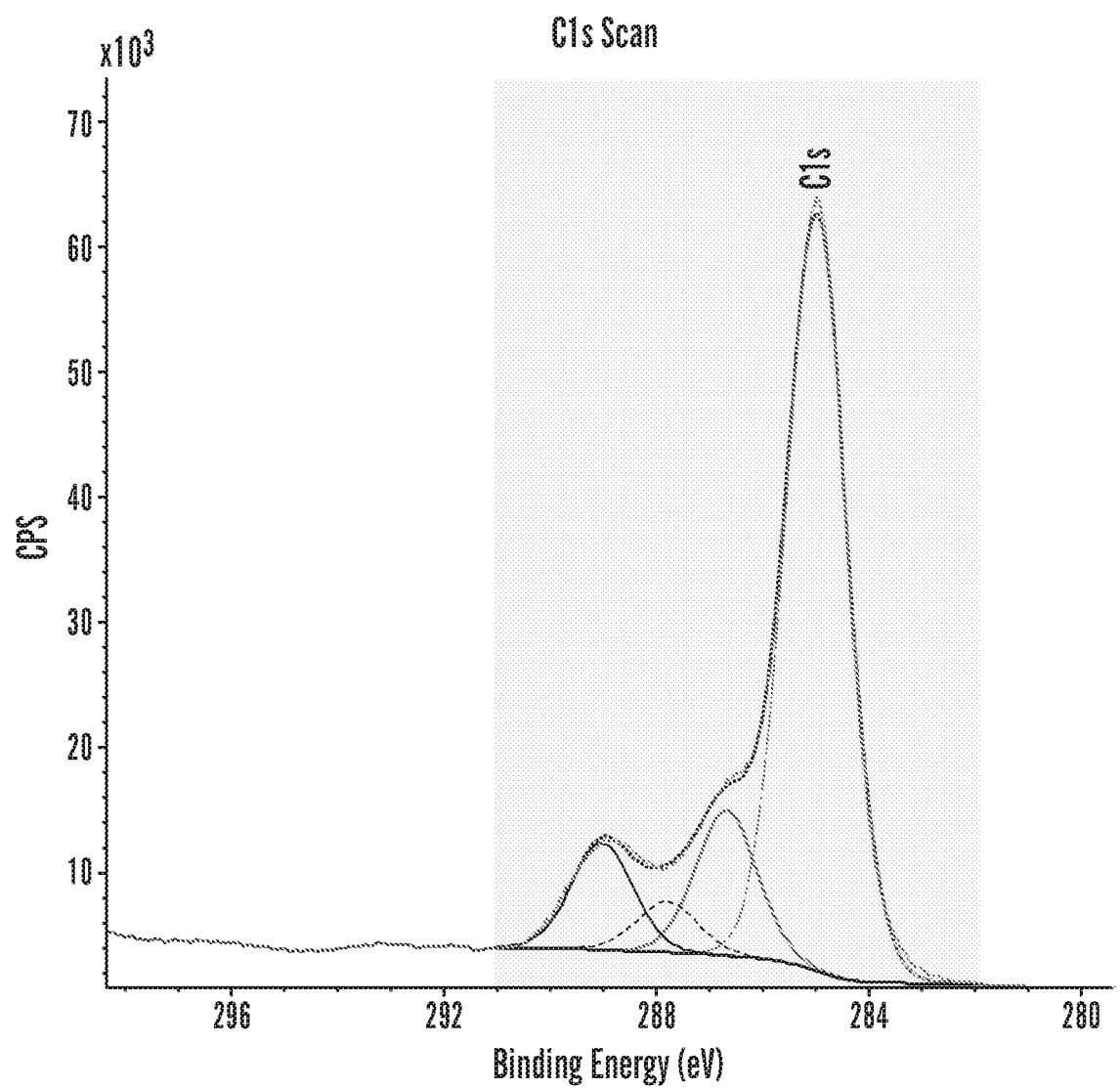
FIG. 2 shows that XPS spectra of PES exposed to $CO_2$ plasma for 5 minutes at 100 W reveal significant percentage of oxidized carbon, especially carboxylate groups.

FIG. 1 shows XPS analysis of native (untreated) PES sample. FIG. 2 shows XPS analysis of a plasma-treated PES sample.

Figure 3:
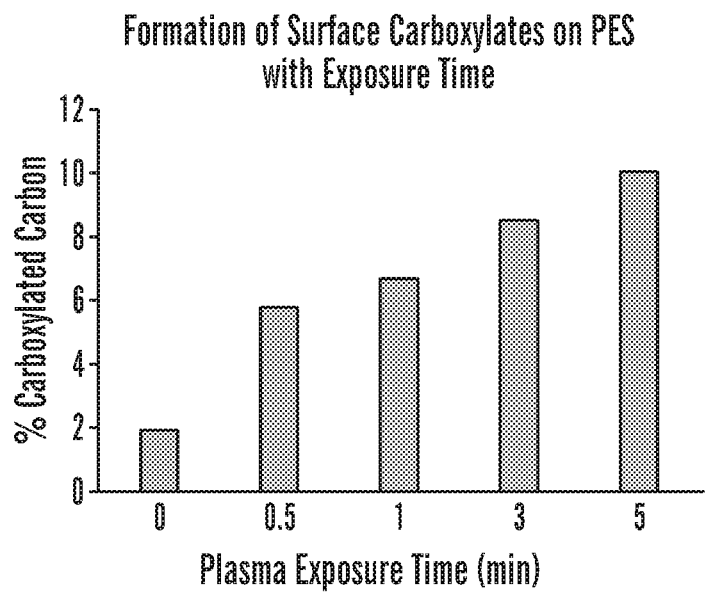
FIG. 3 shows that surface carboxylate composition on PES increases with $CO_2$ plasma exposure time at 100 W power.

Component analysis of the XPS spectra illustrate that increasing treatment times in the $CO_2$ plasma yield increasing percentages of oxidized carbon moieties, in particular carboxylate moieties (see FIG. 3). These carboxylate groups are now available for coupling to amine groups on molecules of interest through crosslinking chemistry (e.g. EDC).

Example 2: Functionalization of $CO_2$-treated PES with amino-quantum dots

Methods

PES samples were functionalized with QDOT 655 ITK Amino(PEG) quantum dots from Life Technologies (Cat #Q21521MP). PES was first treated with $CO_2$ plasma at 100 W for 1 minute with the samples oriented face up in a petri dish. Following plasma treatment, the samples were transferred to a multiwell 24-well plate with the plasma treated side up.

The quantum dots were prepared by combining two fresh vials (250 ul) of the manufacturer's solution into an Eppendorf tube. The solution was gently vortexed to mix the dark red solutions. A dilution of the QDots solution was prepared by dissolving 307 uL of the dots in 14 mL of 1 mM PIPES solution at a pH of 7.0.

The chemistry was applied to the PES samples in four groupings.
1.) (−) EDC conjugate; (−) $CO_2$ plasma
2.) (+) EDC conjugate; (−) $CO_2$ plasma
3.) (−) EDC conjugate; (+) $CO_2$ plasma
4.) (+) EDC conjugate; (+) $CO_2$ plasma An EDC solution was prepared to a concentration of 20 mg/mL in PIPES buffer. To each PES sample in a well 12.8 uL of dilute Qdot stock was added. 587.2 uL of PIPES buffer was added. Either 200 uL of EDC solution or 200 uL of PIPES buffer added to the well. The total volume of the reaction mixture in each well was 0.8 uL. The well plate was shaken on an orbital shaker for one hour at room temperature. Subsequently, the well plate was placed on an orbital shaker at 4C overnight.

After conjugation the Qdots solution was removed from each well. Each well was rinsed with 1 mL of deionized (DI)

water (Millipore-18.2 Mohm water). Each PES sheet sample was transferred to an Eppendorf tube and sonicated in a solution on 0.5% Tween-20 in DI water for five minutes. The Tween solution was aspirated from the Eppendorf tube and the solution was replaced with DI water. The sample tube was vortexed for 10 seconds. The DI water was replaced with Tween solution and the samples were sonicated again for 5 minutes. Finally each sample was rinsed with DI water and vortexed three times. The samples were stored in DI water at 4C, prior to microscopic assessment.

Confocal Imaging

Samples were imaged on a Leica SP5 X MP inverted confocal microscope. The purpose of imaging was to assess the extent of surface functionalization by quantifying the fluorescence, as a function of area. Excitation achieved with a Cohert Chameleon multiphoton laser with the peak centered at 810 nm. The power output of the laser was 3.2 W. The gain on the detectors was fixed at 500. The confocal pinhole was fixed at 55.10 um.

The detectors were configured to collect the autofluorescence of the PES and the red fluorescence of the Qdots on separate channels.

For each of the chemistry conditions, three PES sheets were imaged at 3 points. The scan area was 512×512 pixels or 620×620 microns. The number of planes collected for each sample was visually determined based on the observation of the Qdot treated surface. Sectioning was performed by scanning through the sample to locate an area of autofluorescence in the bulk sample and withdrawing the focus to locate the material surface, followed by a region of free space.

Analysis

ImageJ software was used to quantify the fluorescence intensity of the surface layer, a measure of the amount of quantum dots attached to the surface. A mask was used to exclude the aggregates of dots. The analysis showed the greatest coverage of quantum dots on the $CO_2$ plasma treated and EDC coupled surface, indicating both steps are required for the greatest surface coating.

Scanning Electron Microscopy

The PES films were further characterized with SEM to determine the distribution of the quantum dots at subwavelength (<200 nm) resolution. Imaging revealed the dots were tightly packed on the surface when treated with both $CO_2$ plasma and EDC crosslinking chemistry.

Figure 4:
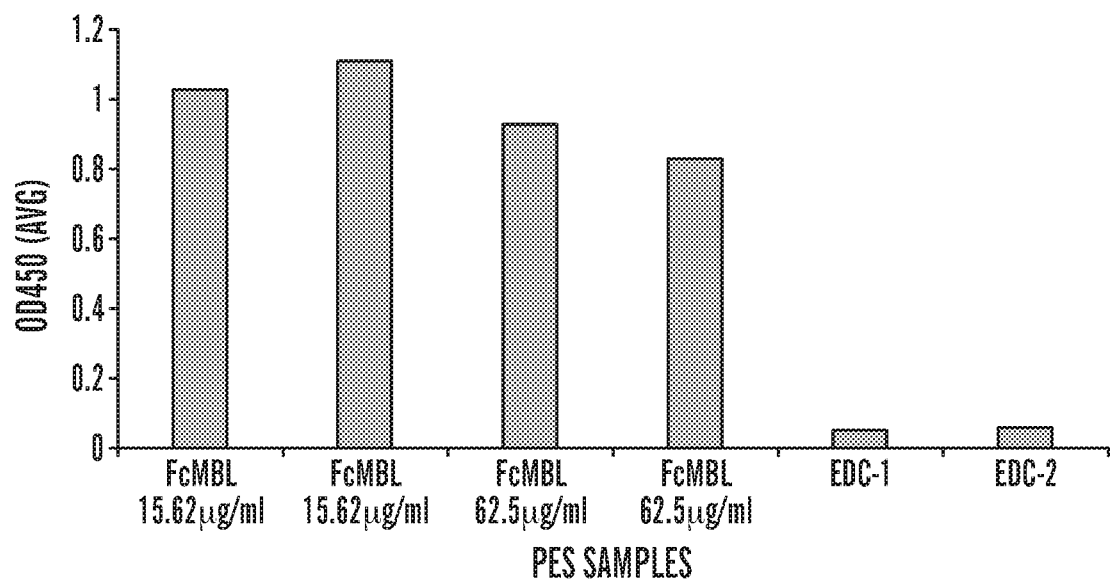
FIG. 4 shows a Mannan Binding assay performed on PES Chips to which FcMBL was coupled via Plasma/EDC treatment.

$CO_2$ plasma followed by coupling to amines provides an even, dense coating of biomolecule onto generic surfaces. This process was used to couple FcMBL to PES. The FcMBL was functional as measured by its ability to bind mannan (FIG. 4). The following methods were used:

Covalent Coupling: PES Chips
1. Place PES chips in 12-well plate. Plasma treat (100W, 1 minute)
2. Dilute FcMBL to 125 ug/ml in 1x PBS
3. Dissolve EDC at 1mg/ml in 1x PBS
4. Mix FcMBL 1:1 with EDC, invert lightly
5. Aliquot FcMBL-EDC onto PES chips, 500ul/well. Incubate overnight at 4C
6. Wash PES chips 3x 1ml/well with 1x PBS Mannan Binding: PES Chips
7. Block PES Chips: 10 mM glucose, 0.1% BSA in TBS-T Ca++, 500ul/well. Incubate shaking for 1 hour at RT
8. Wash PES Chips: 3x 1ml/well, TBS-T Ca++
9. Dilute mannan to 31.25ug/ml in TBS-T Ca++
10. Aliquot mannan onto PES chips, 500ul/well. Incubate shaking for 1 hour at RT
11. Wash PES Chips: 3x 1ml/well, TBS-T Ca++
12. Dilute rhMBL-HRP 1.5ul in 10 ml 3% BSA/TBS-T Ca++
13. Aliquot rhMBL-HRP onto PES chips, 500ul/well. Incubate shaking for 1 hour at RT
14. Wash PES Chips: 3x 1ml/well, TBS-T Ca++
15. Transfer PES chips to new 12-well plate
16. Develop: 500ul/well of TMB. Incubate at RT for 1 minute
17. Quench Reaction: 250ul/well of sulfuric acid
18. Transfer samples over to 96-well plate, 100ul/well in triplicate
19. Read at 450 nm Example 3: Plasma treatment and FcMBL attachment to a dialysis cartridge FcMBL was attached to a dialysis cartridge using the following method.

After chamber cleaning cycle (e.g., as described in Example 1), hollow fiber dialysis cartridge(s) ("dialyzers") were placed in the chamber on the glass shelf, roughly halfway between the back of the chamber and the entrance to the chamber. The chamber was evacuated to a pressure of 0.14 mbar, then exposed to 0.26 mbar pure $CO_2$ for 5 min to ensure the filter was filled with $CO_2$ gas. The chamber generated plasma for 1 min at 100 W maintaining the 0.26 mbar pressure.

The filter was filled with a cold (4C) MES pH5 solution containing 0.5 mg/mL EDC and 250 ug/mL FcMBL. The filter was chilled and stored at 4 C overnight (-16 hr). The filter was flushed with 2 L of PBS solution, then 1 L of PBS with 10 mM EDTA. The filter was stored at 4 C until use.

Example 4: Plasma-treated plates for use in ELISA

Figure 5:
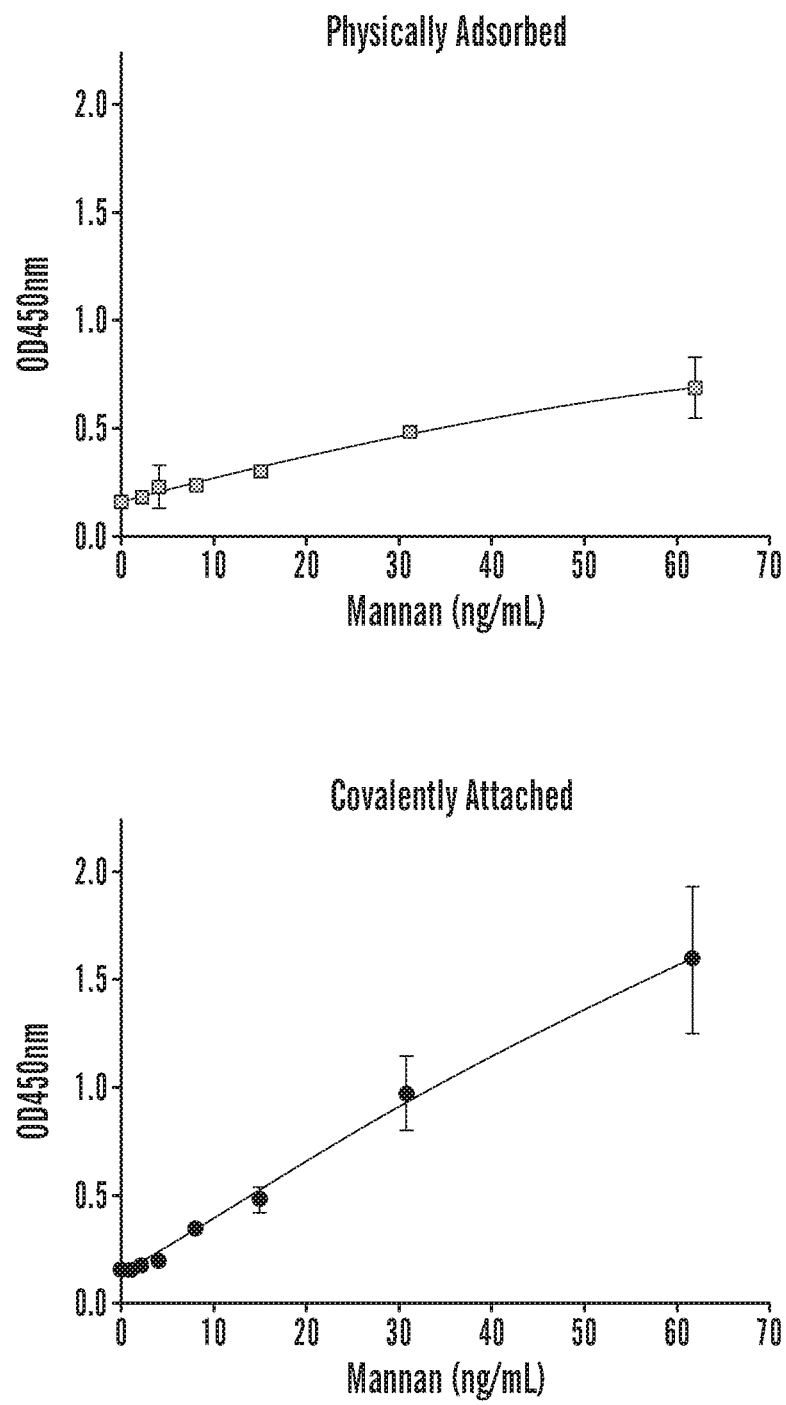
FIG. 5 is a pair of graphs showing the sensitivity of an ELISA assay performed with FcMBL adsorbed to a plate (top panel) or covalently coupled to a plate (bottom panel).

This Example illustrates that the sensitivity of the covalently bound ELISA was significantly greater than the passively adsorbed ELISA for the detection of mannan in whole blood (FIG. 5).

Covalent Coupling of FcMBL to a 96 Well Plate was performed as follows:
1. Plasma treat a 96 well ELISA plate ($CO_2$, 100W, 1 minute)
2. Dilute FcMBL to 31.25 micrograms (ug)/ml in 1x PBS
3. Dissolve EDC to 1mg/ml in 1x PBS
4. Mix FcMBL solution with EDC solution, invert lightly
5. Aliquot FcMBL-EDC 100ul/well onto plasma treated 96 well plate
6. Incubate overnight at 4C
7. Wash plate 4x 200ul/well with 1x PBS
8. Block plate: 10 mM glucose, 0.1% BSA in TBS-T Ca++, 200ul/well. Incubate for 1 hour at RT, shaking at 350RPM
9. Wash plate 4x 200ul/well with TBS-T Ca++
10. Dilute mannan to 62.5 ng/ml in TBS-T Ca++or whole blood and complete 7 two-fold dilutions
11. Aliquot mannan dilutions in triplicate, 100ul/well. Incubate for 30 minutes at RT, shaking at 350RPM
12. Wash plate 4x 200ul/well with TBS-T Ca++
13. Dilute rhMBL-HRP, 1.5ul in 10 ml 3% BSA/TBS-T Ca++
14. Aliquot rhMBL-HRP 100ul/well. Incubate for 30 minutes at RT, shaking at 350RPM
15. Wash plate 4x 200ul/well with TBS-T Ca++

Figure 6:
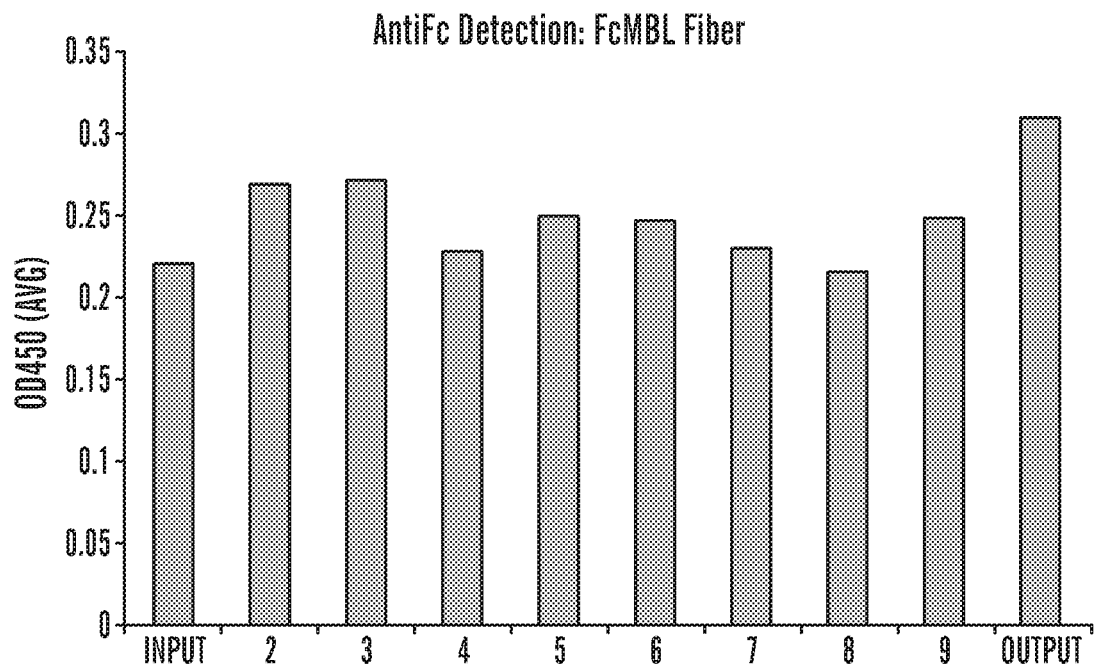
FIG. 6 is a graph showing the presence of FcMBL in sections along a filter to which the FcMBL was coupled.

16. Aliquot TMB 100ul/well. Incubate for ~1 minute at RT
17. Quench reaction: Aliquot sulfuric acid 50ul/well
18. Read plate at 450 nm Example 5: Assaying attachment of FcMBL to a substrate This example describes an Fc assay that was performed inside a hollow fiber:
1. After covalently coupling FcMBL to hollow fiber, flush fibers 3x 10 ml with 1xPBS
2. Cut open hollow fiber casing to reveal internal fibers
3. Using tweezers, remove 1 fiber, cut into 1 inch long pieces and place each piece into 1 well of 12-well plate
4. Block: Aliquot 3% BSA/TBS-T Ca++, 500ul/well. Incubate for 1 hour at room temperature, shaking
5. Wash 3x with TBS-T Ca++, 500ul/well
6. Dilute HRP-conjugated anti-Fc antibody (Jackson) 1:10,000 in 1% BSA/TBS-T Ca++
7. Aliquot anti-Fc antibody solution 500ul/well. Incubate for 1 hour at room temperature, shaking
8. Wash 3x with TBS-T Ca++, 500ul/well
9. Develop: Aliquot TMB 500ul/well. Incubate for ~1 minute
10. Quench Reaction: Aliquot sulfuric acid 250ul/well
11. Pipette 100ul/well in triplicate into 96 well plate
12. Read at 450 nm The ELISA for Fc on the hollow fibers demonstrated the FcMBL was coupled along the length of the filter (FIG. 6). All FcMBL levels were above the background (control) level (data not shown).

Figure 7:
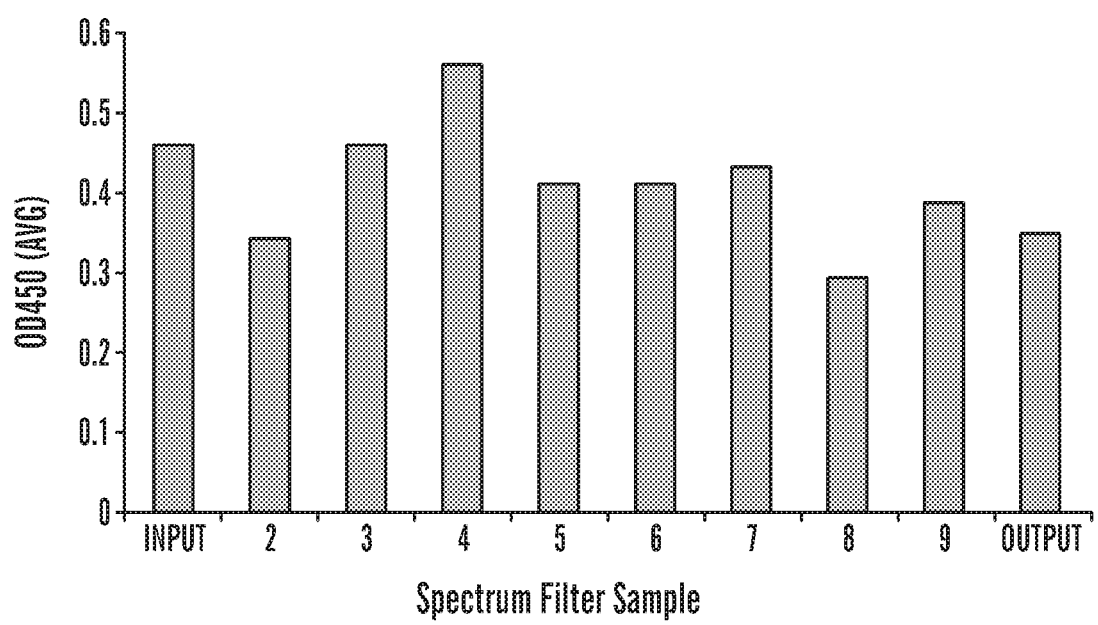
FIG. 7 is a graph showing the presence of HRP in sections along a filter to which the HRP was coupled.

In a similar experiment, HRP was covalently coupled to a 1kd MWCO spectrum filter and was found to be coupled evenly along the length (FIG. 7). A negative control reaction lacking EDC yielded OD450 values well below 0.1 (data not shown).

Example 6: Coupling buffer conditions

Figure 8:
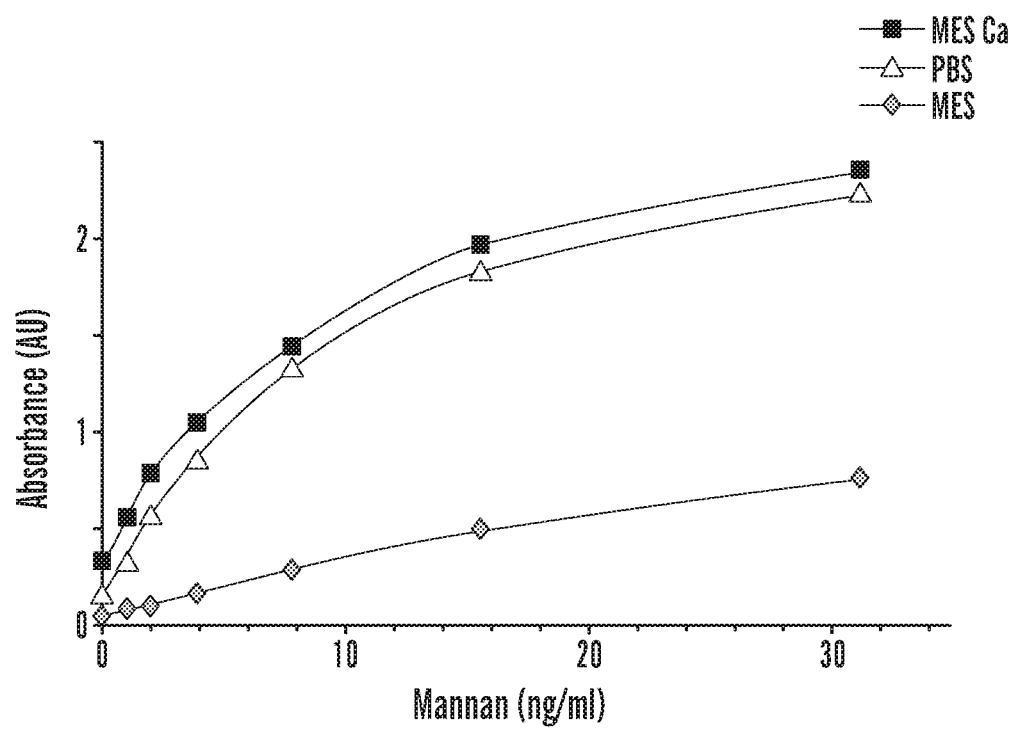
FIG. 8 is a graph showing the attachment of FcMBL to a substrate at 4 degrees (top panel) or 25 degrees (bottom panel).
Figure 8:
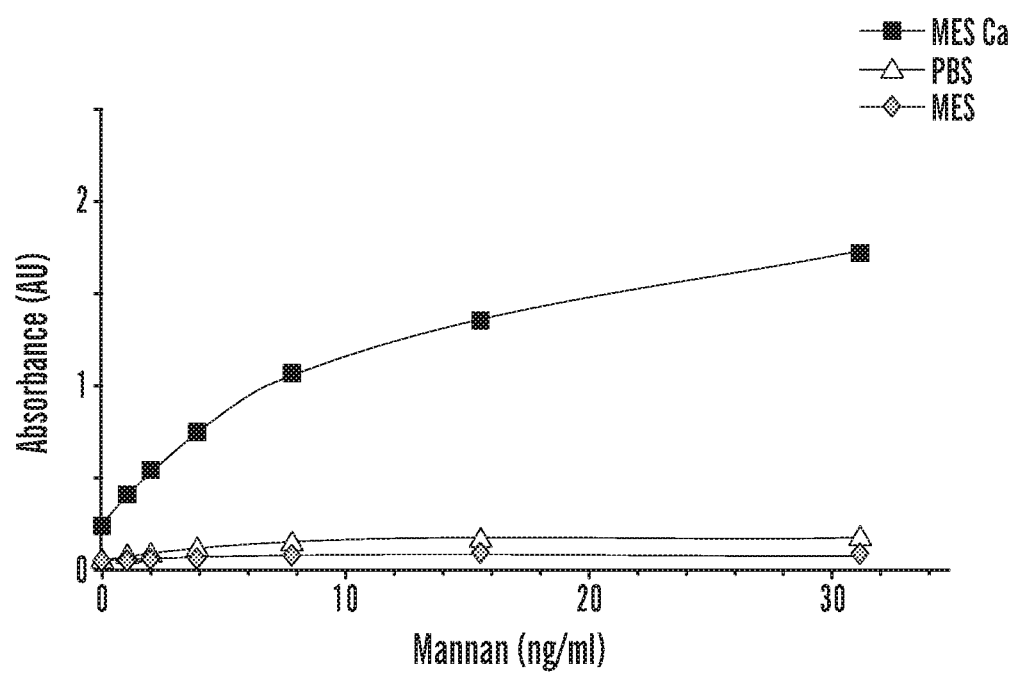

The addition of 10 mM calcium to the coupling buffer helps retain the functionality of the FcMBL for binding ligands in a calcium dependent manner. This is most likely due to the protection of chelating carboxylate groups in the binding pocket of the FcMBL. Additionally, chilling the buffers to 4C helps retain the functionality of the coupled FcMBL as measured by the capacity to bind mannan (FIG. 8).

Figure 9:
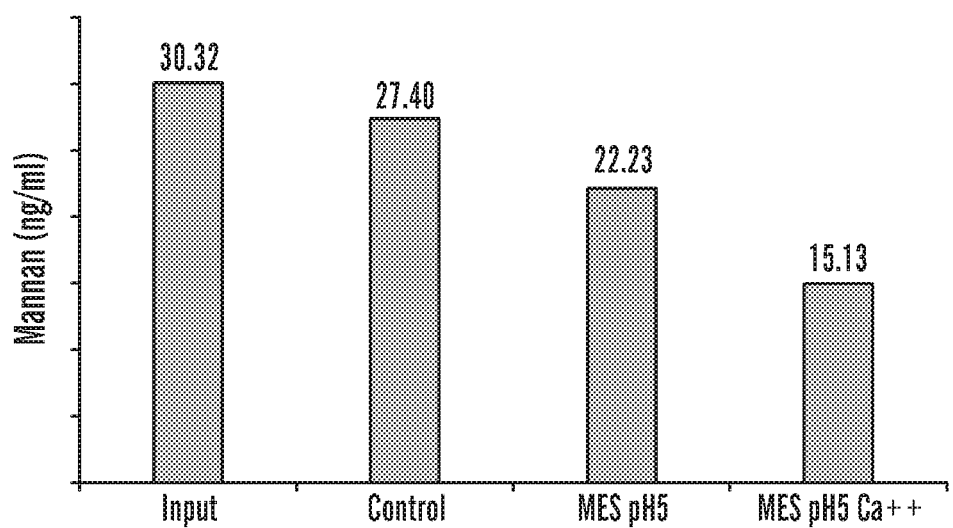
FIG. 9 is a graph showing the Mannan Depletion achieved with FcMBL Coupled Spectrum Filters produced with and without added calcium.

This translates to more mannan binding on filters (greater depletion) with calcium in the conjugation buffer (FIG. 9 and Table 5).

TABLE 5

Mannan depletion with and without calcium added

| Experiment | % Mannan Depletion |
| --- | --- |
| Control | 10% |
| FcMBL Filter (MES pH 5) | 27% |
| FcMBL Filter (MES pH 5 with Calcium) | 50% |

Example 7: Quantifying density of entities attached to a surface

In this Example, the surface polyethersulfone (PES) was functionalized with carboxylic acid groups under the exposure of a $CO_2$ plasma. More specifically, a biomolecule of interest was linked to the modified PES surface with EDC, (1-ethyl-3-(3-dimethylaminopropyl)carbodiimide hydrochloride.

The effectiveness of the EDC conjugation chemistry was examined by comparing the bonding of amine-functionalized quantum dots to the surface of $CO_2$ plasma-modified polyethersulfone surfaces. The amine functionalized quantum dot serves as a suitable analog to the amine residues on proteins. The efficacy of linking quantum dots to the PES surfaces was studied with following experimental cohorts:
1. −EDC, −$CO_2$
2. +EDC, −$CO_2$
3. −EDC, +$CO_2$
4. +EDC, +$CO_2$ For each cohort, three samples were prepared for visual inspection and particle counting by electron microscopy.

Samples were prepared as follows. A stock of QDots was prepared by adding 76.8 uL of the manufacturer's stock (QDot 655 ITK™ amino(PEG) quantum dots, Invitrogen (Cat #Q21521MP) with 4.7 mL of 100 mM MES buffer solution, pH=5. The solution was gently vortexed at a medium setting for 30 seconds to ensure mixing.

3.8 mg of EDC (ThermoScientific, Cat #22980) was weighed and dissolved in 3.8 mL of MES buffer to yield a 1mg/mL concentration.

PES Chips from the plasma modified cohort were exposed to a $CO_2$ plasma for 1 minute at 100W. After plasma modification the PES chips were individually placed into the well of a 24-well plate.

The chips were either each immersed in 400 uL of 100 mM MES, pH=5, or 400 uL of the MES-EDC solution. 400 uL of the QDOT solution was immediately added to each well of a 24 well plate. The chips were checked to ensure proper submersion. The samples were placed at 4° C. on a shaker (LabNet Orbit P4, Speed=25) overnight.

The reaction solution was then aspirated off of the PES samples. The samples were rinsed immediately with DI water to remove excess QDots. The PES chips were transferred to 1.5 mL Eppendorf tubes and immersed in DI water. The tubes with the PES chips were sonicated for an hour. After sonication the DI water was aspirated and the chips were immersed in 30% EtOH. Sonication in ethanol was performed for one more hour. After sonication, each chip was rinsed with five aliquots of 30% ethanol. Following the rinse, the samples were dried and stored under vacuum.

Imaging and image analysis of the QDot samples was performed as follows.

The samples were mounted to stubs with carbon tape. Carbon glue/ink was used to seal any gaps between the surface of the PES chip and the stub. Prior to SEM imaging the samples were sputtered with 1 nm of Pt:Pd (80:20) on an EMS 300T D Dual Head Sputter Coater.

Electron microscopy of the QDots on PES was performed on a Zeiss FESEM Supra 55VP at 3 keV. Images were captured with an InLens detector. All images for particle analysis were taken at 400,000× magnification. The field of view for the microscopy images 753 nm×565 nm=425,000 $nm^2$.

For the MES treated cohort 7-8 spots were imaged on each of the three samples.

The QDots on the surface of the polyethersulfone (PES) chips were tallied with the particle counting algorithm in ImageJ. The process was performed in the following manner. The image scale was calibrated by estimating the pixel length in the image scale bar. Surface roughness in the image was minimized with a bandpass function. Large structures were reduced to 10 pixels. Small structures were brought up to 3 pixels. Secondly, the image was thresholded. Threshold was operated with Intermodes activated. The "Below" value was left at 0.00%. The "Above" value was visually optimized to minimize extraneous features from contributing to the particle count. Magnitude of the value was dependent on the frequency of particles on the surface. Following thresholding, the image was converted to a binary image. For particle counting the size limits were set for 15 nm to infinity. The circularity parameter was 0.5-1. At the above settings, the particles could be slightly underestimated, as small clusters could appear to be one particle.

The estimated particle counts for each cohort are displayed below in Table 6. A single factor ANOVA gave a p-value of 0.002. In the absence of $CO_2$, only low levels of binding were observed. Without the addition of EDC, binding of the particles to the surface of PES was observed (See Table 6, sample 3). With the addition of EDC and $CO_2$, the frequency of QDOT particles increases nearly 2-3 fold relative to the —$CO^2$ controls. The increased frequency of QDot particles in group 4 supports the effectiveness of the EDC carbodiimide chemistry. While not wishing to be bound by theory, the increased frequency of particles in group 3 may be accounted for by an alternative chemistry, such as, imine formation or Schiff's base.

TABLE 6

Particle counts under different coupling conditions

| Sample | Avg. Counts | Stand Dev | Particle Density (Dots/μm2) |
|---|---|---|---|
| 1.) −EDC, −CO2 | 249 | 77 | 586 |
| 2.) +EDC, −CO2 | 251 | 25 | 590 |
| 3.) −EDC, +CO2 | 634 | 163 | 1492 |
| 4.) +EDC, +CO2 | 527 | 46 | 1240 |

While not wishing to be bound by theory, one explanation is that under $CO_2$-plasma derivatization the chemical functionality conferred to the surface would be dominated by carboxylate groups. An additional consequence of the $CO_2$-ion plasma treatment could be the existence of an aldehyde functionality. The presence of an aldehyde surface functionality would permit nucleophilic attack of surface aldehyde groups by the primary amine on the pegylated quantum dot. In this reaction a proton is lost by the nitrogen of the primary amine and water formed with the displaced hydroxyl from the carbonyl leaving an imine or Schiff's base.

What is claimed is:

1. A method of making a substrate having an entity attached thereto, the method comprising:
   i) contacting the substrate with a $CO_2$ plasma to form a modified substrate comprising a plasma-generated-moiety (PGM) comprising a carboxylic acid group, wherein the substrate comprises polysulfone (PS), polyarylethersulfone (PAES) or polyethersulfone (PES); and
   ii) contacting the entity with the modified substrate under conditions sufficient for attachment of the entity to the modified substrate; wherein step ii) contacting is performed for about 4-16 hours;
thereby making a substrate having the entity attached thereto,
   provided that
      the entity comprises a lectin; and
   provided that:
      the modified substrate is not contacted with a crosslinking moiety of derivatized with a crosslinking moiety, prior to attachment of the entity;
      the modified substrate is not contacted with an organic solvent prior to attachment of the entity; and
      the entity is contacted with the modified substrate under aqueous conditions.

2. The method of claim 1, wherein the substrate comprises a lumen.

3. The method of claim 1, wherein the substrate comprises an adhesive or a sealant, and wherein the adhesive or sealant is not contacted with an organic solvent.

4. The method of claim 1, wherein the substrate comprises a dialysis, ultrafiltration, hemofiltration, hemodiafiltration, or hemoperfusion cartridge.

5. The method of claim 1, wherein in step (ii), the modified substrate is substantially free of a crosslinking moiety.

6. The method of claim 1, wherein in step (ii), the modified substrate is substantially free of organic solvent, or wherein the method does not comprise a step of contacting the modified substrate with an organic solvent.

7. The method of claim 1, wherein the method comprises contacting the modified substrate, the entity, or both, with an activating moiety to activate a functional group on the modified substrate, wherein the functional group is a carboxylic acid group.

8. The method of claim 1, wherein step ii) contacting is performed at a pH of 4.

9. The method of claim 1, wherein the PGM comprises a carboxylic acid and the entity comprises an amine and wherein a carboxylic acid of the PGM covalently binds with an amine group of the entity.

10. The method of claim 1, wherein at least 1% of the PGMs comprise a carboxylic acid group.

11. The method of claim 1, wherein step 1, contacting comprises contacting a plurality of substrates with the plasma in a vacuum chamber of a radio frequency plasma generator.

12. The method of claim 1, wherein the entity comprises a polypeptide of SEQ ID NO: 4 or at least 80% identical to SEQ ID NO: 4, or a polypeptide of SEQ ID NO: 6 or at least 80% identical to SEQ ID NO: 6.

13. A device comprising a substrate having an entity attached thereto, produced by the method of claim 1.

14. The method of claim 1, wherein the plasma consists essentially of $CO_2$ plasma or consists of $CO_2$ plasma.

15. The method of claim 3 wherein the PGM comprises an aldehyde group.

16. The method of claim 1, wherein the plasma treatment step is less than 10 minutes.

17. The method of claim 1, wherein the plasma is generated by a plasma generator under a radio frequency of about 12 MHz to 15 MHz.

18. The method of claim 17, wherein the plasma generator comprises electrodes outside a vacuum chamber of the plasma generator.

19. The method of claim 1, wherein step i) contacting comprises contacting the substrate with the plasma in a vacuum chamber of a radio frequency plasma generator, and the plasma is generated by the plasma generator under a radio frequency of about 12 MHz to 15 MHz.

20. The method of claim 1, wherein the entities are attached at a density of at least about $1 \times 10^{12}$ molecules per $cm^2$.

21. The method of claim 1, wherein the contacting of step ii) is performed in a solution comprising 2-morpholino-ethane sulfonic acid (MES) buffer.

22. The method of claim 1, wherein step ii) contacting is performed for about 4-6 hours.

* * * * *